(12) United States Patent
Hughes et al.

(10) Patent No.: US 7,812,170 B2
(45) Date of Patent: Oct. 12, 2010

(54) INSECTICIDES

(75) Inventors: David John Hughes, Bracknell (GB); James Edward Peace, Bracknell (GB); Suzanna Riley, Bracknell (GB); Sally Russell, Bracknell (GB); Joseph John Swanborough, Bracknell (GB); Roger Graham Hall, Basel (CH); André Jeanguenat, Basel (CH); Olivier Loiseleur, Basel (CH); Peter Renold, Basel (CH); Stephan Trah, Basel (CH); Jean Wenger, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 775 days.

(21) Appl. No.: 10/598,041

(22) PCT Filed: Mar. 2, 2005

(86) PCT No.: PCT/EP2005/002204

§ 371 (c)(1), (2), (4) Date: Jun. 28, 2007

(87) PCT Pub. No.: WO2005/085234

PCT Pub. Date: Sep. 15, 2005

(65) Prior Publication Data

US 2007/0281930 A1 Dec. 6, 2007

(30) Foreign Application Priority Data

| Mar. 3, 2004 | (GB) | 0404801.3 |
| May 18, 2004 | (GB) | 0411078.9 |
| Nov. 18, 2004 | (GB) | 0425453.8 |

(51) Int. Cl.
C07D 401/00 (2006.01)

(52) U.S. Cl. .................. 546/275.4; 546/162

(58) Field of Classification Search ............. 546/162, 546/275.4
See application file for complete search history.

(56) References Cited

U.S. PATENT DOCUMENTS

| 2003/0229050 A1 | 12/2003 | Lahm et al. | |
| 2005/0245580 A1* | 11/2005 | Freudenberger et al. | 514/341 |
| 2006/0241304 A1* | 10/2006 | Taylor | 546/275.4 |

FOREIGN PATENT DOCUMENTS

| NL | 9202078 A | 6/1994 |
| WO | 96-16954 A1 | 6/1996 |
| WO | 98-17648 A1 | 4/1998 |
| WO | 99-55663 A1 | 11/1999 |
| WO | 02-094765 A2 | 11/2002 |
| WO | 03-015518 A1 | 2/2003 |
| WO | 03-015519 A1 | 2/2003 |
| WO | 03-016284 A1 | 2/2003 |
| WO | 03-024222 A1 | 3/2003 |
| WO | 2004-014844 A2 | 2/2004 |
| WO | 2004-099127 A1 | 11/2004 |

OTHER PUBLICATIONS

Mehta, H.J. et al: Journal of the Indian Chemical Society, vol. 49, No. 4, 1972, pp. 407-414.
Mehta, V.K. et al: Indian Journal of Chemistry, vol. 6, No. 6, 1968, pp. 294-296.

* cited by examiner

Primary Examiner—Shailendra Kumar
(74) Attorney, Agent, or Firm—James Cueva

(57) ABSTRACT

Compounds of the formula (I) in which $Z_1$ is an oxygen atom; or a sulfur atom; $Z_2$ is an oxygen atom; or a sulfur atom; $R_1$ is an aryl or heteroaryl group, which is unsubstituted or substituted; $R_2$ is hydrogen; or an organic substituent; $R_3$ is hydrogen; or an organic substituent; $R_4$ is hydrogen; or an organic substituent; or $R_3$ and $R_4$, taken together, form, together with the nitrogen atom, to which they are attached, a ring, which is unsubstituted or substituted; $R_5$ is hydrogen; or an unsubstituted or substituted alkyl group; or forms, taken together with $R_8$ or with a monovalent substituent attached to that atom of $R_6$, via which atom $R_6$ is directly connected with the carbon atom, shown in the formula I, which carries $R_5$, one additional bond; $R_6$ and $R_7$, taken together, form, together with the two carbon atoms, shown in the formula I, to which atoms they are attached, a bicyclic ring system, which ring system is carbocyclic or heterocyclic, which ring system is substituted, in the manner shown in the formula I, by the four substituents —N(R2)-C(=Z1)-R, —C(=Z2)-N(R3)-R4, $R_5$ and R8, and which ring system is optionally further substituted; and $R_8$ is hydrogen; or an unsubstituted or substituted alkyl group; or forms, taken together with $R_5$ or with a monovalent substituent attached to that atom of $R_7$, via which atom $R_7$ is directly connected with the carbon atom, shown in the formula I, which carries R8, one additional bond, and, where appropriate, tautomers thereof, in each case in free form or in salt form, can be used as agrochemical active ingredients and can be prepared in a manner known per se.

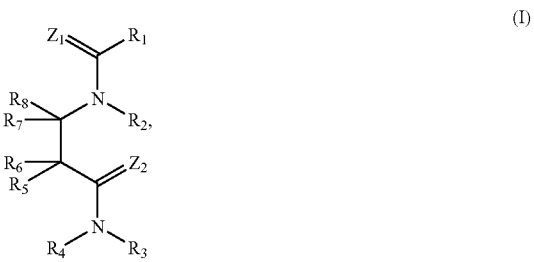

(I)

1 Claim, No Drawings

INSECTICIDES

This application is a 371 of International Application No. PCT/EP2005/002204 filed Mar. 2, 2005, which claims priority to GB 0404801.3 filed Mar. 3, 2004, GB 0411078.9 filed May 18, 2004, and GB 0425453.8 filed Nov. 18, 2004, the contents of which are incorporated herein by reference.

The present invention relates to bicyclic bisamide derivatives, to processes for their preparation, to compositions comprising those compounds, and to their use for controlling insects or representatives of the order Acarina.

Bisamide derivatives with insecticidal action are known and described, for example, in US 2003/0229050.

There have now been found novel bicyclic bisamide derivatives with pesticidal properties. The present invention accordingly relates to compounds of formula I

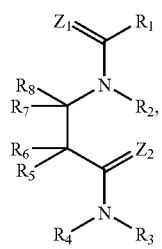

(I)

in which
- $Z_1$ is an oxygen atom; or a sulfur atom;
- $Z_2$ is an oxygen atom; or a sulfur atom;
- $R_1$ is an aryl or heteroaryl group, which is unsubstituted or substituted;
- $R_2$ is hydrogen; or an organic substituent;
- $R_3$ is hydrogen; or an organic substituent;
- $R_4$ is hydrogen; or an organic substituent;
- or $R_3$ and $R_4$, taken together, form, together with the nitrogen atom, to which they are attached, a ring, which is unsubstituted or substituted;
- $R_5$ is hydrogen; or an unsubstituted or substituted alkyl group; or forms, taken together with $R_8$ or with a monovalent substituent attached to that atom of $R_6$, via which atom $R_6$ is directly connected with the carbon atom, shown in the formula I, which carries $R_5$, one additional bond;
- $R_6$ and $R_7$, taken together, form, together with the two carbon atoms, shown in the formula I, to which atoms they are attached, a bicyclic ring system, which ring system is carbocyclic or heterocyclic, which ring system is substituted, in the manner shown in the formula I, by the four substituents —$N(R_2)$—$C(=Z_1)$—$R_1$, —$C(=Z_2)$—$N(R_3)$—$R_4$, $R_5$ and $R_8$, and which ring system is optionally further substituted;
- and $R_8$ is hydrogen; or an unsubstituted or substituted alkyl group; or forms, taken together with $R_5$ or with a monovalent substituent attached to that atom of $R_7$, via which atom $R_7$ is directly connected with the carbon atom, shown in the formula I, which carries $R_8$, one additional bond, in free form or in salt form, where appropriate to tautomers, in free form or in salt form, of these compounds, to a process for the preparation and to the use of these compounds and tautomers, to pesticidal compositions whose active ingredient is selected from amongst these compounds and tautomers, in each case in free form or in agrochemically utilizable salt form, to a process for the preparation and to the use of these compositions, to plant propagation material treated with these compositions, to a method of controlling pests with these active ingredients and compositions, to intermediates, in free form or in salt form, for the preparation of these compounds, where appropriate to tautomers, in free form or in salt form, of these intermediates, and to a process for the preparation and to the use of these intermediates.

In some cases, the compounds of formula I can exist as tautomers. For example, if in the compounds of formula I the substituent —$N(R_2)$—$C(=Z_1)$—$R_1$ is —$N(R_2)$—$C(=O)$—$R_1$ and $R_2$ is hydrogen, corresponding compounds of formula I, i.e. those in which —$N(R_2)$—$C(=Z_1)$—$R_1$ is —$N(H)$—$C(=O)$—$R_1$, can be in equilibrium with the respective tautomers, in which the respective substituent has the tautomeric structure —$N=C(OH)$—$R_1$. Accordingly, the compounds of formula I hereinabove and hereinbelow are to be understood as including such tautomers, where appropriate, even though the latter are not mentioned specifically in each individual case.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-loweralkylamine, for example ethyl-, diethyl-, triethyl- or dimethylpropylamine, or a mono-, di- or trihydroxy-lower-alkylamine, for example mono-, di- or triethanolamine. Where appropriate, the corresponding internal salts can furthermore be formed. Preferred within the scope of the invention are agrochemically advantageous salts; however, the invention also encompasses salts which have disadvantage for agrochemical use, for example salts which are toxic to bees or fish, and which are employed, for example, for the isolation or purification of free compounds of formula I or agrochemically utilizable salts thereof. Owing to the close relationship between the compounds of formula I in free form and in the form of their salts, for the purposes of the invention the free compounds of formula I or their salts hereinabove and hereinbelow are respectively to be understood as including, where appropriate, the corresponding salts or the free compounds of formula I. The same applies analogously to tautomers of compounds of formula I and salts thereof. In general, the free form is preferred in each case.

Preferably the invention relates (2) to a compound according to (1) of formula I, in which
- $Z_1$ is an oxygen atom; or a sulfur atom;
- $Z_2$ is an oxygen atom; or a sulfur atom;

$R_1$ is a phenyl or naphthyl group, which is substituted independently by 1 or 2 substituents $R_a$ and optionally further substituted independently by 1 to 3 substituents $R_b$;

$R_a$ is cyano; nitro; halogen; $C_1$-$C_6$alkyl; halo-$C_1$-$C_6$alkyl; $C_1$-$C_6$alkoxy-$C_1$-$C_6$alkyl; $C_2$-$C_6$alkenyl; halo-$C_2$-$C_6$alkenyl; $C_2$-$C_6$alkynyl; halo-$C_2$-$C_6$alkynyl; $C_3$-$C_6$cycloalkyl; $C_6$cycloalkyl; hydroxy; $C_1$-$C_6$alkoxy; halo-$C_1$-$C_6$alkoxy; $C_3$-$C_6$cycloalkoxy; mercapto; $C_1$-$C_6$alkylthio; halo-$C_1$-$C_6$alkylthio; $C_1$-$C_6$alkylsulfinyl; halo-$C_1$-$C_6$alkylsulfinyl; $C_1$-$C_6$alkylsulfonyl; halo-$C_1$-$C_6$alkylsulfonyl; amino; $C_1$-$C_6$alkylamino; halo-$C_1$-$C_6$alkylamino; di-$C_1$-$C_6$alkylamino, in which the two alkyl groups are the same or different or, taken together, form, together with the nitrogen atom, to which they are attached, a ring containing 1 ring nitrogen atom and 2 to 12 ring carbon atoms and optionally 1 further ring hetero atom, which then replaces 1 ring carbon atom and is selected from the group, consisting of an oxygen, a sulfur and a nitrogen atom, which ring is unsubstituted or substituted independently by 1 to 4 substituents, selected from the group, consisting of cyano, nitro, halogen, $C_1$-$C_4$alkyl and $C_1$-$C_4$alkoxy; di-(halo-$C_1$-$C_6$alkyl)-amino, in which the two haloalkyl groups are the same or different; $C_3$-$C_6$cycloalkylamino; N—($C_1$-$C_6$alkyl)-N—($C_3$-$C_6$cycloalkyl)-amino; carboxy; $C_1$-$C_6$alkoxycarbonyl; halo-$C_1$-$C_6$alkoxycarbonyl; aminocarbonyl; $C_1$-$C_6$alkylaminocarbonyl; halo-$C_1$-$C_6$alkylaminocarbonyl; di-$C_1$-$C_6$alkylaminocarbonyl, in which the two alkyl groups are the same or different or, taken together, form, together with the nitrogen atom, to which they are attached, a ring containing 1 ring nitrogen atom and 2 to 12 ring carbon atoms and optionally 1 further ring hetero atom, which then replaces 1 ring carbon atom and is selected from the group, consisting of an oxygen, a sulfur and a nitrogen atom, which ring is unsubstituted or substituted independently by 1 to 4 substituents, selected from the group, consisting of cyano, nitro, halogen, $C_1$-$C_4$alkyl and $C_1$-$C_4$alkoxy; di-(halo-$C_1$-$C_6$alkyl)-aminocarbonyl, in which the two haloalkyl groups are the same or different; $C_1$-$C_6$alkylcarbonyl; halo-$C_1$-$C_6$alkylcarbonyl; or tri-$C_1$-$C_6$alkylsilyl, in which the three alkyl groups are the same or different;

or 2 substituents $R_a$, which are attached to adjacent carbon atoms, taken together, are —($CH_2$—)$_3$; —($CH_2$—)$_4$; —($CH_2$—)$_5$; —(CH=CH—)$_2$; —$OCH_2$O—; —O—($CH_2$—)$_2$O—; —O—($CF_2$—)$_2$; or —O—($CF_2$—)$_2$O—;

$R_b$ is halogen; $C_1$-$C_6$alkyl; $C_2$-$C_6$alkenyl; $C_2$-$C_6$alkynyl; $C_3$-$C_6$cycloalkyl; $C_1$-$C_6$alkoxy; $C_1$-$C_6$alkoxycarbonyl; or a phenyl, benzyl, phenoxy or monocyclic or bicyclic heteroaryl group, which group is unsubstituted or substituted independently by 1 to 4 substituents, selected from the group, consisting of the substituents $R_a$;

or $R_1$ is a monocyclic or bicyclic heteroaryl group, which is unsubstituted or substituted independently by 1 to 4 substituents $R_c$;

$R_c$ is a substituent $R_a$; or a phenyl, benzyl, benzoyl, phenoxy or monocyclic or bicyclic heteroaryl group, which group is unsubstituted or substituted independently by 1 to 4 substituents, selected from the group, consisting of the substituents $R_a$;

$R_2$ is hydrogen; a $C_1$-$C_6$alkyl, $C_2$-$C_6$alkenyl, $C_2$-$C_6$alkynyl or $C_3$-$C_6$cycloalkyl group, which group is unsubstituted or substituted independently by one or more substituents, selected from the group, consisting of the substituents $R_a$; a group C(=O)$R_d$; or a group C(=S)$R_d$;

$R_d$ is a substituent $R_1$; $C_1$-$C_6$alkyl; halo-$C_1$-$C_6$alkyl; $C_1$-$C_6$alkoxy-$C_1$-$C_6$alkyl; a group $CH_2R_1$; a group $CH_2OR_1$; a group $CH_2SR_1$; a group $CH_2NHR_1$, which group is optionally further substituted at the nitrogen atom by $C_1$-$C_6$alkyl or halo-$C_1$-$C_6$alkyl; $C_2$-$C_6$alkenyl; halo-$C_2$-$C_6$alkenyl; $C_2$-$C_6$alkynyl; halo-$C_2$-$C_6$alkynyl; $C_3$-$C_6$cycloalkyl; halo-$C_3$-$C_6$cycloalkyl; $C_1$-$C_6$alkoxy; halo-$C_1$-$C_6$alkoxy; $C_3$-$C_6$cycloalkoxy; a group $OR_1$; $C_1$-$C_6$alkylthio; halo-$C_1$-$C_6$alkylthio; a group $SR_1$; $C_1$-$C_6$alkylamino; halo-$C_1$-$C6$alkylamino; di-$C_1$-$C_6$alkylamino, in which the two alkyl groups are the same or different or, taken together, form, together with the nitrogen atom, to which they are attached, a ring containing 1 ring nitrogen atom and 2 to 12 ring carbon atoms and optionally 1 further ring hetero atom, which then replaces 1 ring carbon atom and is selected from the group, consisting of an oxygen, a sulfur and a nitrogen atom, which ring is unsubstituted or substituted independently by 1 to 4 substituents, selected from the group, consisting of cyano, nitro, halogen, $C_1$-$C_4$alkyl and $C_1$-$C_4$alkoxy; di-(halo-$C_1$-$C_6$alkyl)-amino, in which the two haloalkyl groups are the same or different; $C_3$-$C_6$cycloalkylamino; N—($C_1$-$C_6$alkyl)-N—($C_3$-$C_6$cycloalkyl)-amino; or a group $NHR_1$, which group is optionally further substituted at the nitrogen atom by $C_1$-$C_6$alkyl or halo-$C_1$-$C_6$alkyl;

$R_3$ is hydrogen; a $C_1$-$C_6$alkyl, $C_2$-$C_6$alkenyl, $C_2$-$C_6$alkynyl or $C_3$-$C_6$cycloalkyl group, which group is unsubstituted or substituted independently by one or more substituents, selected from the group, consisting of the substituents $R_a$; $C_1$-$C_6$alkoxy; halo-$C_1$-$C_6$alkoxy; $C_3$-$C_6$cycloalkoxy; $C_1$-$C_6$alkylthio; halo-$C_1$-$C_6$alkylthio; $C_1$-$C_6$alkylamino; halo-$C_1$-$C_6$alkoxy; di-$C_1$-$C_6$alkylamino, in which the two alkyl groups are the same or different or, taken together, form, together with the nitrogen atom, to which they are attached, a ring containing 1 ring nitrogen atom and 2 to 12 ring carbon atoms and optionally 1 further ring hetero atom, which then replaces 1 ring carbon atom and is selected from the group, consisting of an oxygen, a sulfur and a nitrogen atom, which ring is unsubstituted or substituted independently by 1 to 4 substituents, selected from the group, consisting of cyano, nitro, halogen, $C_1$-$C_4$alkyl and $C_1$-$C_4$alkoxy; di-(halo-$C_1$-$C_6$alkyl)-amino, in which the two haloalkyl groups are the same or different; $C_3$-$C_6$cycloalkylamino; N—($C_1$-$C_6$alkyl)-N—($C_3$-$C_6$cycloalkyl)-amino; $C_1$-$C_6$alkoxycarbonyl; halo-$C_1$-$C_6$alkoxycarbonyl; $C_1$-$C_6$alkylcarbonyl or halo-$C_1$-$C_6$alkylcarbonyl;

$R_4$ is hydrogen; a substituent $R_1$; a substituent $R_e$; a $C_1$-$C_6$alkyl, $C_2$-$C_6$alkenyl, $C_2$-$C_6$alkynyl or $C_3$-$C_6$cycloalkyl group, which group is unsubstituted or substituted independently by one or more substituents, selected from the group, consisting of the substituents $R_a$, the substituents $R_e$ and a phenyl, benzoyl, phenoxy or monocyclic or bicyclic heteroaryl group, which group is unsubstituted or substituted independently by 1 to 4 substituents, selected from the group, consisting of the substituents $R_c$; a group $CH_2OR_1$; a group $CH_2SR_1$; a group $CH_2NHR_1$, which group is optionally further substituted at the nitrogen atom by $C_1$-$C_6$alkyl or halo-$C_1$-$C_6$alkyl; $C_1$-$C_6$alkoxy; halo-$C_1$-$C_6$alkoxy; $C_3$-$C_6$cycloalkoxy; a group $OR_1$; $C_1$-$C_6$alkylthio; halo-$C_1$-$C_6$alkylthio; a group $SR_1$; $C_1$-$C_6$alkylsulfinyl; halo-$C_1$-$C_6$alkylsulfinyl; $C_1$-$C_6$alkylsulfonyl; halo-$C_1$-

$C_6$alkylsulfonyl; $C_1$-$C_6$alkylamino; halo-$C_1$-$C_6$alkylamino; di-$C_1$-$C_6$alkylamino, in which the two alkyl groups are the same or different or, taken together, form, together with the nitrogen atom, to which they are attached, a ring containing 1 ring nitrogen atom and 2 to 12 ring carbon atoms and optionally 1 further ring hetero atom, which then replaces 1 ring carbon atom and is selected from the group, consisting of an oxygen, a sulfur and a nitrogen atom, which ring is unsubstituted or substituted independently by 1 to 4 substituents, selected from the group, consisting of cyano, nitro, halogen, $C_1$-$C_4$alkyl and $C_1$-$C_4$alkoxy; di-(halo-$C_1$-$C_6$alkyl)-amino, in which the two haloalkyl groups are the same or different; $C_3$-$C_6$cycloalkylamino; N—($C_1$-$C_6$alkyl)-N-($C_3$-$C_6$cycloalkyl)-amino; a group $NHR_1$, which group is optionally further substituted at the nitrogen atom by $C_1$-$C_6$alkyl or halo-$C_1$-$C_6$alkyl; a group $C(=O)R_d$; a group $C(=O)R_e$; a group $C(=S)R_d$; or a group $C(=S)R_e$;

$R_e$ is a carbocyclyl or heterocyclyl group, which group is monocyclic or bicyclic and is non-aromatic, in which group 1 or 2 of the ring members are optionally selected from the group, consisting of the groups $C(=O)$, $S(=O)$ and $S(=O)_2$, and which group is unsubstituted or substituted independently by 1 to 4 substituents, selected from the group, consisting of cyano, nitro, halogen, $C_1$-$C_4$alkyl and $C_1$-$C_4$alkoxy;

or $R_3$ and $R_4$, taken together, form, together with the nitrogen atom, to which they are attached, a ring containing 1 ring nitrogen atom and 2 to 6 ring carbon atoms and optionally 1 further ring hetero atom, which then replaces 1 ring carbon atom and is selected from the group, consisting of an oxygen, a sulfur and a nitrogen atom, which ring is unsubstituted or substituted independently by 1 to 4 substituents, selected from the group, consisting of cyano, nitro, halogen, $C_1$-$C_4$alkyl and $C_1$-$C_4$alkoxy;

$R_5$ is hydrogen; $C_1$-$C_6$alkyl; or halo-$C_1$-$C_6$alkyl; or has one of the meanings defined hereinafter;

$R_6$ and $R_7$, taken together, are either a group of the formula

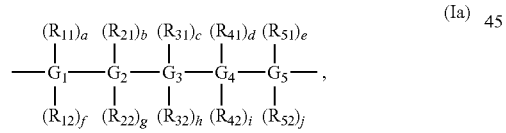
(Ia)

in which $G_1$ is attached to the carbon atom, shown in the formula I, that carries $R_5$; and in which $G_5$ is attached to the carbon atom, shown in the formula I, that carries $R_8$; or are a group of the formula

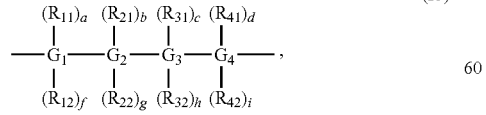
(Ib)

in which $G_1$ is attached to the carbon atom, shown in the formula I, that carries $R_5$; and in which $G_4$ is attached to the carbon atom, shown in the formula I, that carries $R_8$; or are a group of the formula

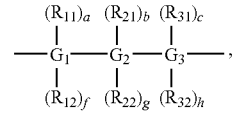
(Ic)

in which $G_1$ is attached to the carbon atom, shown in the formula I, that carries $R_5$; and in which $G_3$ is attached to the carbon atom, shown in the formula I, that carries $R_8$;

in which formulae Ia, Ib and Ic either a is 0; f is 0; and $G_1$ is a group $C(=O)$; a group $C(=S)$; an oxygen atom; a sulfur atom; a group $S(=O)$; or a group $S(=O)_2$; or a is 0; f is 1; and $G_1$ is a nitrogen atom; or a is 1; f is 1; and $G_1$ is a carbon atom; either b is 0; g is 0; and $G_2$ is a group $C(=O)$; a group $C(=S)$; an oxygen atom; a sulfur atom; a group $S(=O)$; or a group $S(=O)_2$; or b is 0; g is 1; and $G_2$ is a nitrogen atom; or b is 1; g is 1; and $G_2$ is a carbon atom; and either c is 0; h is 0; and $G_3$ is a group $C(=O)$; a group $C(=S)$; an oxygen atom; a sulfur atom; a group $S(=O)$; or a group $S(=O)_2$; or c is 0; h is 1; and $G_3$ is a nitrogen atom; or c is 1; h is 1; and $G_3$ is a carbon atom;

in which formulae Ia and Ib either d is 0; i is 0; and $G_4$ is a group $C(=O)$; a group $C(=S)$; an oxygen atom; a sulfur atom; a group $S(=O)$; or a group $S(=O)_2$; or d is 0; i is 1; and $G_4$ is a nitrogen atom; or d is 1; i is 1; and $G_4$ is a carbon atom;

in which formula Ia either e is 0; j is 0; and $G_5$ is a group $C(=O)$; a group $C(=S)$; an oxygen atom; a sulfur atom; a group $S(=O)$; or a group $S(=O)_2$; or e is 0; j is 1; and $G_5$ is a nitrogen atom; or e is 1; j is 1; and $G_5$ is a carbon atom;

in which formula Ia either f is 1; g is 1; and $R_{12}$ and $R_{22}$, taken together, are either a group of the formula

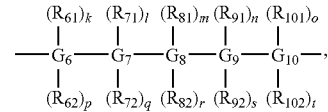
(Id)

in which $G_6$ is attached to $G_1$; and in which $G_{10}$ is attached to $G_2$; or are a group of the formula

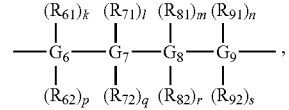
(Ie)

in which $G_6$ is attached to $G_1$; and in which $G_9$ is attached to $G_2$; or are a group of the formula

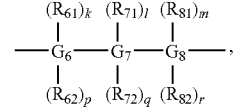
(If)

in which $G_6$ is attached to $G_1$; and in which $G_8$ is attached to $G_2$;

or g is 1; h is 1; and $R_{22}$ and $R_{32}$, taken together, are either a group of the formula Id, in which $G_6$ is attached to $G_2$; and in which $G_{10}$ is attached to $G_3$; or are a group of the formula Ie, in which $G_6$ is attached to $G_2$; and in which $G_9$ is attached to $G_3$; or are a group of the formula If, in which $G_6$ is attached to $G_2$; and in which $G_8$ is attached to $G_3$;

or h is 1; i is 1; and $R_{32}$ and $R_{42}$, taken together, are either a group of the formula Id, in which $G_6$ is attached to $G_3$; and in which $G_{10}$ is attached to $G_4$; or are a group of the formula Ie, in which $G_6$ is attached to $G_3$; and in which $G_9$ is attached to $G_4$; or are a group of the formula If, in which $G_6$ is attached to $G_3$; and in which $G_8$ is attached to $G_4$;

or i is 1; j is 1; and $R_{42}$ and $R_{52}$, taken together, are either a group of the formula Id, in which $G_6$ is attached to $G_4$; and in which $G_{10}$ is attached to $G_5$; or are a group of the formula Ie, in which $G_6$ is attached to $G_4$; and in which $G_9$ is attached to $G_5$; or are a group of the formula If, in which $G_6$ is attached to $G_4$; and in which $G_8$ is attached to $G_5$;

in which formula Ib either f is 1; g is 1; and $R_{12}$ and $R_{22}$, taken together, are either a group of the formula Id, in which $G_6$ is attached to $G_1$; and in which $G_{10}$ is attached to $G_2$; or are a group of the formula Ie, in which $G_6$ is attached to $G_1$; and in which $G_9$ is attached to $G_2$; or are a group of the formula If, in which $G_6$ is attached to $G_1$; and in which $G_8$ is attached to $G_2$;

or g is 1; h is 1; and $R_{22}$ and $R_{32}$, taken together, are either a group of the formula Id, in which $G_6$ is attached to $G_2$; and in which $G_{10}$ is attached to $G_3$; or are a group of the formula Ie, in which $G_6$ is attached to $G_2$; and in which $G_9$ is attached to $G_3$; or are a group of the formula If, in which $G_6$ is attached to $G_2$; and in which $G_8$ is attached to $G_3$;

or h is 1; i is 1; and $R_{32}$ and $R_{42}$, taken together, are either a group of the formula Id, in which $G_6$ is attached to $G_3$; and in which $G_{10}$ is attached to $G_4$; or are a group of the formula Ie, in which $G_6$ is attached to $G_3$; and in which $G_9$ is attached to $G_4$; or are a group of the formula If, in which $G_6$ is attached to $G_3$; and in which $G_8$ is attached to $G_4$;

in which formula Ic either f is 1; g is 1; and $R_{12}$ and $R_{22}$, taken together, are either a group of the formula Id, in which $G_6$ is attached to $G_1$; and in which $G_{10}$ is attached to $G_2$; or are a group of the formula Ie, in which $G_6$ is attached to $G_1$; and in which $G_9$ is attached to $G_2$; or are a group of the formula If, in which $G_6$ is attached to $G_1$; and in which $G_8$ is attached to $G_2$;

or g is 1; h is 1; and $R_{22}$ and $R_{32}$, taken together, are either a group of the formula Id, in which $G_6$ is attached to $G_2$; and in which $G_{10}$ is attached to $G_3$; or are a group of the formula Ie, in which $G_6$ is attached to $G_2$; and in which $G_9$ is attached to $G_3$; or are a group of the formula If, in which $G_6$ is attached to $G_2$; and in which $G_8$ is attached to $G_3$;

in which formulae Ia, Ib and Ic the atoms $G_1$ and $G_2$ can be connected by one additional bond, which bond, if present, is represented by a first substituent, which is $R_{12}$, if $G_1$ is a nitrogen atom, and which is $R_{11}$ or $R_{12}$, if $G_1$ is a carbon atom, and a second substituent, which is $R_{22}$, if $G_2$ is a nitrogen atom, and which is $R_{21}$ or $R_{22}$, if $G_2$ is a carbon atom, taken together;

in which formulae Ia, Ib and Ic the atoms $G_2$ and $G_3$ can be connected by one additional bond, which bond, if present, is represented by a first substituent, which is $R_{22}$, if $G_2$ is a nitrogen atom, and which is $R_{21}$ or $R_{22}$, if $G_2$ is a carbon atom, and a second substituent, which is $R_{32}$, if $G_3$ is a nitrogen atom, and which is $R_{31}$ or $R_{32}$, if $G_3$ is a carbon atom, taken together;

in which formulae Ia and Ib the atoms $G_3$ and $G_4$ can be connected by one additional bond, which bond, if present, is represented by a first substituent, which is $R_{32}$, if $G_3$ is a nitrogen atom, and which is $R_{31}$ or $R_{32}$, if $G_3$ is a carbon atom, and a second substituent, which is $R_{42}$, if $G_4$ is a nitrogen atom, and which is $R_{41}$ or $R_{42}$, if $G_4$ is a carbon atom, taken together;

in which formula Ia the atoms $G_4$ and $G_5$ can be connected by one additional bond, which bond, if present, is represented by a first substituent, which is $R_{42}$, if $G_4$ is a nitrogen atom, and which is $R_{41}$ or $R_{42}$, if $G_4$ is a carbon atom, and a second substituent, which is $R_{52}$, if $G_5$ is a nitrogen atom, and which is $R_{51}$ or $R_{52}$, if $G_5$ is a carbon atom, taken together;

in which formulae Ia, Ib and Ic the atom $G_1$ can be connected with the carbon atom, shown in the formula I, that carries $R_5$, by one additional bond, which bond, if present, is represented by a first substituent, which is $R_{12}$, if $G_1$ is a nitrogen atom, and which is $R_{11}$ or $R_{12}$, if $G_1$ is a carbon atom, and a second substituent, which is $R_5$, taken together;

in which formula Ia the atom $G_5$ can be connected with the carbon atom, shown in the formula I, that carries $R_8$, by one additional bond, which bond, if present, is represented by a first substituent, which is $R_{52}$, if $G_5$ is a nitrogen atom, and which is $R_{51}$ or $R_{52}$, if $G_5$ is a carbon atom, and a second substituent, which is $R_8$, taken together;

in which formula Ib the atom $G_4$ can be connected with the carbon atom, shown in the formula I, that carries $R_8$, by one additional bond, which bond, if present, is represented by a first substituent, which is $R_{42}$, if $G_4$ is a nitrogen atom, and which is $R_{41}$ or $R_{42}$, if $G_4$ is a carbon atom, and a second substituent, which is $R_8$, taken together;

in which formula Ic the atom $G_3$ can be connected with the carbon atom, shown in the formula I, that carries $R_8$, by one additional bond, which bond, if present, is represented by a first substituent, which is $R_{32}$, if $G_3$ is a nitrogen atom, and which is $R_{31}$ or $R_{32}$, if $G_3$ is a carbon atom, and a second substituent, which is $R_8$, taken together;

in which formula Ia each of those substituents, selected from the group, consisting of the substituents $R_{11}$, $R_{12}$, $R_{21}$, $R_{22}$, $R_{31}$, $R_{32}$, $R_{41}$, $R_{42}$, $R_{51}$ and $R_{52}$, which are different from the two substituents, which, taken together, form the group of the formula Id, Ie or If, and different from any first substituent, if present, as defined hereinbefore for the formula Ia, and from any second substituent, if present, as defined hereinbefore for the formula Ia, is independently selected from the group, consisting of the substituents $R_1$;

in which formula Ib each of those substituents, selected from the group, consisting of the substituents $R_{11}$, $R_{12}$, $R_{21}$, $R_{22}$, $R_{31}$, $R_{32}$, $R_{41}$ and $R_{42}$, which are different from the two substituents, which, taken together, form the group of the formula Id, Ie or If, and different from any first substituent, if present, as defined hereinbefore for the formula Ib, and from any second substituent, if present, as defined hereinbefore for the formula Ib, is independently selected from the group, consisting of the substituents $R_f$;

in which formula Ic each of those substituents, selected from the group, consisting of the substituents $R_{11}$, $R_{12}$, $R_{21}$, $R_{22}$, $R_{31}$ and $R_{32}$, which are different from the two substituents, which, taken together, form the group of the formula Id, Ie or If, and different from any first substituent, if present, as defined hereinbefore for the formula Ic, and from any second substituent, if present, as defined hereinbefore for the formula Ic, is independently selected from the group, consisting of the substituents $R_f$;

$R_f$ is hydrogen; or a substituent $R_g$; the total number of the substituents $R_g$, if present, having an upper limit of 5 for a group of the formula Ia; of 4 for a group of the formula Ib; and of 3 for a group of the formula Ic; which total number can, however, be limited for a specific group of the formula Ia, Ib or Ic to a value lower than the upper limit mentioned hereinbefore, which value is then equal to the number of the positions available for the substitution by a substituent $R_g$ in this specific group;

$R_g$ is either attached to a carbon atom and then selected from the group, consisting of the substituents $R_{g\text{-}c}$; or attached to a nitrogen atom and then selected from the group, consisting of the substituents $R_{g\text{-}n}$;

$R_{g\text{-}c}$ is a substituent $R_c$;

$R_{g\text{-}n}$ is cyano; nitro; $C_1$-$C_6$alkyl; halo-$C_1$-$C_6$alkyl; $C_1$-$C_6$alkoxy-$C_1$-$C_6$alkyl; $C_2$-$C_6$alkenyl; halo-$C_2$-$C_6$alkenyl; $C_2$-$C_6$alkynyl; halo-$C_2$-$C_6$alkynyl; $C_3$-$C_6$cycloalkyl; halo-$C_3$-$C_6$cycloalkyl; $C_1$-$C_6$alkoxy; halo-$C_1$-$C_6$alkoxy; $C_3$-$C_6$cycloalkoxy; $C_1$-$C_6$alkylthio, halo-$C_1$-$C_6$alkylthio; $C_1$-$C_6$alkylsulfinyl; halo-$C_1$-$C_6$alkylsulfinyl; $C_1$-$C_6$alkylsulfonyl; halo-$C_1$-$C_6$alkylsulfonyl; amino; $C_1$-$C_6$alkylamino; halo-$C_1$-$C_6$alkylamino; di-$C_1$-$C_6$alkylamino, in which the two alkyl groups are the same or different or, taken together, form, together with the nitrogen atom, to which they are attached, a ring containing 1 ring nitrogen atom and 2 to 12 ring carbon atoms and optionally 1 further ring hetero atom, which then replaces 1 ring carbon atom and is selected from the group, consisting of an oxygen, a sulfur and a nitrogen atom, which ring is unsubstituted or substituted independently by 1 to 4 substituents, selected from the group, consisting of cyano, nitro, halogen, $C_1$-$C_4$alkyl and $C_1$-$C_4$alkoxy; di-(halo-$C_1$-$C_6$alkyl)-amino, in which the two haloalkyl groups are the same or different; $C_3$-$C_6$cycloalkylamino; N—($C_1$-$C_6$alkyl)-N—($C_3$-$C_6$cycloalkyl)-amino; $C_1$-$C_6$alkoxycarbonyl; halo-$C_1$-$C_6$alkoxycarbonyl; aminocarbonyl; $C_1$-$C_6$alkylaminocarbonyl; halo-$C_1$-$C_6$alkylaminocarbonyl; di-$C_1$-$C_6$alkylaminocarbonyl, in which the two alkyl groups are the same or different or, taken together, form, together with the nitrogen atom, to which they are attached, a ring containing 1 ring nitrogen atom and 2 to 12 ring carbon atoms and optionally 1 further ring hetero atom, which then replaces 1 ring carbon atom and is selected from the group, consisting of an oxygen, a sulfur and a nitrogen atom, which ring is unsubstituted or substituted independently by 1 to 4 substituents, selected from the group, consisting of cyano, nitro, halogen, $C_1$-$C_4$alkyl and $C_1$-$C_4$alkoxy; di-(halo-$C_1$-$C_6$alkyl)-aminocarbonyl, in which the two haloalkyl groups are the same or different; $C_1$-$C_6$alkylcarbonyl; halo-$C_1$-$C_6$alkylcarbonyl; tri-$C_1$-$C_6$alkylsilyl, in which the three alkyl groups are the same or different; or a phenyl, benzyl, benzoyl, phenoxy or monocyclic or bicyclic heteroaryl group, which group is unsubstituted or substituted independently by 1 to 4 substituents, selected from the group, consisting of the substituents $R_a$;

in which formulae Id, Ie and If either k is 0; p is 0; and $G_6$ is a group C(=O); a group C(=S); an oxygen atom; a sulfur atom; a group S(=O); or a group S(=O)$_2$; or k is 0; p is 1; and $G_6$ is a nitrogen atom; or k is 1; p is 1; and $G_6$ is a carbon atom; either l is 0; q is 0; and $G_7$ is a group C(=O); a group C(=S); an oxygen atom; a sulfur atom; a group S(=O); or a group S(=O)$_2$; or l is 0; q is 1; and $G_7$ is a nitrogen atom; or l is 1; q is 1; and $G_7$ is a carbon atom; and either m is 0; r is 0; and $G_8$ is a group C(=O); a group C(=S); an oxygen atom; a sulfur atom; a group S(=O); or a group S(=O)$_2$; or m is 0; r is 1; and $G_8$ is a nitrogen atom; or m is 1; r is 1; and $G_8$ is a carbon atom;

in which formulae Id and Ie either n is 0; s is 0; and $G_9$ is a group C(=O); a group C(=S); an oxygen atom; a sulfur atom; a group S(=O); or a group S(=O)$_2$; or n is 0; s is 1; and $G_9$ is a nitrogen atom; or n is 1; s is 1; and $G_9$ is a carbon atom;

in which formula Id either o is 0; t is 0; and $G_{10}$ is a group C(=O); a group C(=S); an oxygen atom; a sulfur atom; a group S(=O); or a group S(=O)$_2$; or o is 0; t is 1; and $G_{10}$ is a nitrogen atom; or o is 1; t is 1; and $G_{10}$ is a carbon atom;

in which formulae Id, Ie and If the atoms $G_6$ and $G_7$ can be connected by one additional bond, which bond, if present, is represented by a first substituent, which is $R_{62}$, if $G_6$ is a nitrogen atom, and which is $R_{61}$ or $R_{62}$, if $G_6$ is a carbon atom, and a second substituent, which is $R_{72}$, if $G_7$ is a nitrogen atom, and which is $R_{71}$ or $R_{72}$, if $G_7$ is a carbon atom, taken together;

in which formulae Id, Ie and If the atoms $G_7$ and $G_8$ can be connected by one additional bond, which bond, if present, is represented by a first substituent, which is $R_{72}$, if $G_7$ is a nitrogen atom, and which is $R_{71}$ or $R_{72}$, if $G_7$ is a carbon atom, and a second substituent, which is $R_{82}$, if $G_8$ is a nitrogen atom, and which is $R_{81}$ or $R_{82}$, if $G_8$ is a carbon atom, taken together;

in which formulae Id and Ie the atoms $G_8$ and $G_9$ can be connected by one additional bond, which bond, if present, is represented by a first substituent, which is $R_{82}$, if $G_8$ is a nitrogen atom, and which is $R_{81}$ or $R_{82}$, if $G_8$ is a carbon atom, and a second substituent, which is $R_{92}$, if $G_9$ is a nitrogen atom, and which is $R_{91}$ or $R_{92}$, if $G_9$ is a carbon atom, taken together;

in which formula Id the atoms $G_9$ and $G_{10}$ can be connected by one additional bond, which bond, if present, is represented by a first substituent, which is $R_{92}$, if $G_9$ is a nitrogen atom, and which is $R_{91}$ or $R_{92}$, if $G_9$ is a carbon atom, and a second substituent, which is $R_{102}$, if $G_{10}$ is a nitrogen atom, and which is $R_{101}$ or $R_{102}$, if $G_{10}$ is a carbon atom, taken together;

in which formulae Id, Ie and If the atom $G_6$ can be connected either with the atom $G_1$, shown in the formulae Ia, Ib and Ic, by one additional bond, which bond, if present, is represented by a first substituent, which is $R_{62}$, if $G_6$ is a nitrogen atom, and which is $R_{61}$ or $R_{62}$, if $G_6$ is a carbon atom, and a second substituent, which is $R_{12}$, if $G_1$ is a nitrogen atom, and which is $R_{11}$ or $R_{12}$, if $G_1$ is a carbon atom, taken together;

or with the atom $G_2$, shown in the formulae Ia, Ib and Ic, by one additional bond, which bond, if present, is represented by a first substituent, which is $R_{62}$, if $G_6$ is a nitrogen atom, and which is $R_{61}$ or $R_{62}$, if $G_6$ is a carbon atom, and a second substituent, which is $R_{22}$, if $G_2$ is a nitrogen atom, and which is $R_{21}$ or $R_{22}$, if $G_2$ is a carbon atom, taken together;

or with the atom $G_3$, shown in the formulae Ia and Ib, by one additional bond, which bond, if present, is represented by a first substituent, which is $R_{62}$, if $G_6$ is a nitrogen atom, and which is $R_{61}$ or $R_{62}$, if $G_6$ is a carbon atom, and a second substituent, which is $R_{32}$, if $G_3$ is a nitrogen atom, and which is $R_{31}$ or $R_{32}$, if $G_3$ is a carbon atom, taken together;

or with the atom $G_4$, shown in the formula Ia, by one additional bond, which bond, if present, is represented by a first substituent, which is $R_{62}$, if $G_6$ is a nitrogen atom, and which is $R_{61}$ or $R_{62}$, if $G_6$ is a carbon atom, and a second substituent, which is $R_{42}$, if $G_4$ is a nitrogen atom, and which is $R_{41}$ or $R_{42}$, if $G_4$ is a carbon atom, taken together;

in which formula Id the atom $G_{10}$ can be connected either with the atom $G_2$, shown in the formulae Ia, Ib and Ic, by one additional bond, which bond, if present, is represented by a first substituent, which is $R_{102}$, if $G_{10}$ is a nitrogen atom, and which is $R_{101}$ or $R_{102}$, if $G_{10}$ is a carbon atom, and a second substituent, which is $R_{22}$, if $G_2$ is a nitrogen atom, and which is $R_{21}$ or $R_{22}$, if $G_2$ is a carbon atom, taken together;

or with the atom $G_3$, shown in the formulae Ia, Ib and Ic, by one additional bond, which bond, if present, is represented by a first substituent, which is $R_{102}$, if $G_{10}$ is a nitrogen atom, and which is $R_{101}$ or $R_{102}$, if $G_{10}$ is a carbon atom, and a second substituent, which is $R_{32}$, if $G_3$ is a nitrogen atom, and which is $R_{31}$ or $R_{32}$, if $G_3$ is a carbon atom, taken together;

or with the atom $G_4$, shown in the formulae Ia and Ib, by one additional bond, which bond, if present, is represented by a first substituent, which is $R_{102}$, if $G_{10}$ is a nitrogen atom, and which is $R_{101}$ or $R_{102}$, if $G_{10}$ is a carbon atom, and a second substituent, which is $R_{42}$, if $G_4$ is a nitrogen atom, and which is $R_{41}$ or $R_{42}$, if $G_4$ is a carbon atom, taken together;

or with the atom $G_5$, shown in the formula Ia, by one additional bond, which bond, if present, is represented by a first substituent, which is $R_{102}$, if $G_{10}$ is a nitrogen atom, and which is $R_{101}$ or $R_{102}$, if $G_{10}$ is a carbon atom, and a second substituent, which is $R_{52}$, if $G_5$ is a nitrogen atom, and which is $R_{51}$ or $R_{52}$, if $G_5$ is a carbon atom, taken together;

in which formula Ie the atom $G_9$ can be connected either with the atom $G_2$, shown in the formulae Ia, Ib and Ic, by one additional bond, which bond, if present, is represented by a first substituent, which is $R_{92}$, if $G_9$ is a nitrogen atom, and which is $R_{91}$ or $R_{92}$, if $G_9$ is a carbon atom, and a second substituent, which is $R_{22}$, if $G_2$ is a nitrogen atom, and which is $R_{21}$ or $R_{22}$, if $G_2$ is a carbon atom, taken together;

or with the atom $G_3$, shown in the formulae Ia, Ib and Ic, by one additional bond, which bond, if present, is represented by a first substituent, which is $R_{92}$, if $G_9$ is a nitrogen atom, and which is $R_{91}$ or $R_{92}$, if $G_9$ is a carbon atom, and a second substituent, which is $R_{32}$, if $G_3$ is a nitrogen atom, and which is $R_{31}$ or $R_{32}$, if $G_3$ is a carbon atom, taken together;

or with the atom $G_4$, shown in the formulae Ia and Ib, by one additional bond, which bond, if present, is represented by a first substituent, which is $R_{92}$, if $G_9$ is a nitrogen atom, and which is $R_{91}$ or $R_{92}$, if $G_9$ is a carbon atom, and a second substituent, which is $R_{42}$, if $G_4$ is a nitrogen atom, and which is $R_{41}$ or $R_{42}$, if $G_4$ is a carbon atom, taken together;

or with the atom $G_5$, shown in the formula Ia, by one additional bond, which bond, if present, is represented by a first substituent, which is $R_{92}$, if $G_9$ is a nitrogen atom, and which is $R_{91}$ or $R_{92}$, if $G_9$ is a carbon atom, and a second substituent, which is $R_{52}$, if $G_5$ is a nitrogen atom, and which is $R_{51}$ or $R_{52}$, if $G_5$ is a carbon atom, taken together;

in which formula If the atom $G_8$ can be connected either with the atom $G_2$, shown in the formulae Ia, Ib and Ic, by one additional bond, which bond, if present, is represented by a first substituent, which is $R_{82}$, if $G_8$ is a nitrogen atom, and which is $R_{81}$ or $R_{82}$, if $G_8$ is a carbon atom, and a second substituent, which is $R_{22}$, if $G_2$ is a nitrogen atom, and which is $R_{21}$ or $R_{22}$, if $G_2$ is a carbon atom, taken together;

or with the atom $G_3$, shown in the formulae Ia, Ib and Ic, by one additional bond, which bond, if present, is represented by a first substituent, which is $R_{82}$, if $G_8$ is a nitrogen atom, and which is $R_{81}$ or $R_{82}$, if $G_8$ is a carbon atom, and a second substituent, which is $R_{32}$, if $G_3$ is a nitrogen atom, and which is $R_{31}$ or $R_{32}$, if $G_3$ is a carbon atom, taken together;

or with the atom $G_4$, shown in the formulae Ia and Ib, by one additional bond, which bond, if present, is represented by a first substituent, which is $R_{82}$, if $G_8$ is a nitrogen atom, and which is $R_{81}$ or $R_{82}$, if $G_8$ is a carbon atom, and a second substituent, which is $R_{42}$, if $G_4$ is a nitrogen atom, and which is $R_{41}$ or $R_{42}$, if $G_4$ is a carbon atom, taken together;

or with the atom $G_5$, shown in the formula Ia, by one additional bond, which bond, if present, is represented by a first substituent, which is $R_{82}$, if $G_8$ is a nitrogen atom, and which is $R_{81}$ or $R_{82}$, if $G_8$ is a carbon atom, and a second substituent, which is $R_{52}$, if $G_5$ is a nitrogen atom, and which is $R_{51}$ or $R_{52}$, if $G_5$ is a carbon atom, taken together;

in which formula Id each of those substituents, selected from the group, consisting of the substituents $R_{61}$, $R_{62}$, $R_{71}$, $R_{72}$, $R_{81}$, $R_{82}$, $R_{91}$, $R_{92}$, $R_{101}$, and $R_{102}$, which are different from any first substituent, if present, as defined hereinbefore for the formula Id, and from any second substituent, if present, as defined hereinbefore for the formula Id, is independently selected from the group, consisting of the substituents $R_h$;

in which formula Ie each of those substituents, selected from the group, consisting of the substituents $R_{61}$, $R_{62}$, $R_{71}$, $R_{72}$, $R_{81}$, $R_{82}$, $R_{91}$ and $R_{92}$, which are different from any first substituent, if present, as defined hereinbefore for the formula Ie, and from any second substituent, if present, as defined hereinbefore for the formula Ie, is independently selected from the group, consisting of the substituents $R_i$;

in which formula If each of those substituents, selected from the group, consisting of the substituents $R_{61}$, $R_{62}$, $R_{71}$, $R_{72}$, $R_{81}$ and $R_{82}$, which are different from any first substituent, if present, as defined hereinbefore for the formula If, and from any second substituent, if present, as defined hereinbefore for the formula If, is independently selected from the group, consisting of the substituents $R_h$;

$R_h$ is hydrogen; or a substituent $R_j$; the total number of the substituents $R_j$, if present, having an upper limit of 6 for a group of the formula Id; and of 4 for a group of the formula If; which total number can, however, be limited for a specific group of the formula Id or If to a value lower than the upper limit mentioned hereinbefore, which value is then equal to the number of the positions available for the substitution by a substituent $R_j$ in this specific group;

$R_i$ is hydrogen; or a substituent $R_k$; the total number of the substituents $R_k$, if present, having an upper limit of 5;

which total number can, however, be limited for a specific group of the formula Ie to a value lower than the upper limit mentioned hereinbefore, which value is then equal to the number of the positions available for the substitution by a substituent $R_k$ in this specific group;

$R_j$ is either attached to a carbon atom and then selected from the group, consisting of the substituents $R_{j-c}$; or attached to a nitrogen atom and then selected from the group, consisting of the substituents $R_{j-n}$;

$R_{j-c}$ is a substituent $R_c$;

$R_{j-n}$ is a substituent $R_{g-n}$;

$R_k$ is either attached to a carbon atom and then selected from the group, consisting of the substituents $R_{k-c}$; or attached to a nitrogen atom and then selected from the group, consisting of the substituents $R_{k-n}$;

or 2 substituents $R_k$, the first of which is attached to the atom $G_6$ and is represented by $R_{62}$, if $G_6$ is a nitrogen atom, and by $R_{61}$ or $R_{62}$, if $G_6$ is a carbon atom, and the second of which is attached to the atom $G_9$ and is represented by $R_{92}$, if $G_9$ is a nitrogen atom, and by $R_{91}$ or $R_{92}$, if $G_9$ is a carbon atom, taken together, are —$CH_2$—; or —O—;

$R_{k-c}$ is a substituent $R_c$;

$R_{k-n}$ is a substituent $R_{g-n}$;

$R_8$ is hydrogen; $C_1$-$C_6$alkyl; or halo-$C_1$-$C_6$alkyl; or has one of the meanings defined hereinbefore or hereinafter;

or $R_5$ and $R_8$, taken together, are a bond;

with the proviso, that (i) a ring oxygen atom, if present, is not directly connected with a further ring oxygen atom, if any;

(ii) a ring carbon atom, selected from the group, consisting of $G_1$, $G_2$, $G_3$, $G_4$, $G_5$, $G_6$, $G_7$, $G_8$, $G_9$ and $G_{10}$, is, if present, not directly connected with any other atom by a triple bond or with any other 2 different atoms by 2 double bonds;

(iii) not more than 6 of the variables $G_1$, $G_2$, $G_3$, $G_4$, $G_5$, $G_6$, $G_7$, $G_8$, $G_9$ and $G_{10}$ can, if present, be selected from the group, consisting of an oxygen atom, a sulfur atom, a group S(=O), a group S(=O)$_2$ and a nitrogen atom, each of the remaining of these variables, if any, being selected from the group, consisting of a carbon atom, a group C(=O) and a group C(=S), and not more than 3 of the said 6 variables can be selected from the group, consisting of an oxygen atom, a sulfur atom, a group S(=O) and a group S(=O)$_2$; and (iv) unless otherwise defined hereinbefore, the meaning of a variable at a certain occurrence can be selected independently from the meaning of the same variable at any other occurrence, if any.

Unless otherwise defined, the general terms used hereinabove and hereinbelow have the meanings which follow.

Halogen—as a group per se and as a structural element of other groups and compounds, such as haloalkyl—is, for example, fluorine, chlorine, bromine or iodine, in particular fluorine, chlorine or bromine, but especially chlorine or bromine.

Unless otherwise defined, carbon-containing groups and compounds comprise for example in each case 1 up to and including 15, preferably 1 up to and including 10, especially 1 up to and including 8, in particular 1 up to and including 5, especially 1 or 2, carbon atom(s).

Cycloalkyl—as a group per se and as a structural element of other groups and compounds, such as halocycloalkyl—is, in each case with due consideration of the number of carbon atoms contained in each case in the relevant group or compound, for example cyclopropyl, cyclobutyl, cyclopentyl or cyclohexyl.

Alkyl—as a group per se and as a structural element of other groups and compounds, such as haloalkyl—is, in each case with due consideration of the number of carbon atoms contained in each case in the relevant group or compound, either straight-chain, for example methyl, ethyl, propyl, butyl, pentyl or hexyl, or branched, for example isopropyl, isobutyl, sec-butyl, tert-butyl, isopentyl, neopentyl or isohexyl.

Alkenyl—as a group per se and as a structural element of other groups and compounds, such as haloalkenyl—is, in each case with due consideration of the number of carbon atoms contained in each case in the relevant group or compound, either straight-chain or branched and comprises in each case 2 or more than 2 or preferably 1 carbon-carbon double bond(s), the double bonds of these substituents being separated from the remaining moiety of the compound I by preferably at least one saturated carbon atom, and is, for example, allyl, propen-2-yl, methallyl, but-2-en-1-yl, but-3-en-1-yl or pent-4-en-1-yl.

Alkynyl—as a group per se and as a structural element of other groups and compounds, such as haloalkynyl—is, in each case with due consideration of the number of carbon atoms contained in each case in the relevant group or compound, either straight-chain or branched and comprises in each case 2 or more than 2 or preferably 1 carbon-carbon triple bond(s), the triple bonds of these substituents being separated from the remaining moiety of the compound I by preferably at least one saturated carbon atom, and is, for example, propargyl, but-2-ynyl or but-3-yn-2-yl.

Aryl is, for example, naphthyl or, preferably, phenyl.

Heteroaryl has, for example, an aromatic ring skeleton composed of a ring having 5 or 6 ring members or of a combination of at least two rings having in each case independently of one another 5 or 6 ring members, where for example 1 up to and including 4 of the ring members is (are) (a) heteroatom(s) selected from the group consisting of nitrogen, oxygen and sulfur, and is, for example, pyridyl, thienyl, pyrazolyl, thiazolyl, thiadiazolyl, furyl, oxadiazolyl, indolizinyl, pyrimidyl, quinolyl or pteridinyl.

Non-aromatic heterocyclyl has, for example, a non-aromatic ring skeleton composed of a ring having 5 or 6 ring members or of a combination of at least two rings having in each case independently of one another 5 or 6 ring members, where for example 1 up to and including 4 of the ring members is (are) (a) heteroatom(s) selected from the group consisting of nitrogen, oxygen and sulfur and is, for example, piperidyl, pyrrolinyl, tetrahydrofuryl or chromanyl.

Halogen-substituted carbon-containing groups and compounds, such as haloalkyl, can be partially halogenated or perhalogenated, where, in the case of polyhalogenation, the halogen substituents can be identical or different.

The following are further preferred embodiments within the scope of the invention:

(3) A compound according to (1) or (2) of the formula I, in which $Z_1$ is an oxygen atom;

(4) A compound according to any one of (1) to (3) of the formula I, in which $Z_2$ is an oxygen atom;

(5) A compound according to any one of (1) to (4) of the formula I, in which $R_1$ is a phenyl, pyridyl or pyrazolyl group, which is unsubstituted or preferably substituted;

especially a phenyl, pyridyl or pyrazolyl group, which is substituted independently by 1 to 3 substituents, selected from the group, consisting of halogen, $C_1$-$C_6$alkyl, halo-$C_1$-$C_6$alkyl, $C_1$-$C_6$alkoxy, halo-$C_1$-$C_6$alkoxy and a phenyl or pyridyl group, which group is unsubstituted or preferably substituted;

more especially a phenyl, pyridyl or pyrazolyl group, which is substituted independently by 1 to 3 substituents, selected from the group, consisting of halogen, $C_1$-$C_6$alkyl, halo-$C_1$-$C_6$alkyl, halo-$C_1$-$C_6$alkoxy and a phenyl or pyridyl group, which group is substituted independently by 1 to 3 substituents, selected from the group, consisting of halogen and $C_1$-$C_6$alkyl;

preferably a phenyl or pyridyl group, which is substituted independently by 1 to 3 substituents, selected from the group, consisting of $C_1$-$C_6$alkyl and halo-$C_1$-$C_6$alkyl; or a pyrazolyl group, which is substituted independently by 1 to 3 substituents, selected from the group, consisting of halogen, $C_1$-$C_6$alkyl, halo-$C_1$-$C_6$alkyl, halo-$C_1$-$C_6$alkoxy and a phenyl or pyridyl group, which group is substituted independently by 1 to 3 substituents, selected from the group, consisting of halogen and $C_1$-$C_6$alkyl;

more preferably a pyrazolyl group, which is substituted independently by 1 to 3 substituents, selected from the group, consisting of halogen, $C_1$-$C_6$alkyl, halo-$C_1$-$C_6$alkyl, halo-$C_1$-$C_6$alkoxy and a phenyl or pyridyl group, which group is substituted independently by 1 to 3 substituents, selected from the group, consisting of halogen and $C_1$-$C_6$alkyl;

especially a pyrazol-3-yl group, which is substituted independently by 1 to 3 substituents, selected from the group, consisting of halogen, $C_1$-$C_6$alkyl, halo-$C_1$-$C_6$alkyl, halo-$C_1$-$C_6$alkoxy and a phenyl or pyridyl group, which group is substituted independently by 1 to 3 substituents, selected from the group, consisting of halogen and $C_1$-$C_6$alkyl;

more especially a pyrazol-3-yl group, which is substituted independently by 1 to 3 substituents, selected from the group, consisting of halogen, halo-$C_1$-$C_6$alkyl, halo-$C_1$-$C_6$alkoxy and a phenyl or pyridyl group, which group is substituted independently by 1 to 3 substituents, selected from the group, consisting of halogen and $C_1$-$C_6$alkyl;

preferably a pyrazol-3-yl group, which is substituted independently by 1 to 3 substituents, selected from the group, consisting of halogen, halo-$C_1$-$C_6$alkyl, halo-$C_1$-$C_6$alkoxy and a pyridyl group, which group is substituted independently by 1 to 3 substituents, selected from the group, consisting of halogen;

more preferably a pyrazol-3-yl group, which is substituted independently by 1 to 3 substituents, selected from the group, consisting of halogen, halo-$C_1$-$C_6$alkyl, halo-$C_1$-$C_6$alkoxy and a pyrid-2-yl group, which group is substituted independently by 1 or 2 substituents, selected from the group, consisting of halogen;

especially a pyrazol-5-yl group, which is substituted in the 3-position by halogen, halo-$C_1$-$C_6$alkyl or halo-$C_1$-$C_6$alkoxy and in the 1-position by a pyrid-2-yl group, which group is substituted independently by 1 or 2 substituents, selected from the group, consisting of halogen;

more especially a pyrazol-5-yl group, which is substituted in the 3-position by halogen, halo-$C_1$-$C_6$alkyl or halo-$C_1$-$C_6$alkoxy and in the 1-position by a pyrid-2-yl group, which group is substituted in the 3-position by halogen;

preferably a pyrazol-5-yl group, which is substituted in the 3-position by halogen, halo-$C_1$-$C_6$alkyl or halo-$C_1$-$C_6$alkoxy and in the 1-position by a pyrid-2-yl group, which group is substituted in the 3-position by chlorine or bromine;

more preferably a pyrazol-5-yl group, which is substituted in the 3-position by halo-$C_1$-$C_6$alkyl and in the 1-position by a pyrid-2-yl group, which group is substituted in the 3-position by chlorine or bromine;

most preferably a pyrazol-5-yl group, which is substituted in the 3-position by trifluoromethyl and in the 1-position by a pyrid-2-yl group, which group is substituted in the 3-position by chlorine or bromine;

(6) A compound according to any one of (1) to (5) of the formula I, in which $R_2$ is hydrogen or $C_1$-$C_6$alkyl; preferably hydrogen;

(7) A compound according to any one of (1) to (6) of the formula I, in which $R_3$ is hydrogen or $C_1$-$C_6$alkyl;

preferably hydrogen;

(8) A compound according to any one of (1) to (7) of the formula I, in which $R_4$ is $C_1$-$C_6$alkyl; preferably methyl or isopropyl;

(9) A compound according to any one of (1) to (8) of the formula I, in which $R_5$ and $R_8$, taken together, are a bond;

(10) A compound according to any one of (1) to (9) of the formula I, in which $R_6$ and $R_7$, taken together, are a group of the formula Ib or a group of the formula Ic;

(11) A compound according to any one of (1) to (10) of the formula I, in which the two carbon atoms, shown in the formula I, to which atoms $R_6$ and $R_7$ are attached, are two ring members of an aromatic ring;

(12) A compound according to any one of (1) to (11) of the formula I, in which $R_6$ and $R_7$, taken together, form, together with the two carbon atoms, shown in the formula I, to which atoms they are attached, and together with $R_5$ and with $R_8$, one of the bicyclic ring systems shown in the formulae T1 to T85, or shown in the formulae T1 to T71, each of which ring systems is substituted by the two substituents —N($R_2$)—C(=$Z_1$)—$R_1$ and —C(=$Z_2$)—N($R_3$)—$R_4$;

preferably taken together, form, together with the two carbon atoms, shown in the formula I, to which atoms they are attached, and together with $R_5$ and with $R_8$, one of the bicyclic ring systems shown in the formulae T1, T6, T7, T21, T37 and T38, each of which ring systems is substituted by the two substituents —N($R_2$)—C(=$Z_1$)—R, and —C(=$Z_2$)—N($R_3$)—$R_4$;

more preferably taken together, form, together with the two carbon atoms, shown in the formula I, to which atoms they are attached, and together with $R_5$ and with $R_8$, one of the bicyclic ring systems shown in the formulae T1 and T7, or shown in the formulae T2, T22, T75, T76, T78, T79 and T81, each of which ring systems is substituted by the two substituents —N($R_2$)—C(=$Z_1$)—R, and —C(=$Z_2$)—N($R_3$)—$R_4$.

A further preferred subgroup of the compounds of formula I is represented by the compounds of formulae VIIa and VIIb

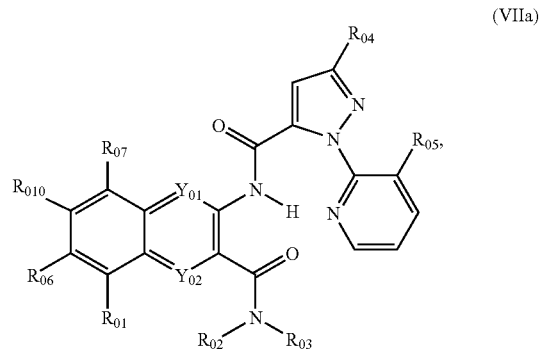

(VIIa)

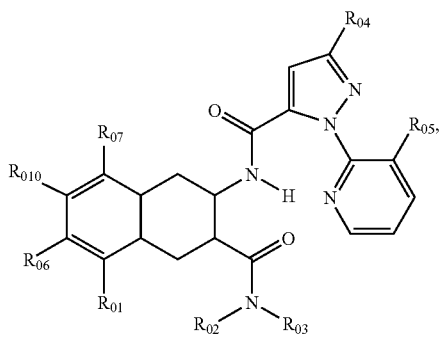

(VIIb)

wherein
$R_{01}$ is hydrogen; amino or nitro;
$R_{02}$ is hydrogen or $C_1$-$C_4$alkyl;
$R_{03}$ is $C_1$-$C_4$alkyl, $C_1$-$C_4$alkyl mono- or disubstituted by cyano, COOH, nitro, $C_1$-$C_4$alkoxy or cyclopropyl;
$C_2$-$C_8$alkenyl, $C_2$-$C_8$alkenyl substituted by halogen;
$C_1$-$C_4$alkoxy, $C_3$-$C_6$-alkinyl, cyclopropyl, cyclobutyl, cyclopentyl, cyclohexyl, cyclopropyl substituted by $C_1$-$C_4$alkyl, pyridyl, phenyl-$C_2$-$C_6$alkenyl or cyclopropyl;
cyclobutyl substituted by $C_1$-$C_4$alkyl;
cyclopentylthio-$C_1$-$C_4$alkyl, benzyloxy, benzyloxy substituted by halogen;
benzylthio-$C_1$-$C_4$alkyl, wherein the benzyl group may itself be substituted by $C_1$-$C_4$alkyl;
thiophenyl substituted by halophenyl;
phenoxy-$C_1$-$C_4$alkyl, wherein the phenyl group may be mono- or disubstituted by halogen;
phenyl-$C_1$-$C_4$alkyl, wherein the phenyl group may itself be mono- or disubstituted by substituents selected from halogen, nitro, benzothiazol-2-yloxy, $C_1$-$C_4$haloalkyl, $C_1$-$C_4$alkoxy and $C_1$-$C_4$alkyl;
3,4-dihydro-2H-benzo[b][1,4]dioxepinyl, 1,2,3,4-tetrahydro-naphthalenyl substituted by $C_1$-$C_4$alkoxy;
$C_2$-$C_6$alkenyloxy, isoxazolyl substituted by $C_1$-$C_4$alkyl;
thiazolyl, $C_1$-$C_4$alkoxycarbonyl-$C_1$-$C_4$alkyl, phenyl substituted by hydroxy, halophenyloxy, $C_1$-$C_4$alkyl-silyl($C_1$-$C_4$-alkyl)$_3$ or $C_2$-$C_6$alkinyl;
pyridyl substituted by $C_1$-$C_4$alkoxy;
$C_1$-$C_6$alkylthio-$C_1$-$C_4$alkyl, $C_2$-$C_6$alkenylthio-$C_1$-$C_4$alkyl, $C_3$-$C_6$alkinylthio-$C_1$-$C_4$alkyl, dioxolan-2-yl-$C_1$-$C_4$alkyl, ($C_1$-$C_4$alkyl-dioxolan-2-yl)-$C_1$-$C_4$alkyl, triazolyl-$C_1$-$C_4$alkyl, thienyl-$C_1$-$C_4$alkyl, morpholinyl-$C_1$-$C_4$alkyl, $C_1$-$C_4$alkylthio-$C_1$-$C_4$alkyl, 2,3-dihydro-1H-isoindolyl, halo-substituted-thiazolyl-$C_1$-$C_4$alkyl,
$C_1$-$C_4$alkylsulfonyl-$C_1$-$C_4$alkyl or quinolylthio-$C_1$-$C_4$alkyl, wherein the quinoline group may be substituted by $C_1$-$C_4$haloalkyl;
$R_{04}$ is $C_1$-$C_4$haloalkyl;
$R_{05}$ is halogen;
each of $R_{06}$ and $R_{010}$, which may be the same or different, represents hydrogen, $C_1$-$C_6$alkyl, $C_1$-$C_6$alkoxycarbonyloxy, $C_1$-$C_6$alkylcarbonylamino, hydroxy, cyano, halogen or $C_1$-$C_6$lkoxy;
$R_{07}$ is hydrogen, nitro or halogen;
$Y_{01}$ is $C(R_{08})$, sulfur, nitrogen or a chemical bond;
$R_{08}$ is hydrogen, halogen, $C_1$-$C_4$alkyl or nitro;
$Y_{02}$ is $C(R_{09})$, a chemical bond, or is nitrogen or sulfur; and $R_{09}$ is hydrogen, phenyl, phenyl substituted by halogen, or halogen.

Preferred compounds of the formula VIIa are those, wherein
$R_{01}$ is hydrogen; $R_{02}$ is hydrogen; $R_{03}$ is $C_1$-$C_4$alkyl, preferably methyl; $R_{04}$ is $C_1$-$C_4$fluoroalkyl, preferably trifluoromethyl; $R_{05}$ is chloro; $R_{06}$ is halogen, preferably chloro; $R_{07}$ is hydrogen;
$R_{010}$ is hydrogen; $Y_{01}$ is $C(R_{08})$; $R_{08}$ is halogen, preferably chloro; $Y_{02}$ is $C(R_{09})$, and $R_{09}$ is hydrogen.

Especially preferred within the scope of the invention are the compounds of the formula I mentioned in the Examples P3, P6 and P9 to P11.

Individually preferred within the scope of the invention is each of the compounds T1.1, T1.3, T6.1, T6.3, T7.1, T7.3, T21.3, T37.3 and T38.3.

Also individually preferred within the scope of the invention is each of the compounds T2.1, T22.3, T75.1, T75.3, T76.1, T76.3, T78.1, T79.1 and T81.1.

The process according to the invention for preparing compounds of the formula I is carried out analogously to known processes. In the section that follows, the substituents $R_1$, $R_2$, $R_3$, $R_4$, $R_5$, $R_6$, $R_7$, $R_8$, $Z_1$ and $Z_2$ are as defined under formula I in claim 1 unless otherwise stated.

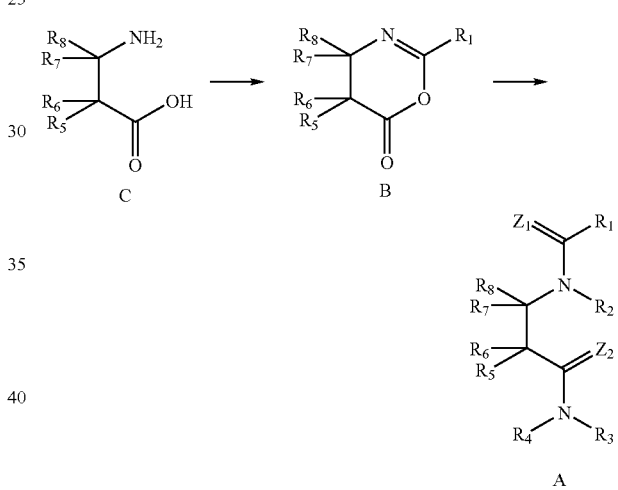

Compounds of formula A, wherein $Z_1$ and $Z_1$ are oxygen and $R_1$ is hydrogen, may be made from the ring opening of a benzoxazinone of formula B with an amine of formula $NHR_3R_4$. Such amines are either known or they may be made analogously to known processes. Benzoxazinones of formula B may be made from amino acids of formula C by treatment with a carboxylic acid of formula $R_1$—COOH and a dehydrating reagent such as methanesulfonyl chloride (optionally in the presence of a base such as pyridine or triethylamine). Alternatively benzoxazinones of formula B may be obtained by the treatment of amino acids of formula C with an acid chloride of formula $R_1$—COCl under basic conditions (for example in pyridine), followed if necessary by a second cyclisation step (which may be achieved using a dehydrating agent for example acetic anhydride). Acid chlorides of formula $R_1$—COCl may be made from carboxylic acids of formula $R_1$—COOH under standard conditions (for example by treatment with thionyl chloride or oxalyl chloride). Carboxylic acids of formula $R_1$—COOH are either known compounds or they may be made analogously to known processes.

Compounds of formula A, wherein $Z_1$ and $Z_1$ are sulfur, may be made from compounds of formula A, wherein $Z_1$ and $Z_2$ are oxygen, by treatment with a thio-transfer reagent such as Lawesson's reagent or phosphorus pentasulfide.

$C_1$-$C_4$alkoxy, may be made from compounds of formula C by sequential treatment with an alcohol under acidic conditions

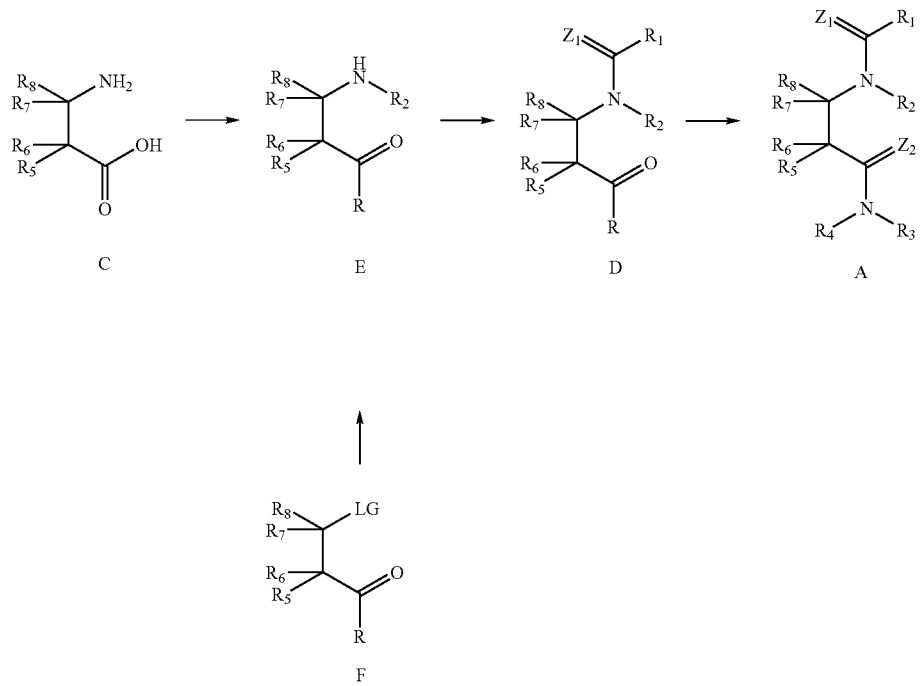

Alternatively, compounds of formula A, wherein $Z_1$ and $Z_1$ are oxygen, may be made by treatment of compounds of formula D, wherein $Z_1$ is oxygen and R is OH, $C_1$-$C_4$alkoxy or Cl, with an amine of formula $NHR_3R_4$. The standard conditions for such acylation reactions are as follows: when R is OH such reactions are usually carried out in the presence of a coupling reagent such as DCC (N,N'-dicyclohexylcarbodiimide) or EDC (1-Ethyl-3-[3-dimethylamino-propyl]carbodiimide hydrochloride) optionally in the presence of a nucleophilic catalyst such as hydroxybenzotriazole or 4-(dimethylamino)-pyridine. When R is Cl, such reactions are usually carried out under basic conditions (for example in the presence of pyridine or triethylamine), again optionally in the presence of a nucleophilic catalyst. It may be possible to convert esters (wherein R is $C_1$-$C_4$alkoxy) directly to amides by heating the ester and amine together in a thermal process.

Acid chlorides of formula D, wherein $Z_1$ is oxygen and R is Cl, may be made from carboxylic acids of formula D, wherein $Z_1$ is oxygen and R is OH, under standard conditions (such as treatment with thionyl chloride or oxalyl chloride). Carboxylic acids of formula D, wherein $Z_1$ is oxygen and R is OH, may be formed from esters of formula D, wherein $Z_1$ is oxygen and R is $C_1$-$C_4$alkoxy. It is well known for a person skilled in the art that there are many methods for the hydrolysis of such esters depending on the nature of the alkoxy group. One widely used method to achieve such a transformation is the treatment of the ester with an alkali such as sodium hydroxide in a solvent such as ethanol.

Esters of formula D, wherein $Z_1$ is oxygen and R is $C_1$-$C_4$alkoxy, may be made by treatment of compounds of formula E, wherein R is $C_1$-$C_4$alkoxy, by acylation with compounds of formula $R_1$—COOH or $R_1$—COCl under standard conditions as previously described. Compounds of formula E, wherein R is and then formation of the N—$R_2$ bond. It is known to a person skilled in the art that there are many reported methods for the formation of this bond depending on the nature of the substituent $R_2$. For example, reductive amination may be achieved by treatment of the amine with an aldehyde or ketone and a reducing agent such as sodium cyanoborohydride. Alternatively alkylation may be achieved by treating the amine with an alkylating agent such as an alkyl halide, optionally in the presence of a base. Alternatively arylation may be achieved by treatment of the amine with an aryl halide or sulfonate in the presence of a suitable catalyst/ligand system, often a palladium (0) complex.

Alternatively, compounds of formula E, wherein R is $C_1$-$C_4$alkoxy, may be made from a compound of formula F, wherein R is $C_1$-$C_4$alkoxy and LG is a leaving group such as fluoro, chloro or sulfonate, via nucleophilic displacement of the leaving group by an amine of formula $R_2$—$NH_2$. Such compounds of formula F and amines of formula $R_2$—$NH_2$ are either known compounds or can be made by known methods obvious to someone skilled in the art.

Compounds of formula A, wherein $Z_1$ is sulfur and $Z_2$ is oxygen, can be made from compounds of formula D, wherein $Z_1$ is oxygen and R is OH or $C_1$-$C_4$alkoxy, by treatment with a thio-transfer reagent such as Lawesson's reagent or phosphorus pentasulfide prior to coupling with the amine of formula $NHR_3R_4$.

Alternatively, compounds of formula D, wherein R is OH and $Z_1$ is oxygen, may be dehydrated to benzoxazinones of formula B by treatment with a dehydrating agent such as acetic anhydride.

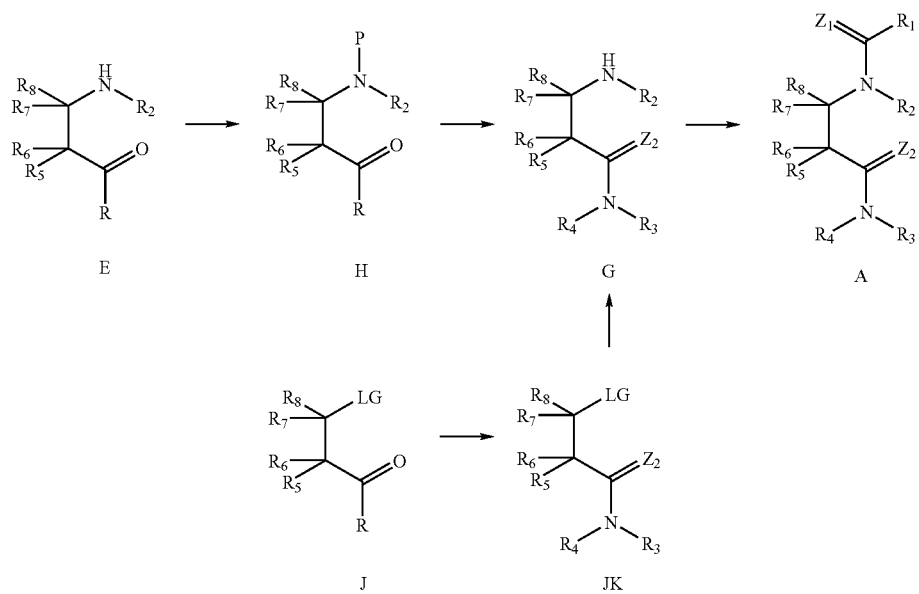

Alternatively, compounds of formula A, wherein $Z_1$ and $Z_2$ are oxygen, may be made by the treatment of compounds of formula G, wherein $Z_2$ is oxygen, with a carboxylic acid of formula $R_1$—COOH or an acid chloride of formula $R_1$—COCl as previously described. Compounds of formula G, wherein $Z_2$ is oxygen, may be formed from compounds of formula H, wherein P is a suitable protecting group and R is OH, Cl or $C_1$-$C_4$alkoxy, by amide bond formation with an amine of formula $NHR_2R_3$ as previously described for compounds of formula D, followed by removal of the protecting group P under standard conditions. Compounds of formula H, wherein R is OH or $C_1$-$C_4$alkoxy, may be made by the protection of the amine functionality in compounds of formula E, wherein R is OH or $C_1$-$C_4$alkoxy. Suitable protecting groups include carbamates (such as t-butyloxycarbonyl, allyloxycarbonyl and benzyloxycarbonyl), trialkylsilyl groups (such as t-butyldimethylsilyl) and acyl groups (such as acetyl). The formation and removal of such groups is widely reported in the literature and is well known to a person skilled in the art.

For compounds of formula H and compounds of formula E, the esters (wherein R is $C_1$-$C_4$alkoxy) may be hydrolysed to the acids (wherein R is OH) by treatment with an alkali such as sodium hydroxide in a solvent such as ethanol. The acids (wherein R is OH) may be converted to the acid chlorides (wherein R is Cl) by treatment with thionyl chloride or oxalyl chloride as previously described for compounds of formula D.

Alternatively, it may be possible to convert compounds of formula E, wherein R is OH, Cl or $C_1$-$C_4$alkoxy, directly to compounds of formula G by amide bond formation with an amine of formula $NHR_3R_4$ under standard conditions (as previously described for compounds of formula D).

Alternatively, compounds of formula G, wherein $Z_2$ is oxygen, may be made from compounds of formula JK, wherein $Z_2$ is oxygen and LG is a leaving group such as fluoro, chloro or sulfonate, by displacement of the leaving group with a compound of formula $R_2NH_2$. Such reactions are usually performed under basic conditions. Such compounds of formula JK may be made from compounds of formula J, wherein R is Cl or OH and LG is a leaving group as previously described, via amide bond formation under standard conditions as previously described. Such compounds of formula J and formula E are either known compounds or may be made by known methods by someone skilled in the art.

Compounds of formula A, wherein $Z_1$ is oxygen and $Z_2$ is sulfur, may be made by treatment of compounds of formula JK, wherein $Z_2$ is oxygen and LG is a leaving group, or compounds of formula G, wherein $Z_2$2 is oxygen, with a thio-transfer reagent such as Lawesson's reagent or phosphorus pentasulfide prior to elaborating to compounds of formula A, wherein $Z_1$ is oxygen and $Z_2$ is sulfur, as previously described for compounds of formula A, wherein $Z_1$ is oxygen and $Z_2$ is oxygen).

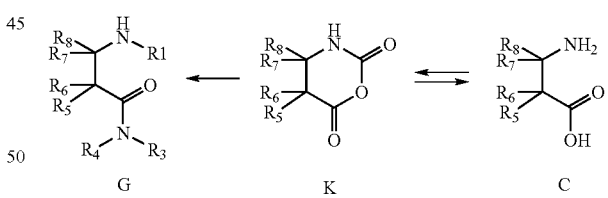

Compounds of formula C are either known or may be made by methods known to a person skilled in the art. For instance, amino acids of formula C may be formed by hydrolysis of isatoic anhydrides of formula K. Alternatively, isatoic anhydrides of formula K may be reacted with amines of formula $NHR_3R_4$ to give compounds of formula G, wherein $R_1$ is H, directly. Isatoic anhydrides of formula K are either known compounds or may be made by known methods obvious to those skilled in the art, for instance they made be derived from treatment of amino acids of formula C with phosgene or a synthetic equivalent of phosgene (for example carbonyl diimidazole).

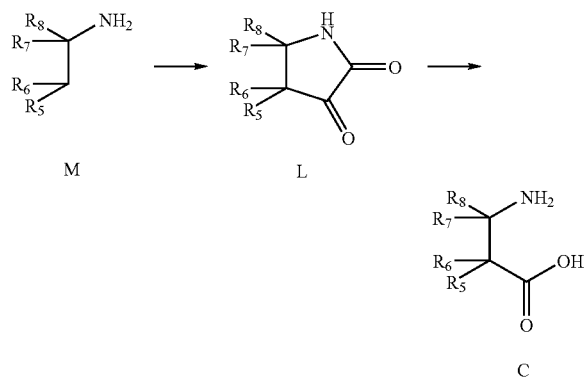

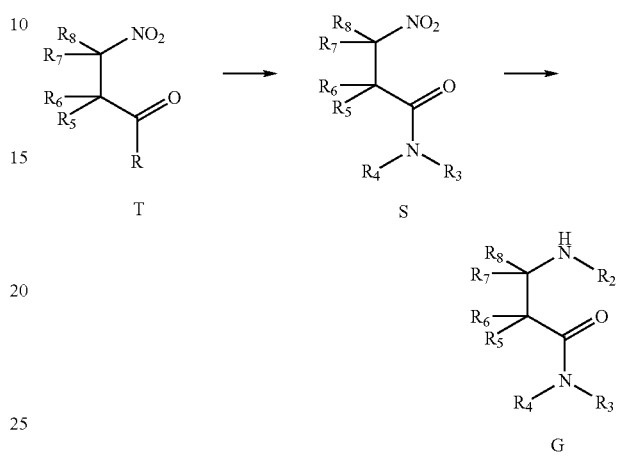

Alternatively, compounds of formula C may be derived from the treatment of an isatin of formula L with hydrogen peroxide under basic conditions. Isatins of formula L are either known or may be made by methods known to persons skilled in the art, for example they may be derived from amino compounds of formula M, wherein $R_5$ and $R_8$ taken together form an additional bond between the carbon atoms bearing substituents $R_6$ and $R_7$, by treatment for example with oxalyl chloride (optionally in the presence of a Lewis acid catalyst) or chloral hydrate under various conditions. Amino compounds of formula M are either known compounds or may be made by known methods obvious to those skilled in the art.

ylformamide dimethylacetal under basic conditions followed by treatment with sodium periodate. Compounds of formula P and Q are either known or may be made by methods known to those skilled in the art, for instance compounds of formula Q may be synthesised from compounds of formula R by nitration (e.g. with a mixture of nitric acid and sulphuric acid).

An alternative synthesis of compounds of formula G, wherein $R_2$ is hydrogen, may be achieved by the reduction of

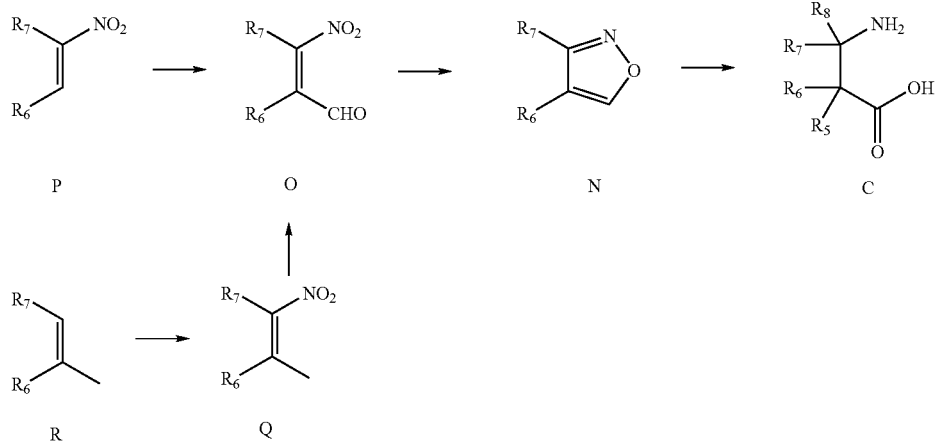

Alternatively, compounds of formula C, wherein $R_5$ and $R_8$ taken together form an additional bond between the carbon atoms bearing substituents $R_6$ and $R_7$, may be derived from the treatment of an isoxazole of formula N with aqueous base. Isoxazoles of formula N may be derived from nitroaldehydes of formula O by treatment with a reducing agent such as zinc in acetic acid. Nitroaldehydes of formula O are either known or may be made by methods known to persons skilled in the art, for instance they may be derived from nitro compounds of formula P by treatment with chloroform under basic conditions followed by treatment with strong aqueous acid. Alternatively, nitroaldehydes of formula O may be derived from oxidation of 1-nitro-2-methyl aromatic compounds of formula Q. A particularly convenient method of achieving such an oxidation involves treating the compound Q with dimethnitro compounds of formula S. There are numerous methods for achieving such a transformation reported in the literature such as treatment with tin or iron under acidic conditions, or hydrogenation catalysed by a noble metal such as palladium on carbon. Compounds of formula S may be derived from compounds of formula T, wherein R is OH, Cl, or $C_1$-$C_4$alkoxy, via acylation with an amine of formula $NHR_3R_4$ under the standard conditions already described for a compound of formula D. Similarly conversion of esters of formula T, wherein R is $C_1$-$C_4$alkoxy, to acids of formula T, wherein R is OH, to acid chlorides of formula T, wherein R is Cl, is also described for compounds of formula D. Compounds of formula T are either known or may be made by methods known to persons skilled in the art.

It must be recognised that some reagents and reaction conditions may not be compatible with certain functionalities that may be present in the molecules described. In such cases it may be necessary to employ standard protection/deprotection protocols comprehensively reported in the literature and well known to a person skilled in the art.

Also in some cases it may be necessary to perform further routine synthetic steps not described herein to complete the synthesis of the desired compounds. An artisan will also recognise that it may be possible to achieve the synthesis of the desired compounds by performing some of the steps in these synthetic routes in a different order to that described.

A person skilled in the art will also recognise that it may be possible to perform standard functional group interconversions or substitution reactions on the compounds described herein to introduce or modify existing substituents.

The reactants can preferably be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactions are advantageously carried out in a temperature range from approximately −80° C. to approximately +140° C., preferably from approximately −30° C. to approximately +100° C., in many cases in the range between room temperature and approximately +80° C.

The compounds of formula B, D and of formula A, wherein $Z_2$ is sulfur (compounds of formula AA) and, where appropriate, the tautomers thereof, in each case in free form or in salt form, are novel and are also subjects of the invention.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds of formula I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The invention relates to all those embodiments of the process by which, starting from a compound obtainable at any level of the process as starting material or intermediate, all or some of the missing steps are carried out or a starting material is used in the form of a derivative and/or salt and/or racemates or antipodes thereof or, in particular, is formed under the reaction conditions.

Those starting materials and intermediates, in each case in free form or in salt form, which lead to the compounds of formula I or salts thereof which have been described at the outset as being particularly valuable are preferably used in the process of the present invention.

In particular, the invention relates to the preparation processes described in the Examples P1 to P11.

Starting materials and intermediates, in each case in free form or in salt form, which are used in accordance with the invention for the preparation of the compounds of formula I or salts thereof and which are novel, a process for their preparation, and their use as starting materials and intermediates for the preparation of the compounds of formula I are also a subject of the invention; in particular, this applies to the compounds of formula II, IV and V.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example,

*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;

from the order Diptera, for example,

*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;

from the order Heteroptera, for example,

*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;

from the order Homoptera, for example,

*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;* from the order Hymenoptera, for example,

*Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;

from the order Isoptera, for example,

*Reticulitermes* spp.;

from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypi-ela, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Periplaneta* spp. and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Frankliniella* spp., *Hercinothrips* spp., *Scirtothrips aurantii, Taeniothrips* spp., *Thrips palmi* and *Thrips tabaci;* and from the order Thysanura, for example,

*Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops.

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (*Coleoptera*), two-winged insects (*Diptera*) and butterflies (*Lepidoptera*).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Boligard I® (cotton variety that expresses a CryIA(c) toxin); Boligard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard® and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain *Coleoptera* insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NU00/10. Genetically modified maize for the expression of the protein Cry1F for achieving resistance to certain *Lepidoptera* insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain *Lepidoptera*, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Other fields of application of the active ingredients according to the invention are the protection of stored products and stores and of material, such as wood, textiles, floor coverings or buildings, and, in the hygiene sector, particularly the protection of humans, domestic animals and productive livestock against pests of the abovementioned type.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethyl-ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise from 0.0001 to 99.9999%, in particular 0.1 to 95%, of active ingredient, and 0.0001 to 99.9999%, in particular 5 to 99.9%, of—at least—one solid or liquid auxiliary, it being possible, as a rule, for 0 to 25%, in particular 0.1 to 20%, of the compositions to be surfactants (% in each case is per cent by weight). While concentrated compositions are more preferred as commercially available goods, the end user uses, as a rule, dilute compositions which have considerably lower concentrations of active ingredient.

The activity of the compositions according to the invention can be broadened considerably, and adapted to prevailing circumstances, by adding other insecticidally or acaricidally active ingredients. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and Bacillus thuringiensis preparations.

Examples of especially suitable mixing partners include compounds selected from the following group M:

Group M: especially suitable mixing partners for the compounds of formula I: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a compound obtainable from the Bacillus thuringiensis strain GC91 or from strain NCTC11821; pymetrozine; bromopropylate; methoprene; disulfoton; quinalphos; tau-fluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; thiamethoxam; clothianidin; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; fenazaquin; pyriproxyfen; pyrimidifen; nitenpyram; acetamiprid; emamectin; emamectin-benzoate; spinosad; a plant extract that is active against insects; a preparation that comprises nematodes and is active against insects; a preparation obtainable from *Bacillus subtilis*; a preparation that comprises fungi and is active against insects; a preparation that comprises viruses and is active against insects; chlorfenapyr; acephate; acrinathrin; alanycarb; alphamethrin; amitraz; AZ 60541; azinphos A; azinphos M; azocyclotin; bendiocarb; bensultap; beta-cyfluthrin; BPMC; brofenprox; bromophos A; bufencarb; butocarboxin; butylpyridaben; cadusafos; carbaryl; carbophenothion; chloethocarb; chlorethoxyfos; chlormephos; cis-resmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; malathion; mecarbam; mesulfenphos; metaldehyde; metolcarb; milbemectin; moxidectin; naled; NC 184; omethoate; oxamyl; oxydemethon M; oxydeprofos; permethrin; phenthoate; phorate; phosmet; phoxim; pirimiphos M; pirimiphos E; promecarb; propaphos; prothiofos; prothoate; pyrachlophos; pyradaphenthion; pyresmethrin; pyrethrum; tebufenozide; salithion; sebufos; sulfotep; suiprofos; tebufenpyrad; tebupirimphos; tefluthrin; temephos; terbam; tetrachlorvinphos; thiacloprid; thiafenox; thiodicarb; thiofanox; thionazin; thuringiensin; tralomethrin; triarathene; triazophos; triazuron; trichlorfon; triflumuron; trimethacarb; vamidothion; xylylcarb; YI 5301/5302; zetamethrin; DPX-MP062-indoxacarb; methoxyfenozide; bifenazate; XMC (3,5-xylyl methylcarbamate); or the fungus pathogen Metarhizium anisopliae.

The following mixtures of the compounds of formula I with one member of the group M are preferred (in the following listing, "M" means one member selected from the group M.)

T1.1+M; T38.3+M; T37.3+M; T20.1+M; T1.3+M; T1.121+M; T2.1+M; T2.3+M; T6.1+M; T6.3+M; T7.1+M; T7.3+M; T21.3+M; T22.3+M; T46.1+M; T46.3+M; T50.1+M; T50.3+M; T51.1+M; T51.3+M; T52.1+M; T52.3+M; T53.1+M; T53.3+M; T72.1+M; T72.3+M; T72.207+M; T72.273+M; T73.1+M; T73.3+M; T73.207+M; T73.273+M; T74.1+M; T74.3+M; T75.1+M; T75.3+M; T76.1+M; T76.3+M; T77.1+M; T77.3+M; T78.1+M; T78.3+M; T79.1+M;

T80.3+M; T81.1+M; T81.3+M; T82.1+M; T83.3+M; T84.3+M and T85.3+M; P2.001+M; P2.002+M; P2.003+M; P2.004+M; P2.005+M; P2.006+M; P2.007+M; P2.008+M; P2.009+M; P2.010+M; P2.011+M; P2.012+M; P2.013+M; P2.014+M; P2.015+M; P2.016+M; P2.017+M; P2.018+M; P2.019+M; P2.020+M; P2.021+M; P2.022+M; P2.023+M; P2.024+M; P2.025+M; P2.026+M; P2.027+M; P2.028+M; P2.029+M; P2.030+M; P2.031+M; P2.032+M; P2.033+M; P2.034+M; P2.035+M; P2.036+M; P2.037+M; P2.038+M; P2.039+M; P2.040+M; P2.041+M; P2.042+M; P2.043+M; P2.044+M; P2.045+M; P2.046+M; P2.047+M; P2.048+M; P2.049+M; P2.050+M; P2.051+M; P2.052+M; P2.053+M; P2.054+M; P2.055+M; P2.056+M; P2.057+M; P2.058+M; P2.059+M; P2.060+M; P2.061+M; P2.062+M; P2.063+M; P2.064+M; P2.065+M; P2.066+M; P2.067+M; P2.068+M; P2.069+M; P2.070+M; P2.071+M; P2.072+M; P2.073+M; P2.074+M; P2.075+M; P2.076+M; P2.077+M; P2.078+M; P2.079+M; P2.080+M; P2.081+M; P2.082+M; P2.083+M; P2.084+M; P2.085+M; P2.086+M; P2.087+M; P2.088+M; P2.089+M; P2.090+M; P2.091+M; P2.092+M; P2.093+M; P2.094+M; P2.095+M; P2.096+M; P2.097+M; P2.098+M; P2.099+M; P2.100+M; P2.101+M; P2.102+M; P2.103+M; P2.104+M; P2.105+M; P2.106+M; P2.107+M; P2.108+M; P2.109+M; P2.110+M; P2.111+M; P2.112+M; P2.113+M; P2.114+M; P2.115+M; P2.116+M; P2.117+M; P2.118+M; P2.119+M; P2.120+M; P2.121+M; P2.122+M; P2.123+M; P2.124+M; P2.125+M; P2.126+M; P2.127+M; P2.128+M; P2.129+M; P2.130+M; P2.131+M; P2.132+M; P2.133+M; P2.134+M; P2.135+M; P2.136+M; P2.137+M; P2.138+M; P2.139+M; P2.140+M; P2.141+M; P2.142+M; P2.143+M; P2.144+M; P2.145+M; P2.146+M; P2.147+M; P2.148+M; P2.149+M; P2.150+M; P2.151+M; P2.152+M; P2.153+M; P2.154+M; P2.155+M; P2.156+M; P2.157+M; P2.158+M; P2.159+M; P2.160+M; P2.161+M; P2.162+M; P2.163+M; P2.164+M and P2.165+M.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds of formula I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

The examples which follow are intended to illustrate the invention. They do not limit the invention. Temperatures are given in degrees Celsius. The abbreviation "M. P." means "melting point".

PREPARATION EXAMPLES

Example P1

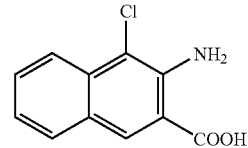

1.9 g (14.7 mmol) of N-chlorosuccinimide and 10 mg of 2,2'-azoisobutyric nitrile are added to a suspension of 2.5 g (13.3 mmol) of 2-amino-3-carboxy-naphthalene in 100 ml of tetrachloromethane. The reaction mixture is stirred for 18 hours at room temperature, treated with 250 ml of aqueous sodium chloride solution and extracted with ethyl acetate (3×250 ml): The combined organic layers are dried over magnesium sulfate and filtered, and the filtrate is concentrated in vacuo. This gives the title compound in the form of a brown solid [$^1$H-NMR (CDCl$_3$): 8.53 (s, 1H), 7.98 (d, 1H), 7.73 (d, 1H), 7.55 (t, 1H), 7.25 (t, 1H)].

Example P2

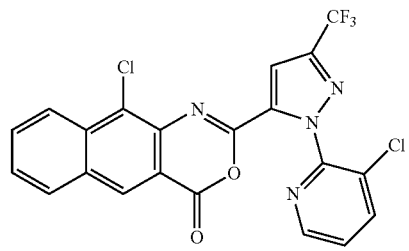

In a nitrogen atmosphere 0.5 ml (5.75 mmol) of oxalyl chloride are added dropwise at room temperature with stirring to a suspension of 295 mg (1.0 mmol) of 5-carboxy-1-(3-chloropyrid-2-yl)-3-trifluoromethyl-pyrazole in 2 ml of dichloromethane. The reaction mixture is stirred for 1 hour and then added dropwise to a solution of 0.25 g (1 mmol) of the title compound of Example P1 in a mixture of 20 ml of dichloromethane and 0.38 ml of triethylamine. The reaction mixture is subsequently stirred for 3 hours. Further 0.7 ml of triethylamine are added, followed by the addition of a single portion of 0.22 ml (2.8 mmol) of methane sulfonic acid chloride. The reaction mixture is then stirred for 18 hours and concentrated in vacuo, and the residue is purified by column chromatography [silica gel; hexane/ethyl acetate (3:1)], which gives the title compound [$^1$H-NMR (CDCl$_3$): 8.78 (s, 1H), 8.61 (m, 1H), 8.30 (m, 2H), 8.03 (dd, 1H), 7.78 (m, 1H), 7.67 (m, 1H), 7.56 (m, 2H); MS (electrospray): 477, 479, 481 ((M+H)$^+$)].

Example P3

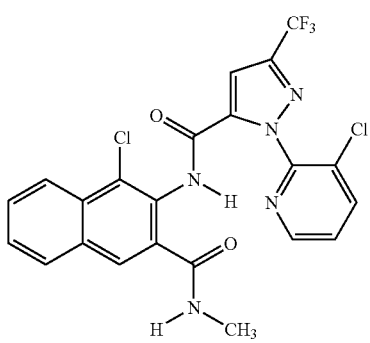

(T1.1)

In a nitrogen atmosphere 1 ml of a solution (2.0 M) of methylamine in anhydrous tetrahydrofuran is added with stirring to a solution of 0.07 g (0.15 mmol) of the title compound of Example P2 in 5 ml of anhydrous tetrahydrofuran. The reaction mixture is heated to 50° for 1 hour, allowed to cool to room temperature and concentrated in vacuo, and the residue is purified by column chromatography [silica gel; hexane, followed by hexane/ethyl acetate (3:1)], which gives the title compound T1.1 [$^1$H-NMR (DMSO-d$_6$): 10.80 (s, 1H), 8.53 (d, 1H), 8.45 (br s, 1H), 8.21 (m, 2H), 8.08 (m, 2H), 7.87 (s, 1H), 7.78 (t, 1H), 7.70 (t, 1H), 7.64 (dd, 1H), 2.70 (d, 3H); MS (electrospray): 508, 510, 512 ((M+H)$^+$)].

Example P4

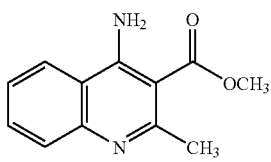

0.91 ml (8.46 mmol) of methyl acetoacetate and 1.98 ml (16.9 mmol) of tin tetrachloride are added to a solution of 1 g (8.46 mmol) of 1-amino-2-cyano-benzene in 20 ml of toluene. The reaction mixture is heated to reflux for 2 hours, allowed to cool to room temperature and concentrated in vacuo. The residue is suspended in 250 ml of aqueous sodium carbonate solution, and the suspension is stirred for 30 minutes, allowed to stand overnight and then extracted with ethyl acetate (3×250 ml). The combined organic layers are dried over magnesium sulfate and filtered, the filtrate is concentrated in vacuo, and the yellow solid residue is triturated with diethyl ether. This gives the title compound in the form of a yellow powder [$^1$H-NMR (CDCl$_3$): 7.88 (d, 1H), 7.77 (d, 1H), 7.68 (m, 1H), 7.43 (m, 1H), 7.06 (br s, 2H), 3.96 (s, 3H), 2.82 (s, 3H); MS (electrospray): 217 ((M+H)$^+$)].

Example P5

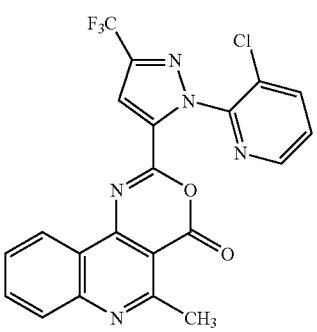

In a nitrogen atmosphere 4 drops of N,N-dimethylformamide and then 0.08 ml (0.93 mmol) of oxalyl chloride are added dropwise at room temperature with stirring to a suspension of 250 mg (0.86 mmol) of 5-carboxy-1-(3-chloropyrid-2-yl)-3-trifluoromethyl-pyrazole in 10 ml of dichloromethane. The reaction mixture is stirred for 1 hour, the solvent is removed in vacuo, and the residue is co-evaporated three times with toluene and then suspended in 3 ml of toluene to give the suspension "A". 105 mg (0.858 mmol) of 4-dimethylaminopyridine are added to a suspension of 185 mg (0.858 mmol) of the title compound of Example P4 in 3 ml of toluene to give the suspension "B". The suspension "A" is added to the suspension "B", for a complete transfer of the suspension "A" into the reaction flask the vessel containing the suspension "A" being rinsed out with a small amount of a mixture of toluene and a few drops of N,N-dimethylformamide. The reaction mixture is heated to reflux for 3 hours and then allowed to cool to room temperature. The yellow precipitate is filtered off and washed with diethyl ether. The filtrate is washed with 10 ml of water, and the water is back-extracted with ethyl acetate (2×50 ml). The combined organic layers are dried over magnesium sulfate and filtered, the filtrate is concentrated in vacuo, and the residue is purified by column chromatography [silica gel; hexane/ethyl acetate (1:2)], which gives the title compound [$^1$H-NMR (CDCl$_3$): 8.66 (d, 1H), 8.09 (d, 1H), 8.03 (d, 1H), 7.86 (t, 1H), 7.67 (s, 1H), 7.67 (d, 1H), 7.45 (m, 1H), 7.40 (dd, 1H), 3.09 (s, 3H); MS (electrospray): 458 ((M+H)$^+$)].

Example P6

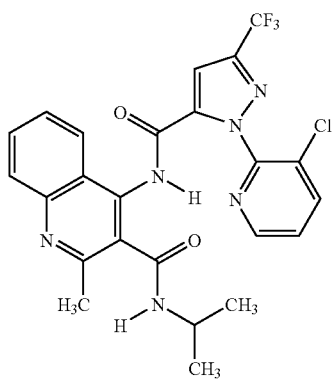

(T38.3)

0.022 ml (0.262 mmol) of isopropylamine are added with stirring to a suspension of 40 mg (0.087 mmol) of the title compound of Example P5 in 1 ml of anhydrous tetrahydrofuran. The reaction mixture is heated to 60° for 90 minutes, allowed to cool to room temperature and concentrated in vacuo, and the residue is purified by column chromatography [silica gel; methanol/dichloromethane (1:9)], which gives the title compound T38.3 [$^1$H-NMR (CDCl$_3$): 11.17 (s, 1H), 8.42 (d, 1H), 8.09 (s, 1H), 7.81 (d, 1H), 7.71 (t, 1H), 7.70 (d, 1H), 7.60 (d, 1H), 7.48 (t, 1H), 7.36 (m, 1H), 6.31 (d, 1H), 4.23 (m, 1H), 2.30 (s, 3H), 1.16 (d, 6H); MS (electrospray): 517 ((M+H)$^+$)].

Example P7

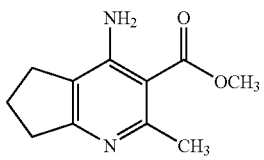

Starting from 1-amino-2-cyano-cyclopent-1-ene, the title compound can be prepared in a manner analogous to the procedure described in Example P4 [$^1$H-NMR (CDCl$_3$): 5.77 (br s, 2H), 3.90 (s, 3H), 2.97 (m, 2H), 2.70 (m, 2H), 2.15 (m, 2H); MS (electrospray): 207 ((M+H)$^+$)].

Example P8

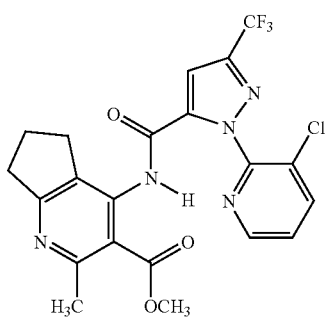

In a nitrogen atmosphere 4 drops of N,N-dimethylformamide and then 0.16 ml (1.86 mmol) of oxalyl chloride are added dropwise at room temperature with stirring to a suspension of 0.5 g (1.72 mmol) of 5-carboxy-1-(3-chloropyrid-2-yl)-3-trifluoromethyl-pyrazole in 20 ml of dichloromethane. The reaction mixture is stirred for 90 minutes, the solvent is removed in vacuo, and the residue is co-evaporated three times with toluene and then dissolved in 10 ml of tetrahydrofuran to give the solution "A". 0.24 ml (1.72 mmol) of triethylamine are added to a suspension of 195 mg (0.95 mmol) of the title compound of Example P7 in 10 ml of tetrahydrofuran to give the suspension "B". 5 ml of the solution "A" are added in portions over a period of 30 minutes to the suspension "B". The reaction mixture is stirred for 2.5 hours, treated with 10 ml of aqueous sodium hydrogen carbonate solution and extracted with ethyl acetate (2×40 ml). The combined organic layers are dried over magnesium sulfate and filtered, the filtrate is concentrated in vacuo, and the residue is purified by column chromatography (silica gel; ethyl acetate), which gives the title compound [$^1$H-NMR (CDCl$_3$): 10.15 (s, 1H), 8.49 (d, 1H), 7.92 (d, 1H), 7.45 (m, 1H), 7.22 (s, 1H), 3.96 (s, 3H), 2.99 (m, 2H), 2.75 (m, 2H), 2.67 (s, 3H), 2.06 (m, 2H); MS (electrospray): 480 ((M+H)$^+$)].

Example P9

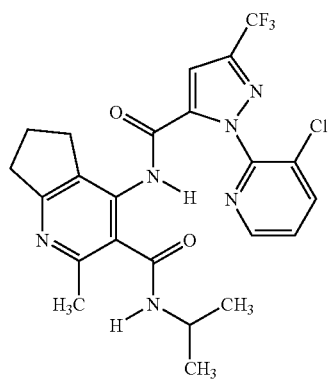

(T37.3)

0.04 ml (0.47 mmol) of isopropylamine are added at room temperature with stirring to a mixture of 0.24 ml of a solution (2.0 M) of trimethylaluminium in hexane and 3 ml of dichloromethane. The reaction mixture is stirred for 40 minutes. A solution of 110 mg (0.22 mmol) of the title compound of Example P8 in 3 ml of dichloromethane is added, and the reaction mixture is heated to reflux for 6 hours, allowed to cool to room temperature and to stand overnight and then poured into 20 ml of water. The mixture is extracted with dichloromethane (2×30 ml). The combined organic layers are dried over magnesium sulfate and filtered, the filtrate is concentrated in vacuo, and the residue is purified by column chromatography [silica gel; ethyl acetate/hexane (2:1), followed by neat ethyl acetate], which gives the title compound T37.3 [$^1$H-NMR (CDCl$_3$): 10.69 (s, 1H), 8.49 (d, 1H), 7.88 (d, 1H), 7.70 (s, 1H), 7.42 (m, 1H), 5.89 (d, 1H), 4.24 (m, 1H), 2.87 (t, 2H), 2.57 (t, 2H), 2.49 (s, 3H), 2.02 (m, 2H), 1.19 (d, 6H); MS (electrospray): 507 ((M+H)$^+$)].

Example P10

The compounds listed in the Table P1 and P2 can be prepared in a manner analogous to the procedures described in the Examples P1 to P9. Melting points are given in ° C. In the following structures, tertiary hydrogen atoms attached to carbon atoms are not drawn, e.g. the group

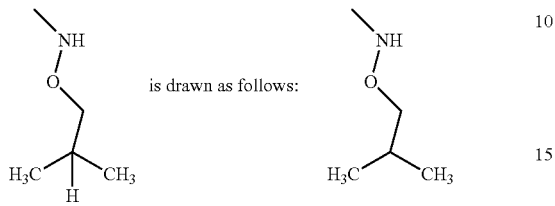

is drawn as follows:

TABLE P1

| Compound | Structure | MS | ¹H-NMR | M. P. |
|---|---|---|---|---|
| T1.3 | 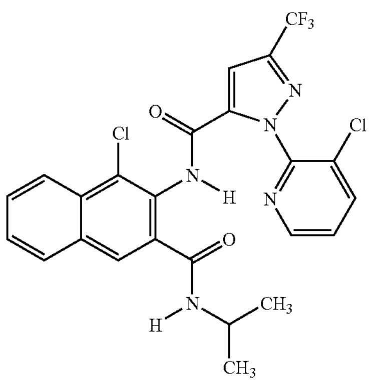 | Electrospray: 536, 538, 540 ((M + H)⁺). | CDCl$_3$: 8.43 (d, 1H), 7.91 (s, 1H), 7.81 (d, 1H), 7.64 (s, 1H), 7.59 (t, 2H), 7.33 (m, 2H), 7.22 (m, 1H), 6.19 (d, 1H), 4.19 (m, 1H), 1.18 (d, 6H). | |
| T1.121 | 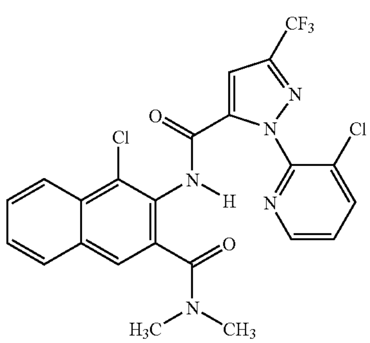 | Electrospray: 522, 524, 526 ((M + H)⁺). | CDCl$_3$: 10.95 (s, 1H), 8.43 (dd, 1H), 8.01 (s, 1H), 7.82 (d, 1H), 7.64 (d, 1H), 7.52 (s, 1H), 7.35 (m, 3H), 7.16 (t, 1H), 2.77 (s, 3H), 2.71 (s, 3H). | |
| T2.1 | 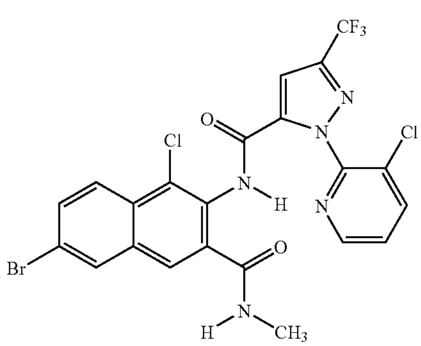 | Electrospray: 584, 586, 588, 590 ((M − H)⁺). | DMSO-d$_6$: 10.82 (s, 1H), 8.52 (dd, 1H), 8.47 (d, 1H), 8.40 (d, 1H), 8.20 (d, 1H), 8.14 (d, 1H), 8.05 (s, 1H), 7.89 (m, 1H), 7.87 (s, 1H), 7.64 (dd, 1H), 2.69 (d, 3H). | |

TABLE P1-continued

| Compound | Structure | MS | ¹H-NMR | M. P. |
|---|---|---|---|---|
| T2.3 | 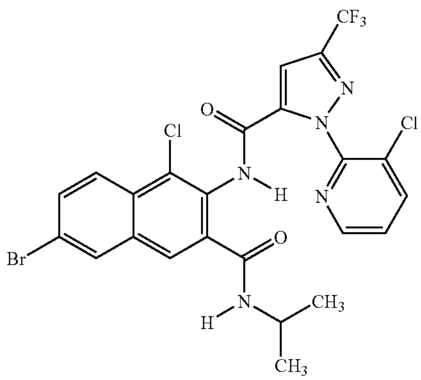 | Electrospray: 614, 616, 618 ((M + H)⁺). | DMSO-d$_6$: 10.80 (s, 1H), 8.50 (dd, 1H), 8.42 (d, 1H), 8.32 (d, 1H), 8.19 (d, 1H), 8.14 (d, 1H), 8.01 (s, 1H), 7.89 (s, 1H), 7.88 (m, 1H), 7.63 (dd, 1H), 3.92 (m, 1H), 1.06 (d, 6H). | |
| T6.1 | 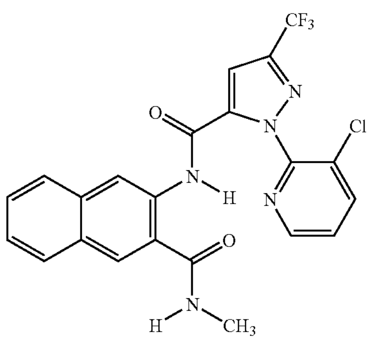 | Electrospray: 474, 476 ((M + H)⁺). | DMSO-d$_6$: 12.75 (s, 1H), 9.13 (d, 1H), 8.69 (s, 1H), 8.60 (d, 1H), 8.44 (s, 1H), 8.31 (d, 1H), 7.91 (m, 2H), 7.74 (dd, 1H), 7.55 (m, 3H), 2.89 (d, 3H). | |
| T6.3 | 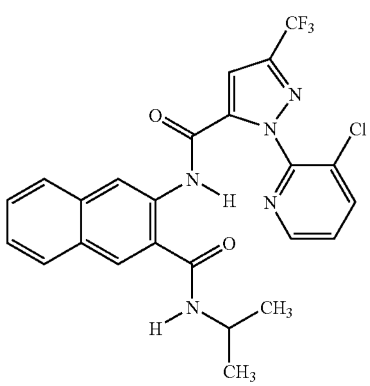 | Electrospray: 502, 504 ((M + H)⁺). | DMSO-d$_6$: 12.55 (s, 1H), 8.90 (d, 1H), 8.62 (s, 1H), 8.59 (d, 1H), 8.43 (s, 1H), 8.31 (d, 1H), 7.94 (d, 1H), 7.90 (d, 1H), 7.73 (dd, 1H), 7.55 (m, 3H), 4.21 (m, 1H), 1.23 (d, 6H). | |
| T7.1 | 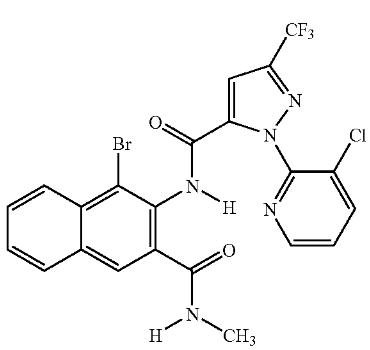 | Electrospray: 552, 554, 556 ((M + H)⁺). | DMSO-d$_6$: 10.80 (s, 1H), 8.52 (d, 1H), 8.42 (s, 1H), 8.20 (m, 2H), 8.11 (s, 1H), 8.05 (d, 1H), 7.88 (s, 1H), 7.75 (t, 1H), 7.64 (m, 2H), 2.70 (d, 3H). | |

TABLE P1-continued

| Compound | Structure | MS | ¹H-NMR | M. P. |
|---|---|---|---|---|
| T7.3 | 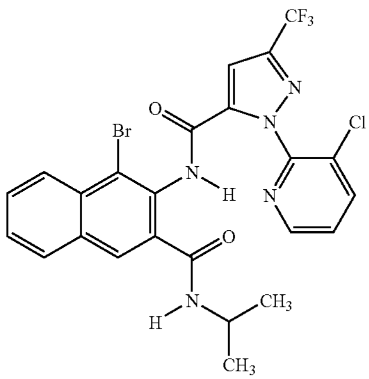 | Electrospray: 580, 582, 584 ((M + H)⁺). | CDCl$_3$: 10.65 (s, 1H), 8.43 (d, 1H), 7.98 (s, 1H), 7.81 (d, 1H), 7.71 (s, 1H), 7.60 (d, 1H), 7.56 (d, 1H), 7.34 (m, 2H), 7.21 (t, 1H), 6.12 (d, 1H), 4.20 (m, 1H), 1.17 (d, 6H). | |
| T21.3 | 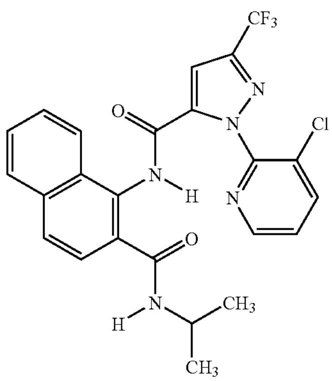 | Electrospray: 502, 504 ((M + H)⁺). | CDCl$_3$: 10.97 (s, 1H), 8.46 (d, 1H), 7.84 (m, 2H), 7.75 (s, 1H), 7.72 (m, 1H), 7.49 (m, 2H), 7.37 (m, 2H), 7.11 (d, 1H), 6.15 (d, 1H), 4.23 (m, 1H), 1.19 (d, 6H). | |
| T22.3 | 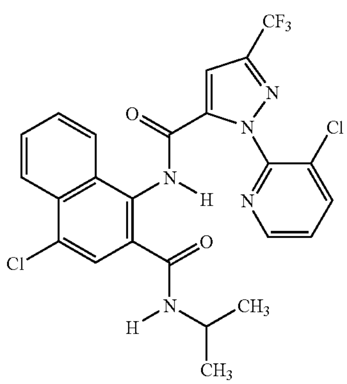 | Electrospray: 536, 538 ((M + H)⁺). | CDCl$_3$: 11.00 (s, 1H), 8.43 (d, 1H), 7.96 (d, 1H), 7.87 (s, 1H), 7.81 (m, 2H), 7.58 (m, 2H), 7.36 (m, 1H), 7.05 (s, 1H), 6.12 (d, 1H), 4.20 (m, 1H), 1.20 (d, 6H). | |
| T46.1 | 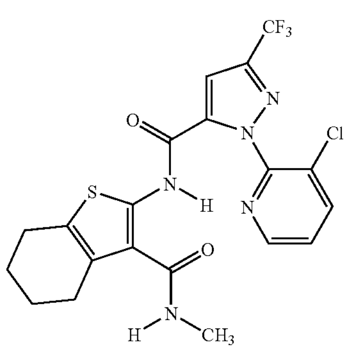 | | | 261-263 |

TABLE P1-continued
| Compound | Structure | MS | ¹H-NMR | M. P. |
|---|---|---|---|---|
| T46.3 | 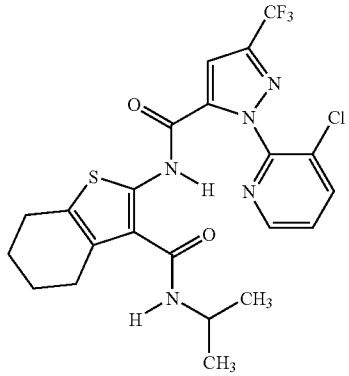 | | | 246-248 |
| T50.1 | 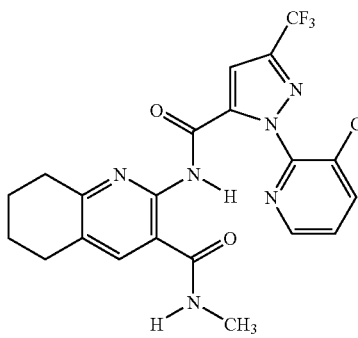 | | | 145-147 |
| T50.3 | 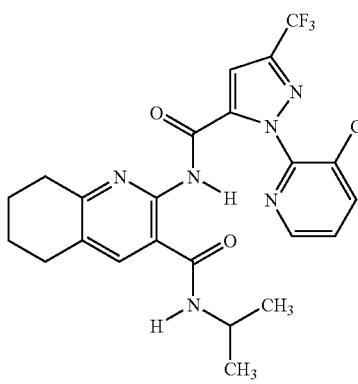 | | | 143-145 |
| T51.1 | 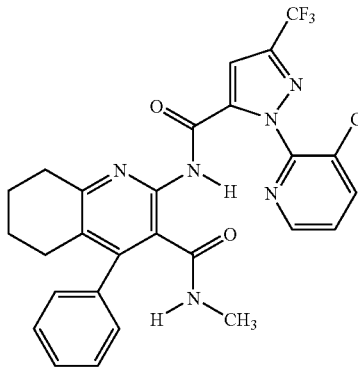 | | | 165-168 |

TABLE P1-continued

| Compound | Structure | MS | ¹H-NMR | M. P. |
|---|---|---|---|---|
| T51.3 | 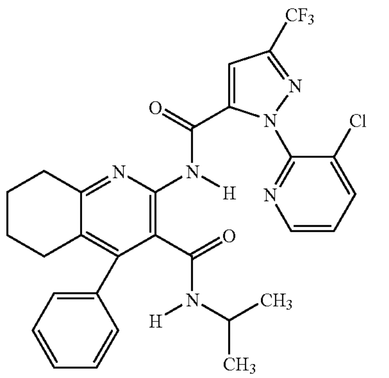 | | | 146-148 |
| T52.1 | 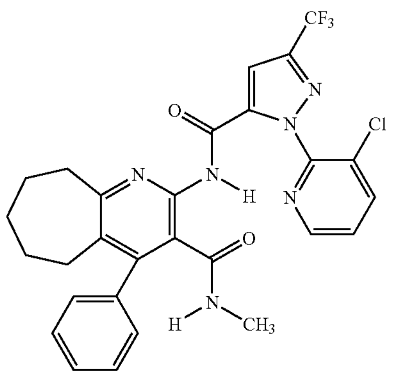 | | | 211-213 |
| T52.3 | 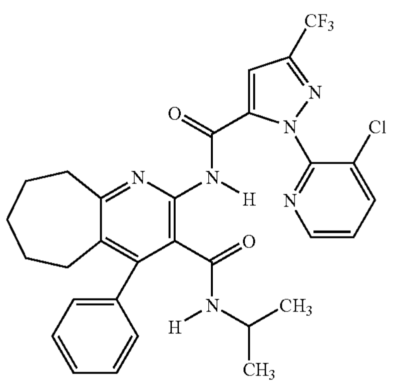 | | | 269-270 |
| T53.1 | 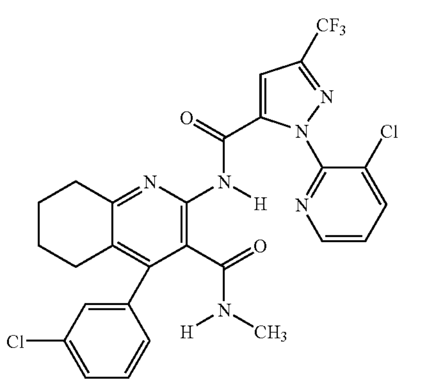 | | | 183-185 |

TABLE P1-continued
| Compound | Structure | MS | ¹H-NMR | M. P. |
|---|---|---|---|---|
| T53.3 | 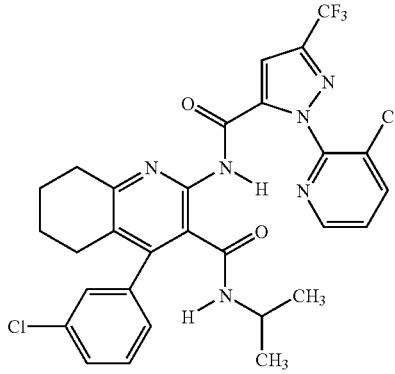 | | | 259-260 |
| T72.1 | 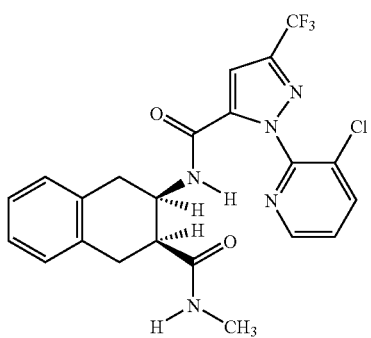 | | | 226-228 |
| T72.3 | 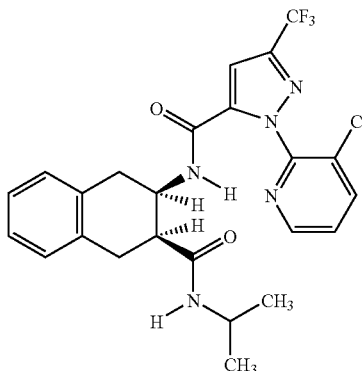 | | | 229-232 |
| T72.207 | 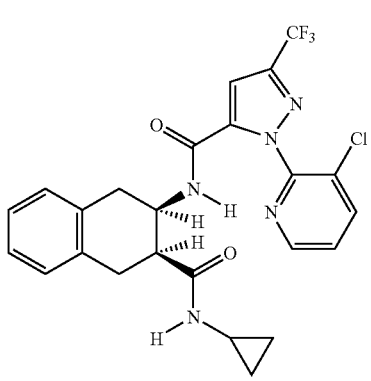 | | | 230-233 |

TABLE P1-continued

| Compound | Structure | MS | ¹H-NMR | M. P. |
|---|---|---|---|---|
| T72.273 | 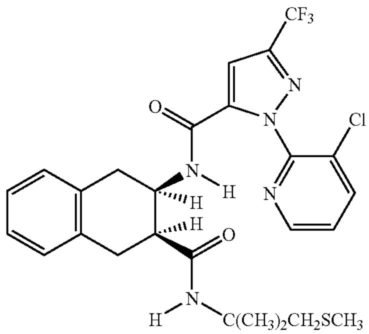 | | | 184-186 |
| T73.1 | 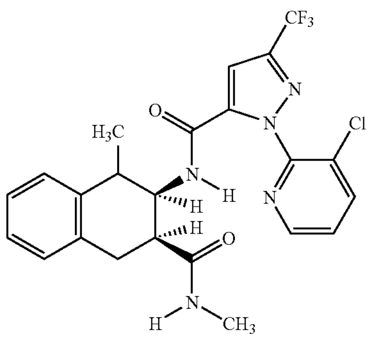 | | | 205-207 |
| T73.3 | 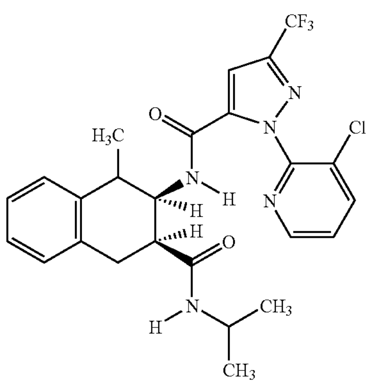 | | | 223-225 |
| T73.207 | 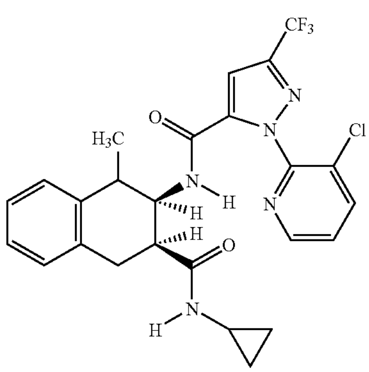 | | | 192-194 |

TABLE P1-continued
| Compound | Structure | MS | ¹H-NMR | M. P. |
|---|---|---|---|---|
| T73.273 | 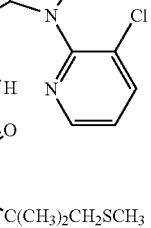 | Electrospray: 580 ((M + H)⁺). | | |
| T74.1 | 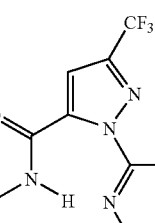 | | | 133-135 |
| T74.3 | 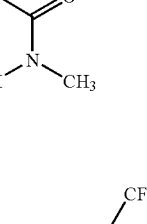 | | | 206-207 |
| T75.1 | 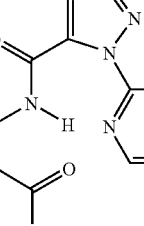 | Electrospray: 489 ((M + H)⁺). | CDCl₃: 11.97 (s, 1H), 8.50 (br s, 1H), 8.49 (dd, 1H), 8.00 (d, 1H), 7.87 (dd, 1H), 7.69 (m, 1H), 7.61 (m, 1H), 7.45 (s, 1H), 7.41 (m, 1H), 3.09 (d, 3H), 2.52 (s, 3H). | |

TABLE P1-continued

| Compound | Structure | MS | ¹H-NMR | M. P. |
|---|---|---|---|---|
| T75.3 | 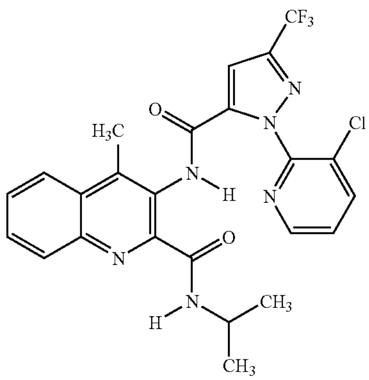 | Electrospray: 517 ((M + H)⁺). | CDCl₃: 12.06 (s, 1H), 8.49 (dd, 1H), 8.33 (m, 1H), 8.04 (d, 1H), 7.99 (d, 1H), 7.87 (dd, 1H), 7.69 (m, 1H), 7.61 (m, 1H), 7.44 (s, 1H), 7.41 (m, 1H), 4.30 (m, 1H), 2.52 (s, 3H), 1.35 (d, 6H). | |
| T76.1 | 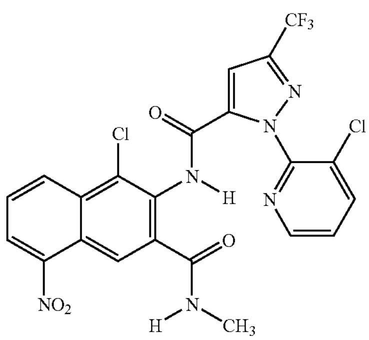 | | CDCl₃: 8.47 (d, 1H), 8.17 (s, 1H), 8.13 (d, 1H), 8.08 (m, 1H), 7.94 (d, 1H), 7.85 (d, 1H), 7.73 (s, 1H), 7.67 (m, 1H), 7.48 (m, 1H), 2.93 (d, 3H). | |
| T76.3 | 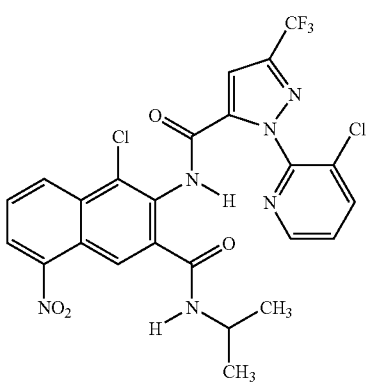 | Electrospray: 581 ((M + H)⁺). | CDCl₃: 10.95 (s, 1H), 8.59 (d, 1H), 8.47 (dd, 1H), 8.39 (s, 1H), 8.33 (d, 1H), 8.30 (d, 1H), 8.04 (d, 1H), 7.89 (s, 1H), 7.84 (m, 1H), 7.56 (m, 1H), 4.02 (m, 1H), 1.11 (d, 6H). | |
| T77.1 | 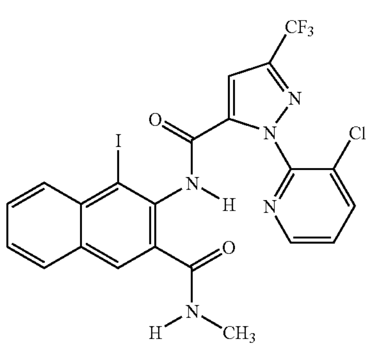 | Electrospray: 600 ((M + H)⁺). | CDCl₃: 10.29 (s, 1H), 8.47 (dd, 1H), 7.85 (dd, 1H), 7.81 (s, 1H), 7.71 (s, 1H), 7.70 (d, 1H), 7.63 (d, 1H), 7.40 (m, 1H), 7.38 (m, 1H), 7.33 (m, 1H), 6.26 (m, 1H), 2.96 (d, 3H). | |

TABLE P1-continued

| Compound | Structure | MS | ¹H-NMR | M. P. |
|---|---|---|---|---|
| T77.3 | 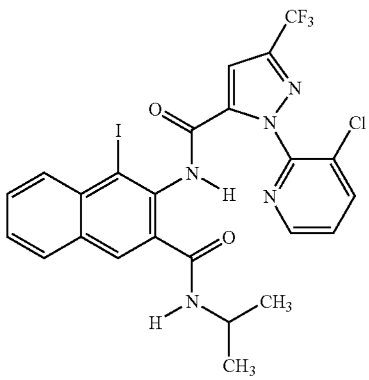 | Electrospray: 628 ((M + H)⁺). | CDCl₃: 10.61 (s, 1H), 8.45 (dd, 1H), 7.93 (s, 1H), 7.83 (dd, 1H), 7.78 (s, 1H), 7.57 (d, 1H), 7.36 (m, 2H), 7.24 (m, 1H), 6.10 (d, 1H), 4.20 (m, 1H), 1.16 (d, 6H). | |
| T78.1 | 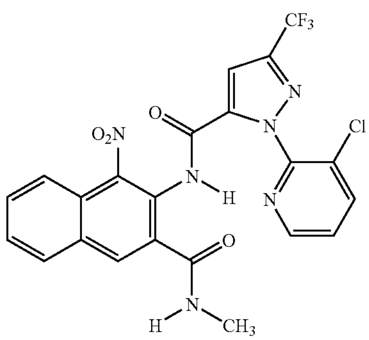 | Electrospray: 519 ((M + H)⁺). | CDCl₃: 10.82 (br s, 1H), 8.50 (d, 1H), 8.05 (s, 1H), 7.93 (d, 1H), 7.84 (d, 1H), 7.79 (d, 1H), 7.65 (m, 1H), 7.52 (m, 1H), 7.45 (m, 1H), 7.28 (s, 1H), 6.58 (br s, 1H), 2.98 (d, 3H). | |
| T78.3 | 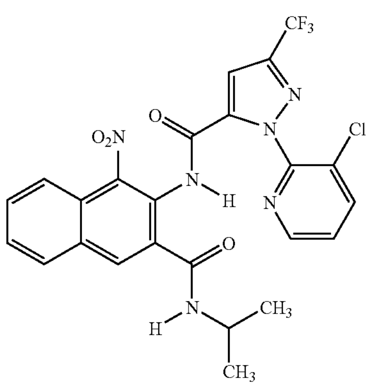 | Electrospray: 547 ((M + H)⁺). | CDCl₃: 11.02 (br s, 1H), 8.47 (d, 1H), 8.07 (s, 1H), 7.88 (d, 1H), 7.82 (d, 1H), 7.73 (d, 1H), 7.59 (m, 1H), 7.53 (m, 1H), 7.48 (s, 1H), 7.40 (m, 1H), 6.20 (br s, 1H), 4.27 (m, 1H) 1.27 (d, 6H). | |
| T79.1 | 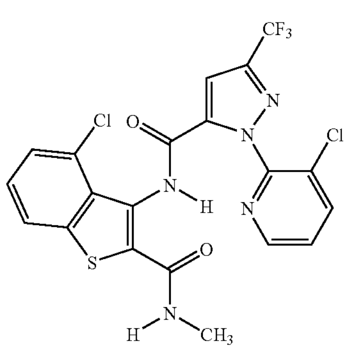 | Electrospray: 514 ((M + H)⁺). | CDCl₃: 9.15 (s, 1H), 8.53 (dd, 1H), 8.22 (dd, 1H), 8.14 (d, 1H), 8.04 (d, 1H), 7.83 (s, 1H), 7.66 (m, 1H), 7.47 (m, 2H), 2.77 (s, 3H). | |

TABLE P1-continued
| Compound | Structure | MS | ¹H-NMR | M. P. |
|---|---|---|---|---|
| T80.3 | 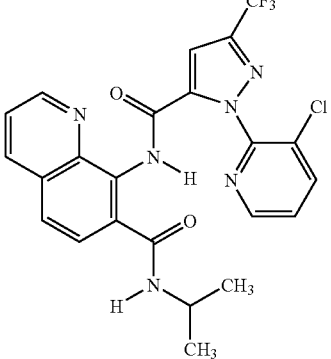 | Electrospray: 503, 505 ((M + H)⁺). | CDCl₃: 10.10 (s, 1H), 8.87 (d, 1H), 8.43 (d, 1H), 8.09 (d, 1H), 7.85 (d, 1H), 7.58 (m, 2H), 7.49 (m, 2H), 7.38 (m, 1H), 6.01 (d, 1H), 4.17 (m, 1H), 1.14 (d, 6H). | |
| T81.1 | 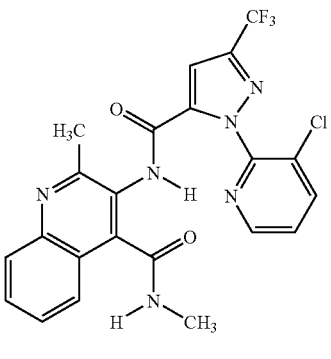 | Electrospray: 489 ((M + H)⁺). | CDCl₃: 10.20 (s, 1H), 8.46 (d, 1H), 7.94 (d, 1H), 7.87 (d, 1H), 7.84 (s, 1H), 7.76 (t, 1H), 7.74 (d, 1H), 7.55 (t, 1H), 7.41 (m, 1H), 6.45 (m, 1H), 3.04 (d, 3H), 1.94 (s, 3H). | |
| T81.3 | 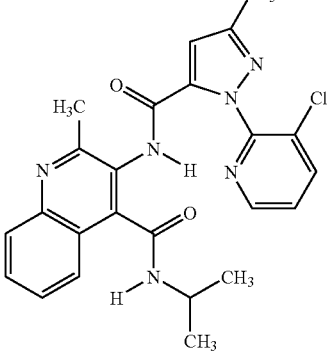 | Electrospray: 517 ((M + H)⁺). | CDCl₃: 10.49 (s, 1H), 8.44 (d, 1H), 7.93 (d, 1H), 7.92 (s, 1H), 7.85 (d, 1H), 7.75 (t, 1H), 7.74 (d, 1H), 7.54 (t, 1H), 7.39 (m, 1H), 6.29 (d, 1H), 4.28 (m, 1H), 1.81 (s, 3H), 1.18 (d, 6H). | |
| T82.1 | 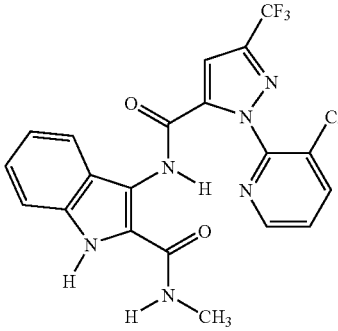 | Electrospray: 463 ((M + H)⁺). | DMSO-d₆: 11.58 (s, 1H), 10.65 (s, 1H), 8.57 (dd, 1H), 8.26 (dd, 1H), 7.87 (s, 1H), 7.84 (m, 1H), 7.68 (m, 1H), 7.44 (d, 1H), 7.40 (d, 1H), 7.21 (t, 1H) 7.03 (t,1H), 2.82 (s, 3H). | |

TABLE P1-continued
| Compound | Structure | MS | ¹H-NMR | M. P. |
|---|---|---|---|---|
| T83.3 | 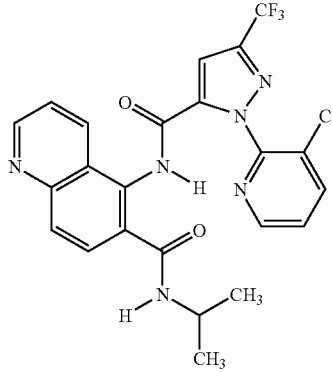 | Electrospray: 503, 505 ((M + H)⁺). | CDCl₃: 11.22 (s, 1H), 8.90 (m, 1H), 8.44 (d, 1H), 8.14 (d, 1H), 7.85 (d, 1H), 7.78 (s, 1H), 7.54 (d, 1H), 7.40 (m, 2H), 7.30 (d, 1H), 6.22 (d, 1H), 4.25 (m, 1H), 1.22 (d, 6H). | |
| T84.3 | 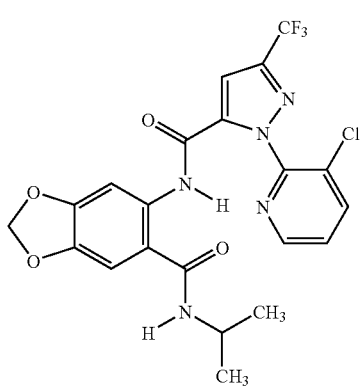 | Electrospray: 496, 498 ((M + H)⁺). | DMSO-d₆: 13.48 (s, 1H), 8.54 (d, 1H), 8.10 (d, 1H), 8.02 (m, 2H), 7.56 (m, 1H), 7.46 (s, 1H), 7.29 (s, 1H), 6.00 (s, 2H), 4.28 (m, 1H), 1.26 (d, 6H). | |
| T85.3 | 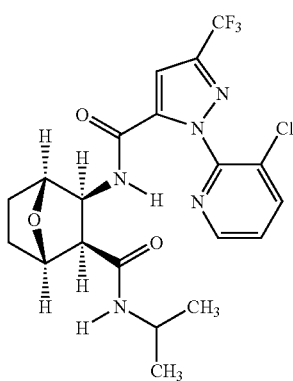 | | | 220-224 |
| T88.3 | 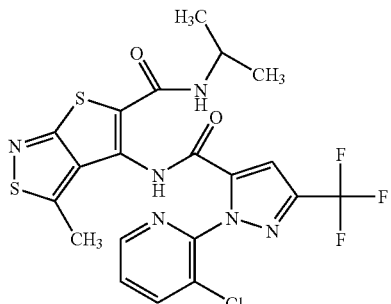 | | | 261-263 |

TABLE P1-continued

| Compound | Structure | MS | ¹H-NMR | M. P. |
|---|---|---|---|---|
| T88.1 | 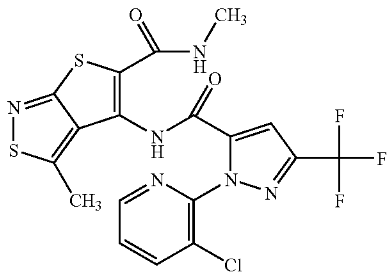 | | | 264-266 |
| T89.1 | 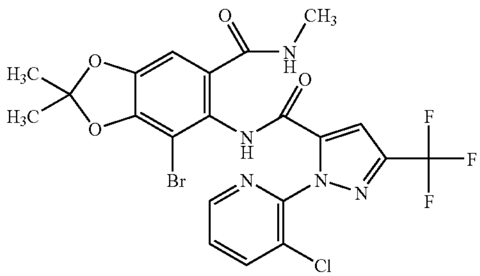 | | | 274-276 |
| T90.1 | 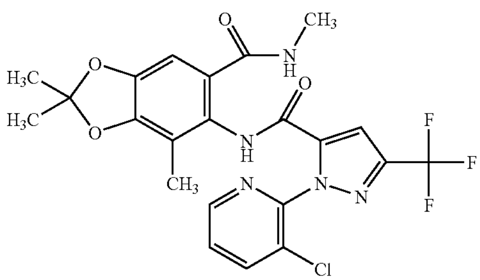 | | | 242-244 |
| T90.3 | 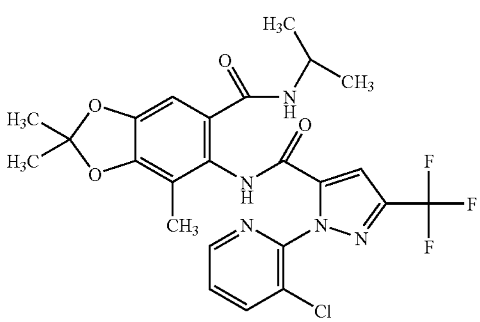 | | | 256-258 |
| T91.1 | 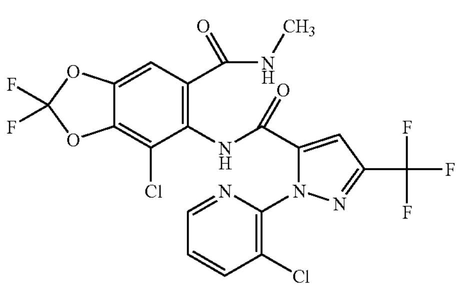 | | | 265-267 |

TABLE P1-continued
| Compound | Structure | MS | ¹H-NMR | M. P. |
|---|---|---|---|---|
| T91.3 | 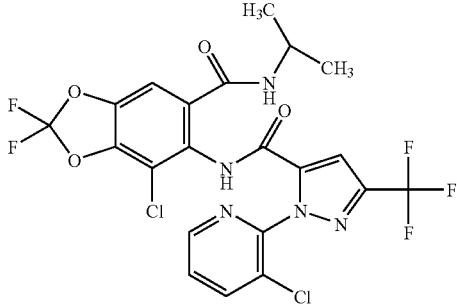 | | | 251-253 |
TABLE P2
| Comp. Nr. | Structure | Phys. Data (MS., NMR, M. P in ° C.) |
|---|---|---|
| P2.001 | 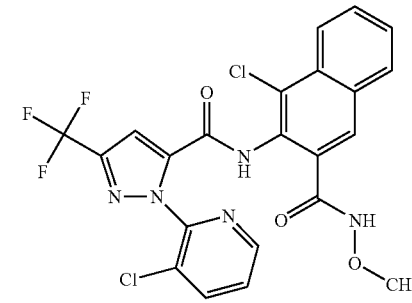 | 524 (M + H)+) |
| P2.002 | 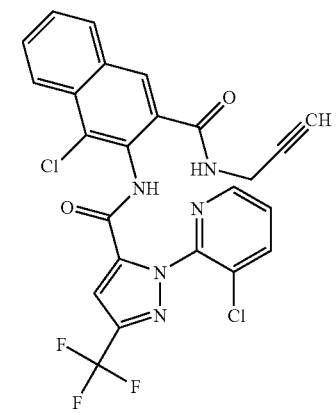 | 532 ((M + H)+) |
| P2.003 | 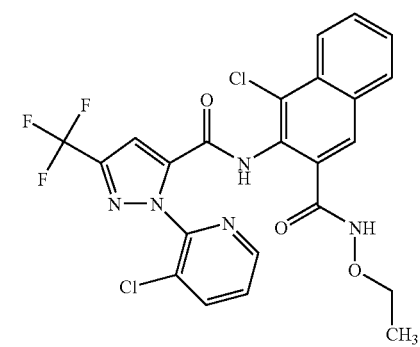 | 538 ((M + H)+) |

TABLE P2-continued

| Comp. Nr. | Structure | Phys. Data (MS., NMR, M. P in °C.) |
|---|---|---|
| P2.004 | 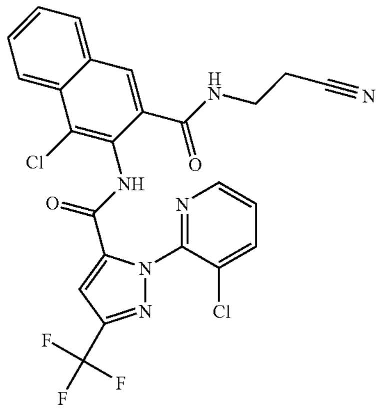 | 547 ((M + H)+) |
| P2.005 | 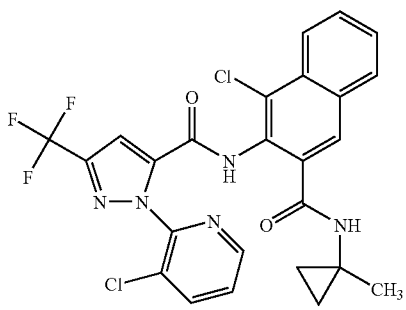 | 548 ((M + H)+) |
| P2.006 | 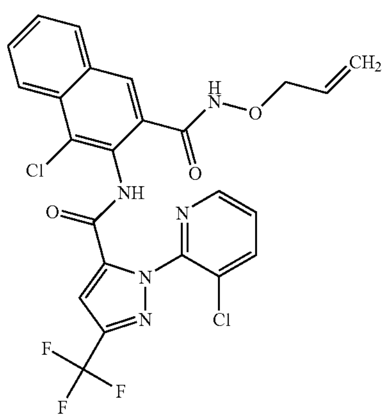 | 550 ((M + H)+) |
| P2.007 | 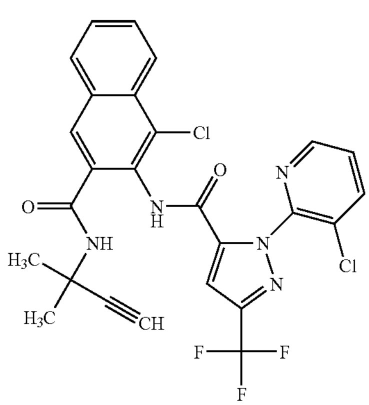 | 560 ((M + H)+) |

TABLE P2-continued

| Comp. Nr. | Structure | Phys. Data (MS., NMR, M. P in °C.) |
|---|---|---|
| P2.008 | 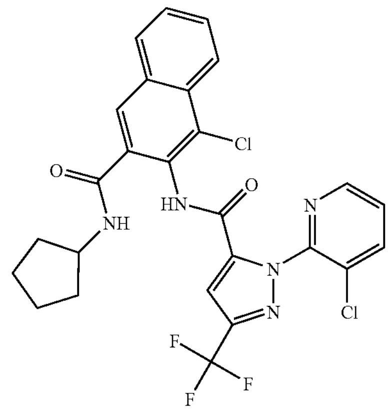 | 562 ((M + H)+) |
| P2.009 | 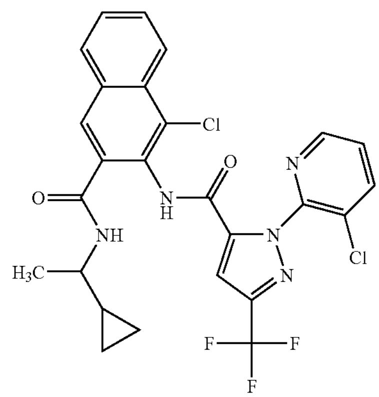 | 562 ((M + H)+) |
| P2.010 | 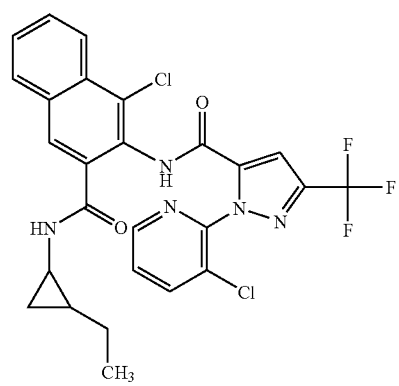 | 562 ((M + H)+) |
| P2.011 | 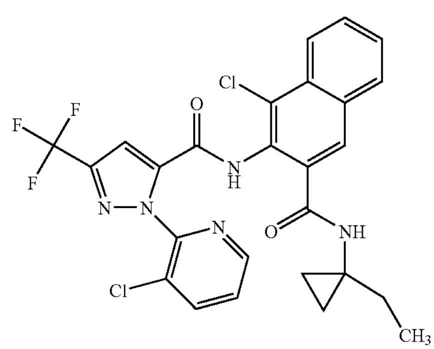 | 562 ((M + H)+) |

TABLE P2-continued

| Comp. Nr. | Structure | Phys. Data (MS., NMR, M. P in °C.) |
|---|---|---|
| P2.012 | 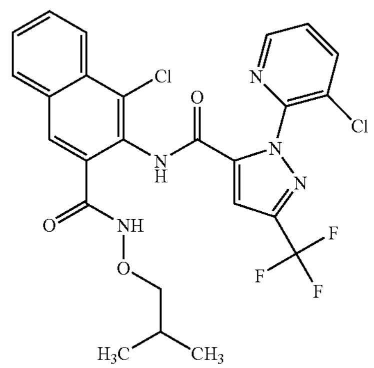 | 566 ((M + H)+) |
| P2.013 | 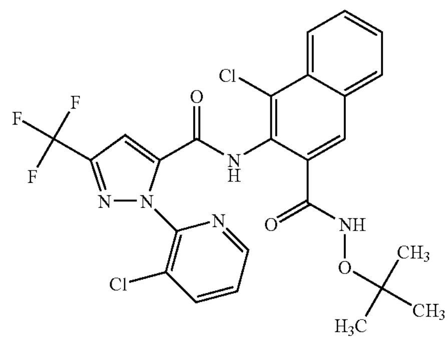 | 566 ((M + H)+) |
| P2.014 | 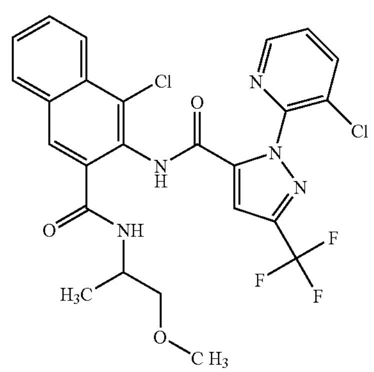 | 566 ((M + H)+) |
| P2.015 | 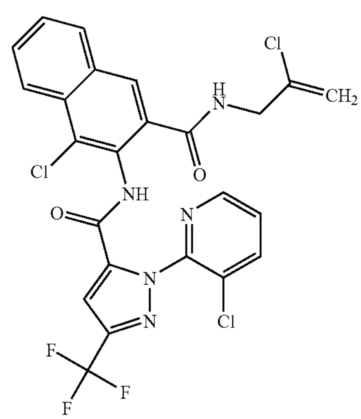 | 568 ((M + H)+) |

TABLE P2-continued

| Comp. Nr. | Structure | Phys. Data (MS., NMR, M. P in °C.) |
|---|---|---|
| P2.016 | 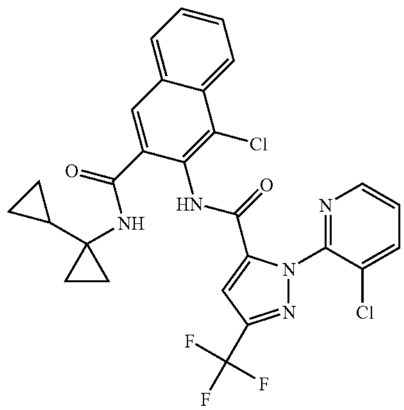 | 574 ((M + H)+) |
| P2.017 | 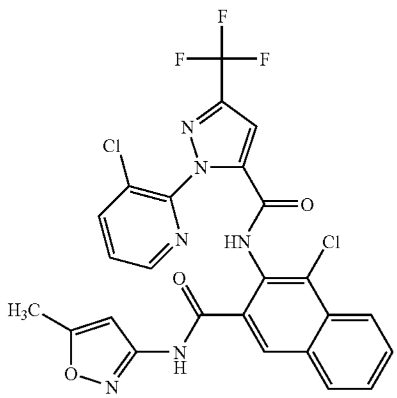 | 575 ((M + H)+) |
| P2.018 | 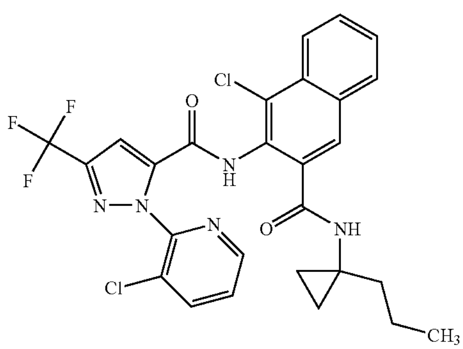 | 576 ((M + H)+) |
| P2.019 | 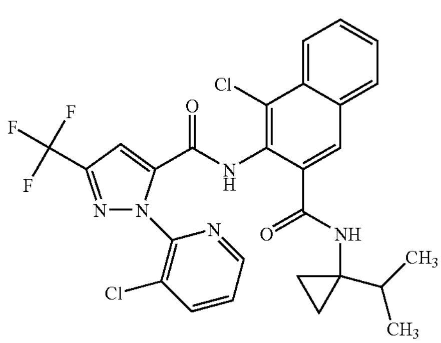 | 576 ((M + H)+) |

TABLE P2-continued

| Comp. Nr. | Structure | Phys. Data (MS., NMR, M. P in °C.) |
|---|---|---|
| P2.020 | 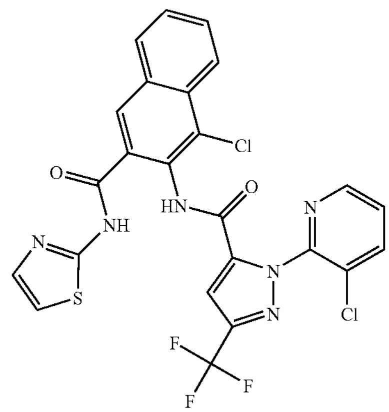 | 577 ((M + H)+) |
| P2.021 | 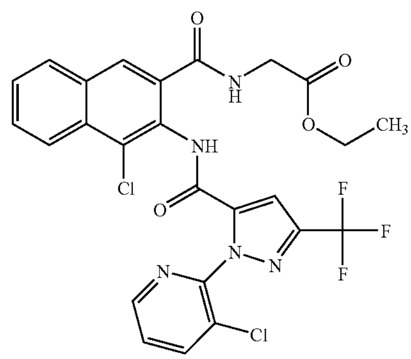 | 580 ((M + H)+) |
| P2.022 | 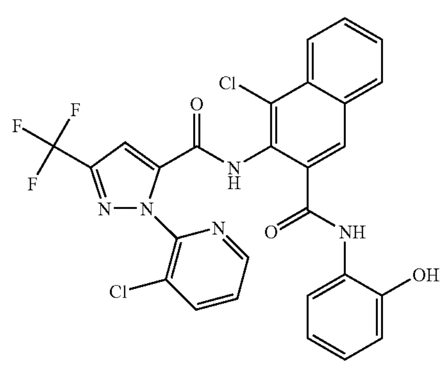 | 586 ((M + H)+) |
| P2.023 | 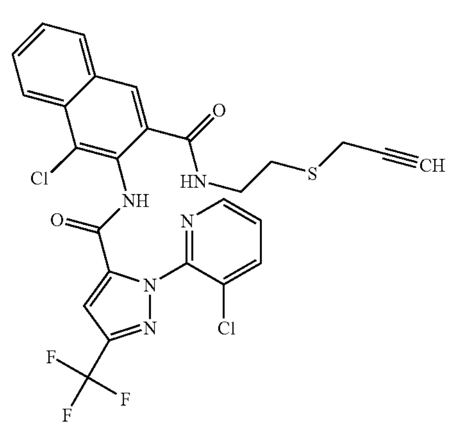 | 592 ((M + H)+) |

TABLE P2-continued

| Comp. Nr. | Structure | Phys. Data (MS., NMR, M. P in °C.) |
|---|---|---|
| P2.024 | 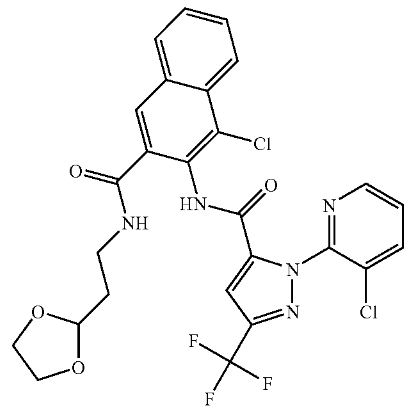 | 594 ((M + H)+) |
| P2.025 | 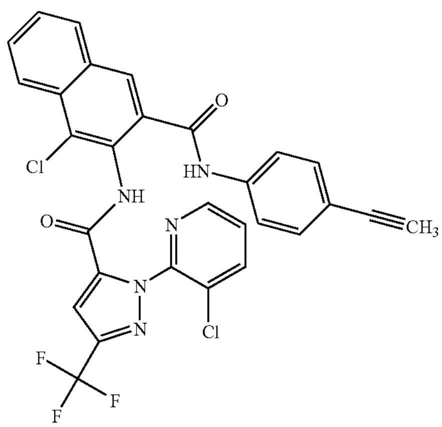 | 594 ((M + H)+) |
| P2.026 | 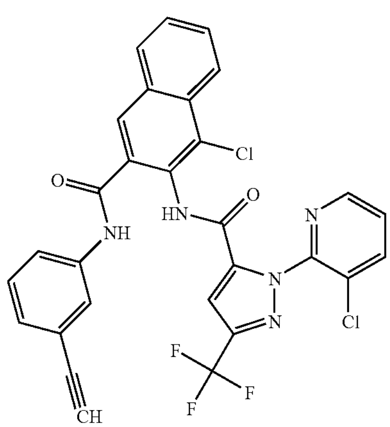 | 594 ((M + H)+) |

TABLE P2-continued

| Comp. Nr. | Structure | Phys. Data (MS., NMR, M. P in ° C.) |
|---|---|---|
| P2.027 | 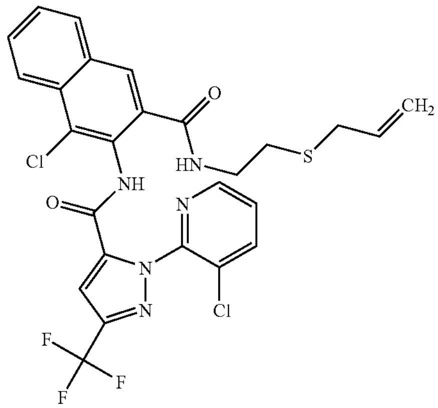 | 594 ((M + H)+) |
| P2.028 | 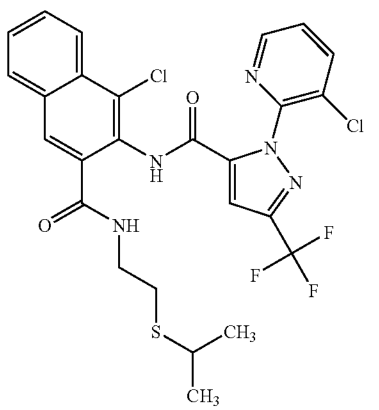 | 596 ((M + H)+) |
| P2.029 | 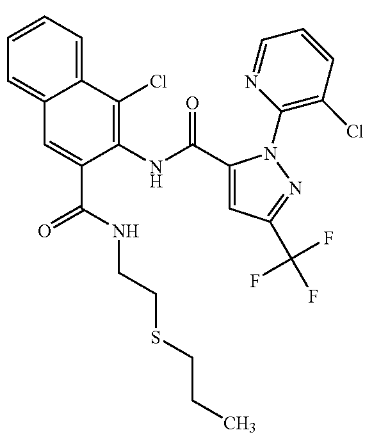 | 596 ((M + H)+) |

TABLE P2-continued

| Comp. Nr. | Structure | Phys. Data (MS., NMR, M. P in ° C.) |
|---|---|---|
| P2.030 (T1.273) | 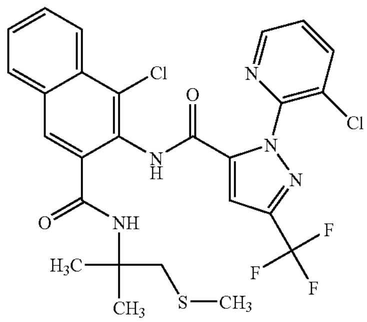 | 596 ((M + H)+) |
| P2.031 | 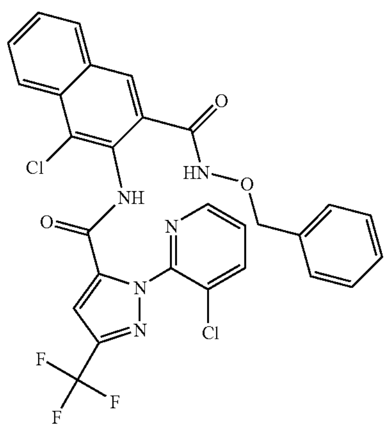 | 600 ((M + H)+) |
| P2.032 | 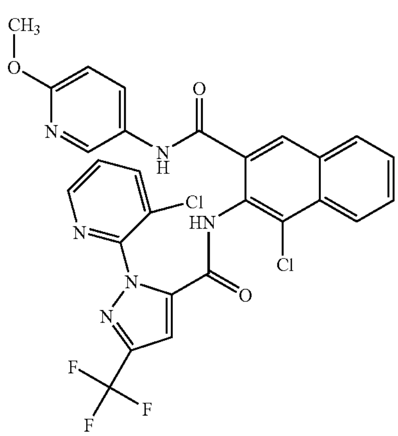 | 601 ((M + H)+) |

TABLE P2-continued

| Comp. Nr. | Structure | Phys. Data (MS., NMR, M. P in °C.) |
|---|---|---|
| P2.033 | 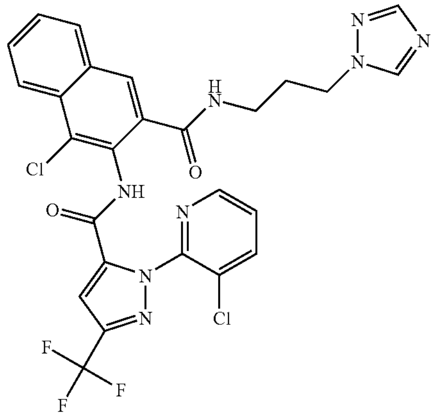 | 603 ((M + H)+) |
| P2.034 | 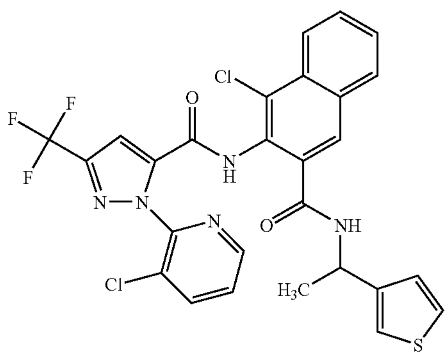 | 604 ((M + H)+) |
| P2.035 | 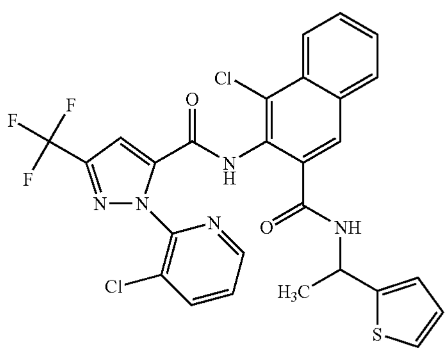 | 604 ((M + H)+) |
| P2.036 | 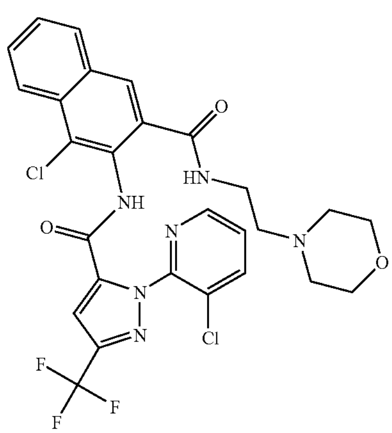 | 607 ((M + H)+) |

TABLE P2-continued

| Comp. Nr. | Structure | Phys. Data (MS., NMR, M. P in °C.) |
|---|---|---|
| P2.037 | 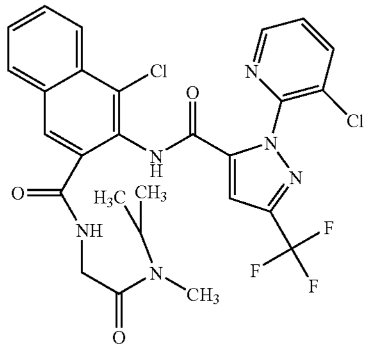 | 607 ((M + H)+) |
| P2.038 | 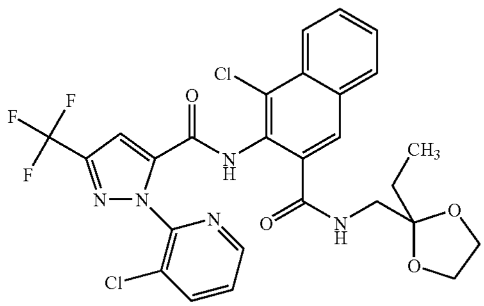 | 608 ((M + H)+) |
| P2.039 | 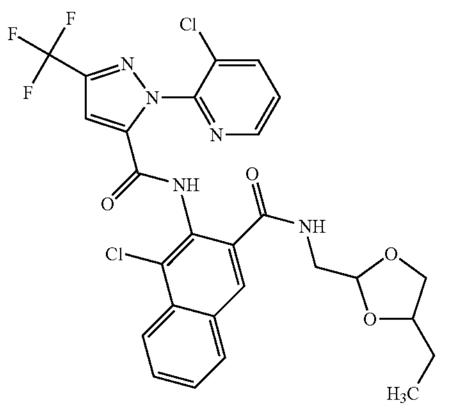 | 608 ((M + H)+) |
| P2.040 | 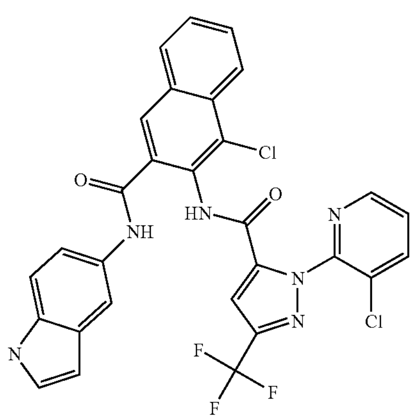 | 609 ((M + H)+) |

TABLE P2-continued

| Comp. Nr. | Structure | Phys. Data (MS., NMR, M. P in ° C.) |
|---|---|---|
| P2.041 | 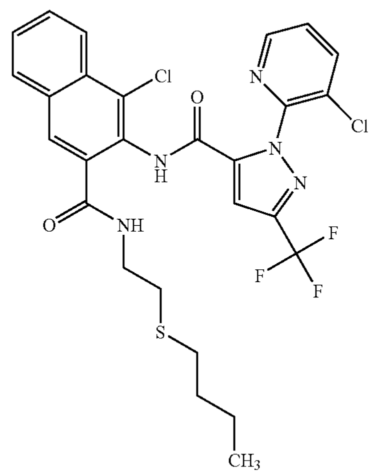 | 610 ((M + H)+) |
| P2.042 | 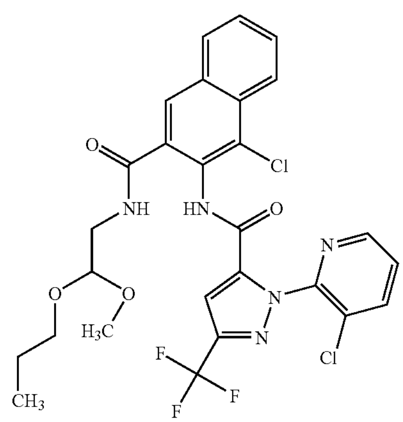 | 610 ((M + H)+) |
| P2.043 | 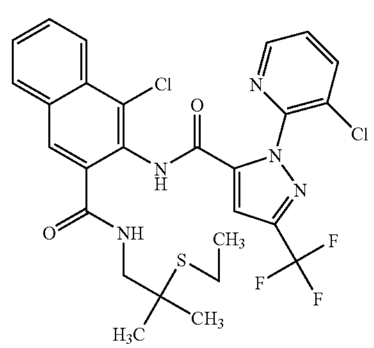 | 610 ((M + H)+) |

TABLE P2-continued

| Comp. Nr. | Structure | Phys. Data (MS., NMR, M. P in °C.) |
|---|---|---|
| P2.044 | 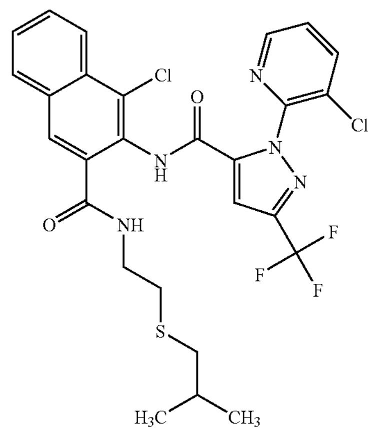 | 610 ((M + H)+) |
| P2.045 | 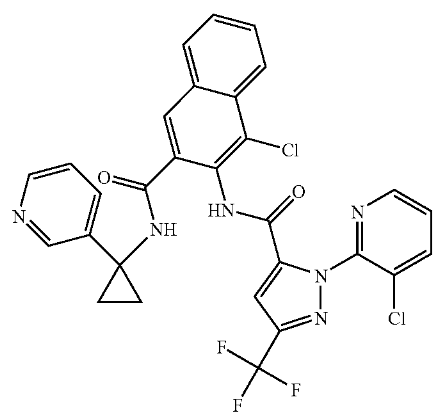 | 611 ((M + H)+) |
| P2.046 | 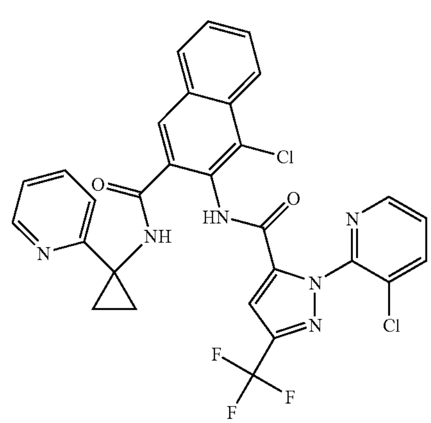 | 611 ((M + H)+) |

TABLE P2-continued

| Comp. Nr. | Structure | Phys. Data (MS., NMR, M. P in ° C.) |
|---|---|---|
| P2.047 | 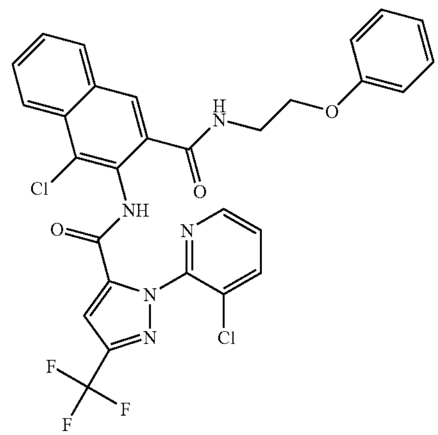 | 614 ((M + H)+) |
| P2.048 | 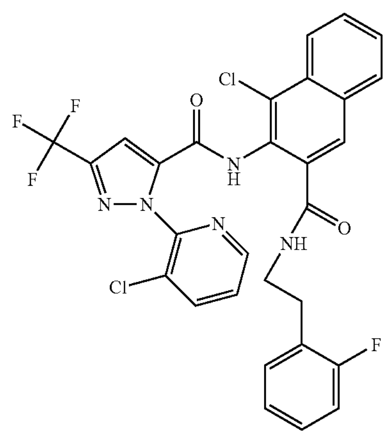 | 616 ((M + H)+) |
| P2.049 | 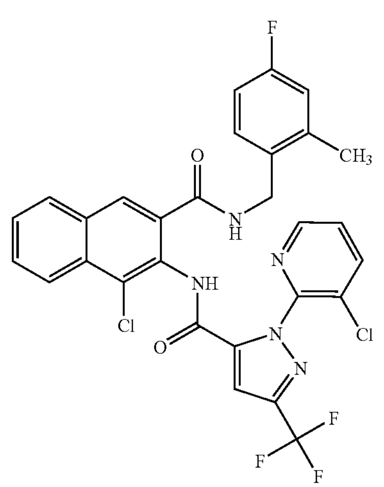 | 616 ((M + H)+) |

TABLE P2-continued

| Comp. Nr. | Structure | Phys. Data (MS., NMR, M. P in ° C.) |
|---|---|---|
| P2.050 | 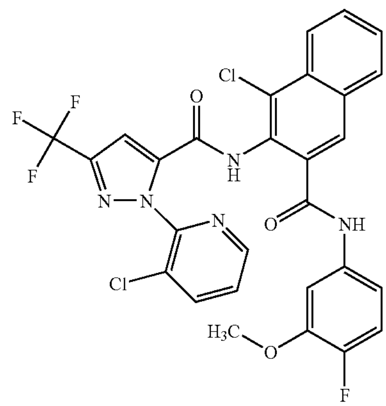 | 618 ((M + H)+) |
| P2.051 | 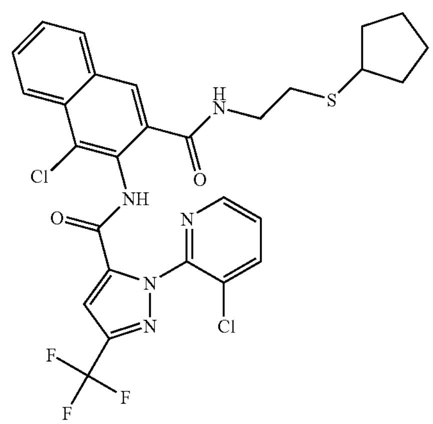 | 622 ((M + H)+) |
| P2.052 | 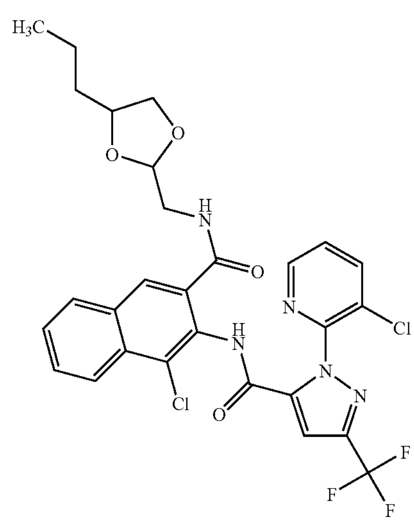 | 622 ((M + H)+) |

TABLE P2-continued

| Comp. Nr. | Structure | Phys. Data (MS., NMR, M. P in °C.) |
| --- | --- | --- |
| P2.053 | 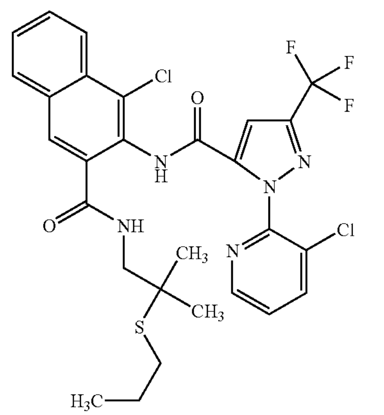 | 624 ((M + H)+) |
| P2.054 | 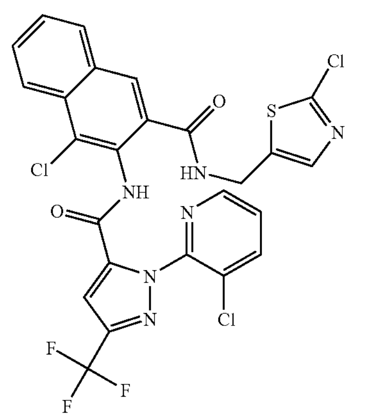 | 625 ((M + H)+) |
| P2.055 | 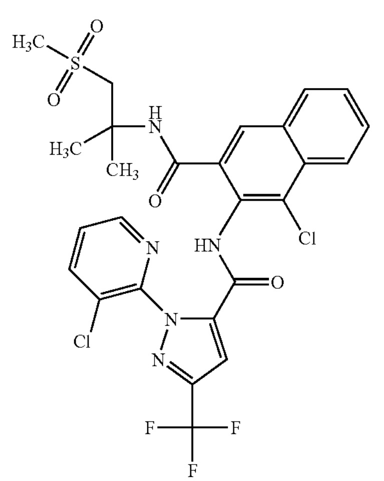 | 628 ((M + H)+) |

TABLE P2-continued
| Comp. Nr. | Structure | Phys. Data (MS., NMR, M. P in ° C.) |
|---|---|---|
| P2.056 | 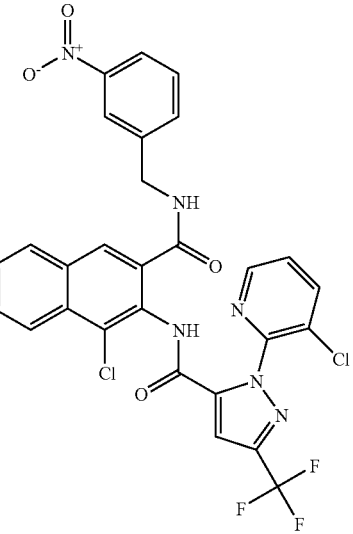 | 629 ((M + H)+) |
| P2.057 | 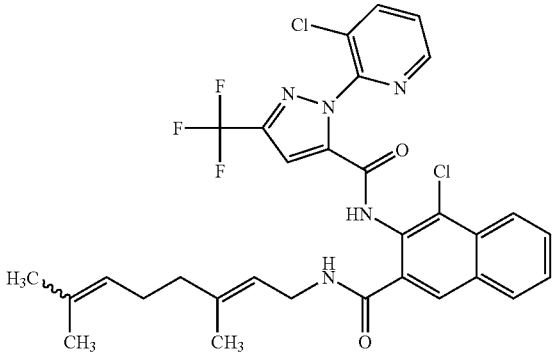 | 630 ((M + H)+) |
| P2.058 | 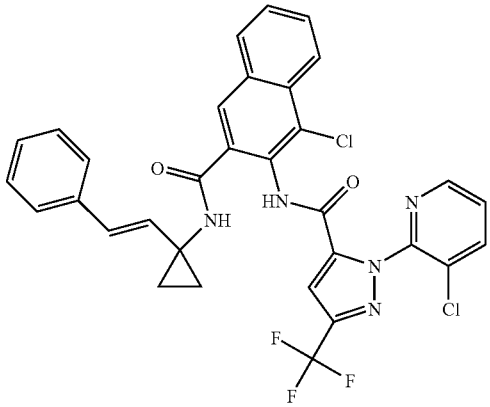 | 636 ((M + H)+) |

TABLE P2-continued

| Comp. Nr. | Structure | Phys. Data (MS., NMR, M. P in °C.) |
|---|---|---|
| P2.059 | 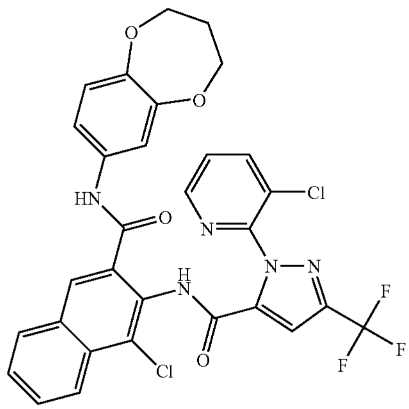 | 642 ((M + H)+) |
| P2.060 | 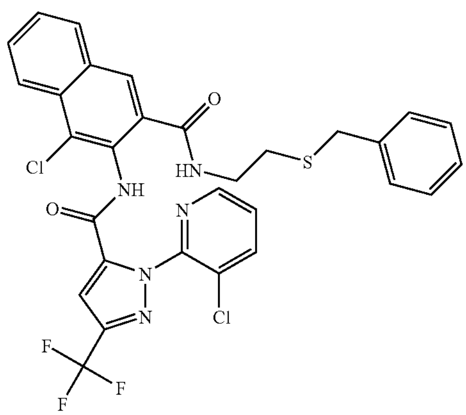 | 644 ((M + H)+) |
| P2.061 | 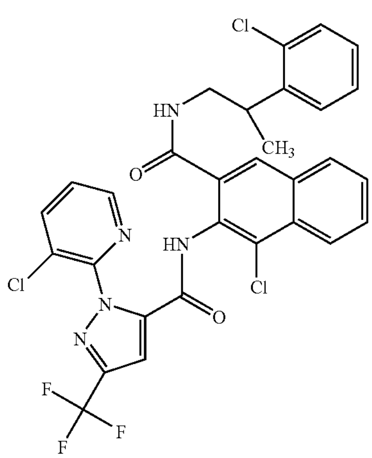 | 646 ((M + H)+) |

TABLE P2-continued

| Comp. Nr. | Structure | Phys. Data (MS., NMR, M. P in ° C.) |
|---|---|---|
| P2.062 | 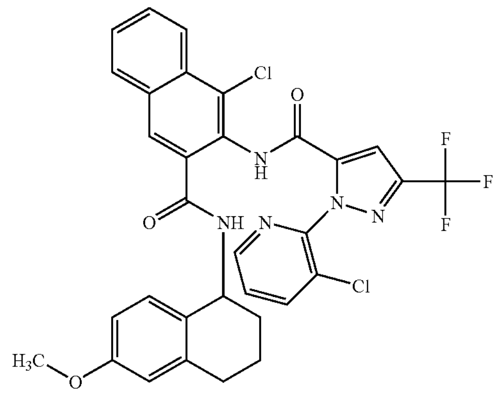 | 654 ((M + H)+) |
| P2.063 | 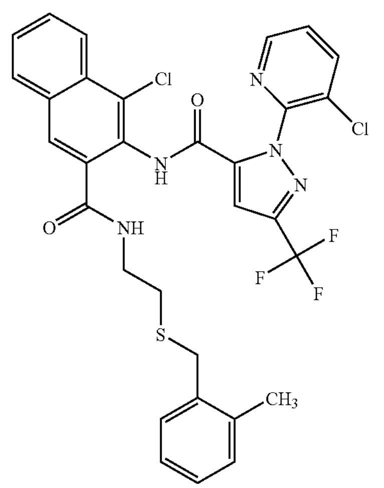 | 658 ((M + H)+) |
| P2.064 | 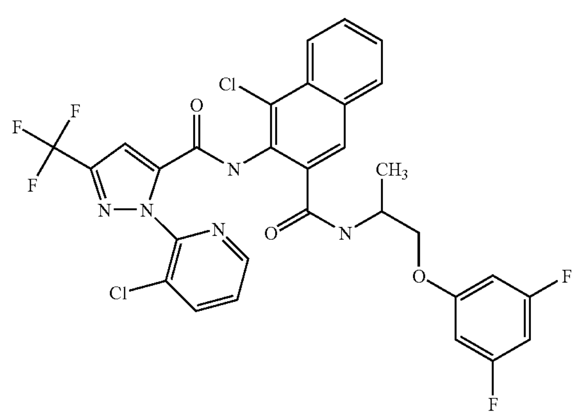 | 664 ((M + H)+) |

TABLE P2-continued

| Comp. Nr. | Structure | Phys. Data (MS., NMR, M. P in ° C.) |
|---|---|---|
| P2.065 | 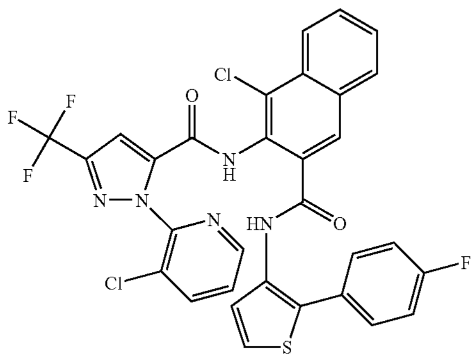 | 670 ((M + H)+) |
| P2.066 | 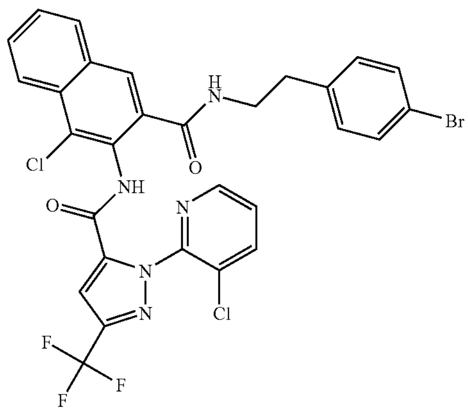 | 676 ((M + H)+) |
| P2.067 | 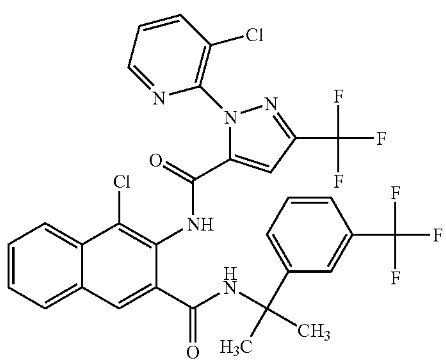 | 680 ((M + H)+) |
| P2.068 | 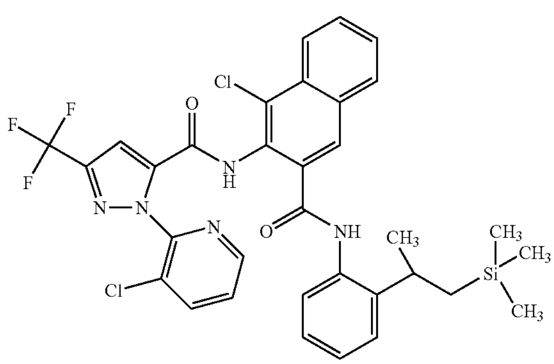 | 684 ((M + H)+) |

TABLE P2-continued

| Comp. Nr. | Structure | Phys. Data (MS., NMR, M. P in °C.) |
|---|---|---|
| P2.069 | 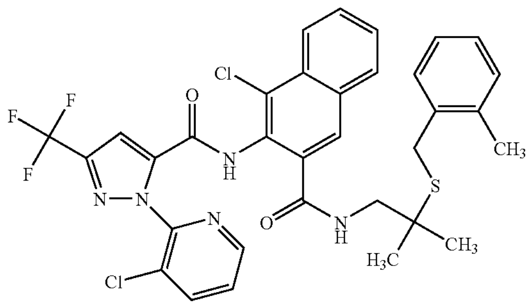 | 686 ((M + H)+) |
| P2.070 | 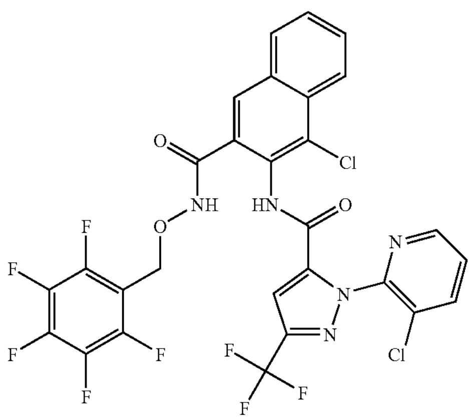 | 690 ((M + H)+) |
| P2.071 | 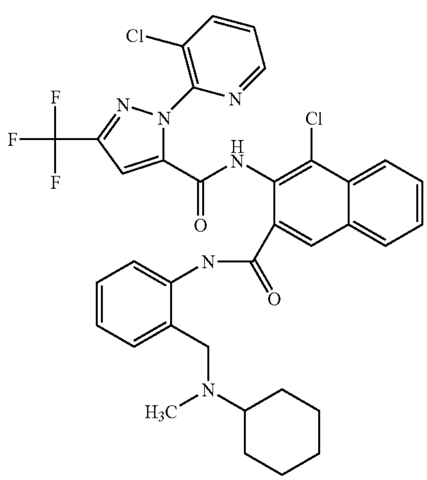 | 695 ((M + H)+) |

TABLE P2-continued
| Comp. Nr. | Structure | Phys. Data (MS., NMR, M. P in ° C.) |
|---|---|---|
| P2.072 | 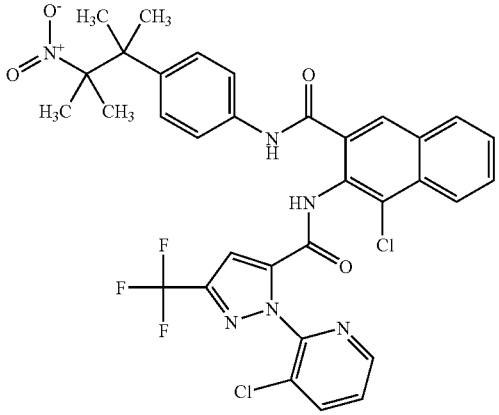 | 699 ((M + H)+) |
| P2.073 | 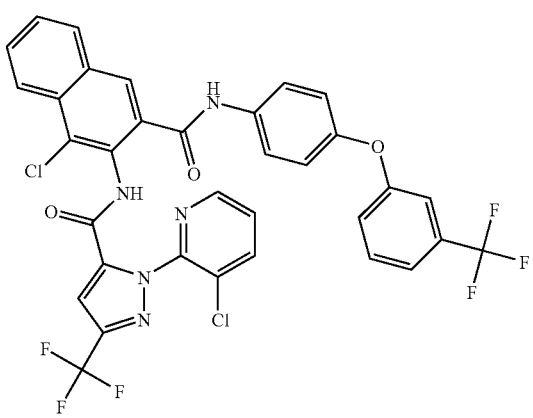 | 730 ((M + H)+) |
| P2.074 | 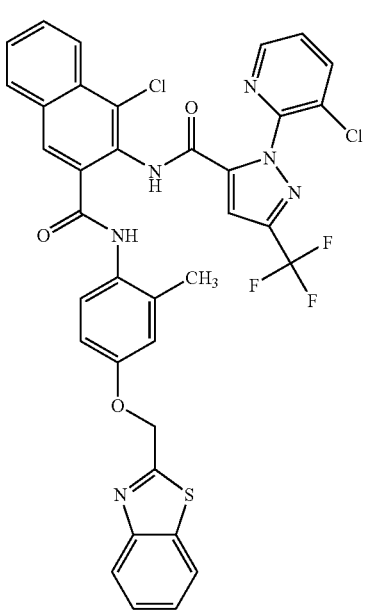 | 747 ((M + H)+) |

TABLE P2-continued

| Comp. Nr. | Structure | Phys. Data (MS., NMR, M. P in °C.) |
|---|---|---|
| P2.075 | 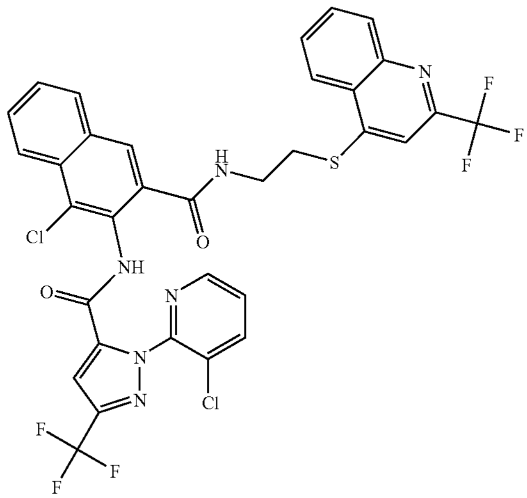 | 749 ((M + H)+) |
| P2.076 (T85.273) | 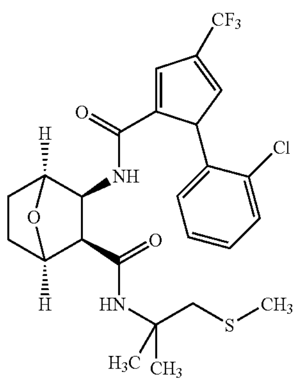 | 459 ((M + H)+) oil |
| P2.077 (T8.1) | 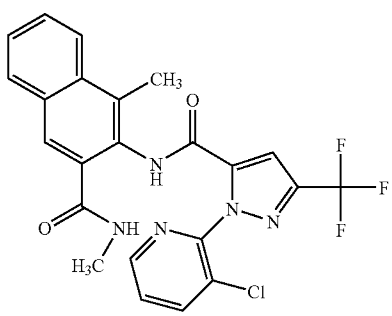 | 488 ((M + H)+) |
| P2.078 | 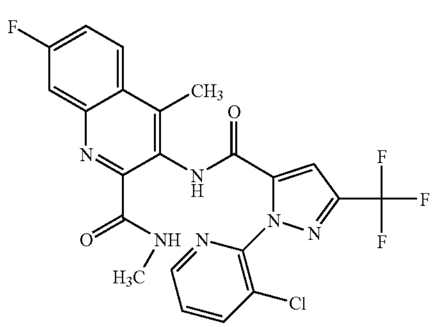 | 507 ((M + H)+) |

TABLE P2-continued

| Comp. Nr. | Structure | Phys. Data (MS., NMR, M. P in °C.) |
|---|---|---|
| P2.079 | 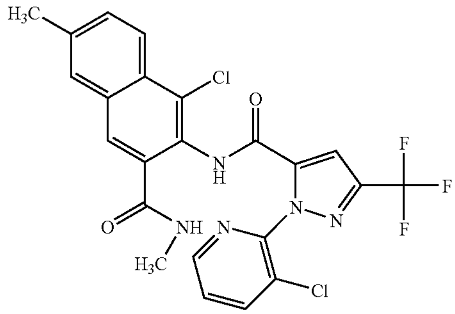 | 522 ((M + H)+) |
| P2.080 | 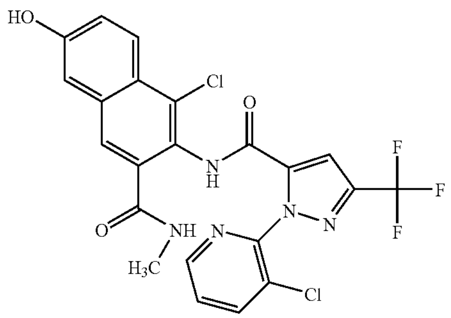 | 524 ((M + H)+) |
| P2.081 (T5.1) | 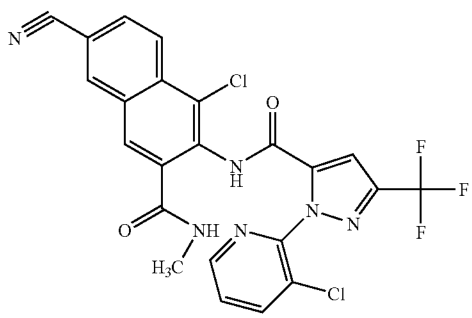 | 533 ((M + H)+) |
| P2.082 | 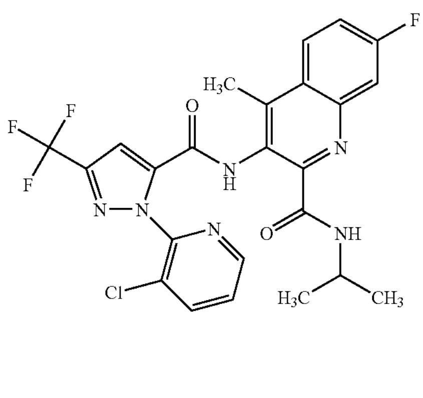 | 535 ((M + H)+) |

TABLE P2-continued

| Comp. Nr. | Structure | Phys. Data (MS., NMR, M. P in °C.) |
|---|---|---|
| P2.083 | 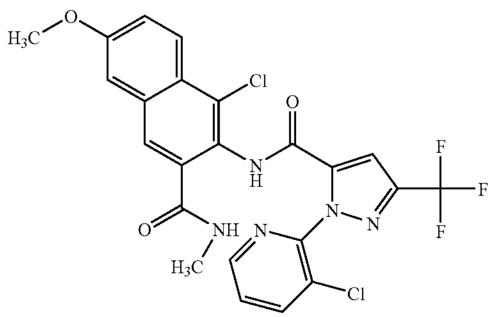 | 538 ((M + H)+) |
| P2.084 (T20.1) | 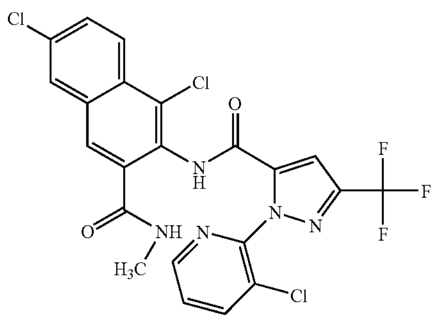 | 544 ((M + H)+) |
| P2.085 (T5.207) | 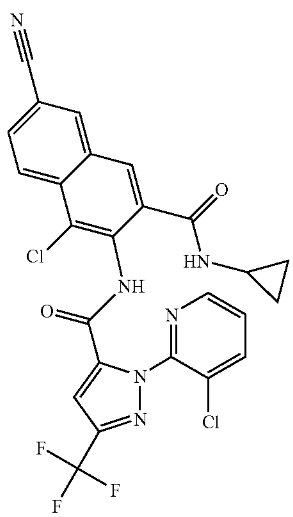 | 559 ((M + H)+) |
| P2.086 (T5.3) | 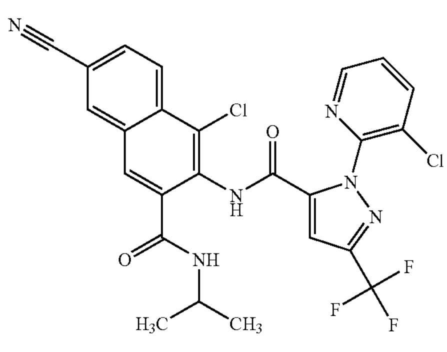 | 561 ((M + H)+) |

TABLE P2-continued
| Comp. Nr. | Structure | Phys. Data (MS., NMR, M. P in ° C.) |
|---|---|---|
| P2.087 (T20.207) | 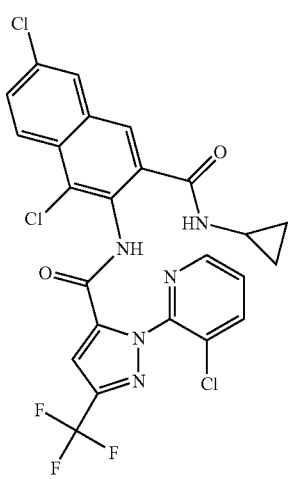 | 568 ((M + H)+) |
| P2.088 (T20.3) | 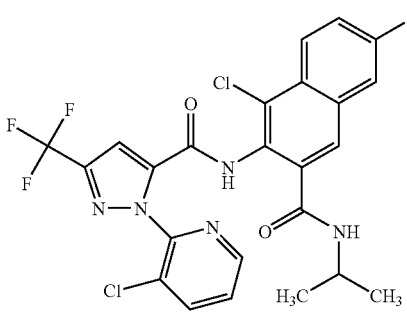 | 570 ((M + H)+) |
| P2.089 | 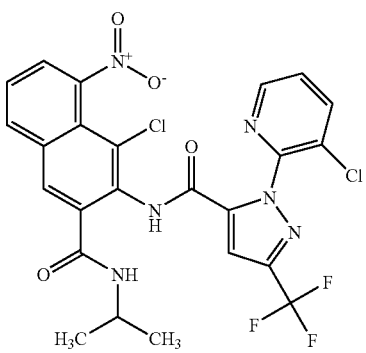 | 581 ((M + H)+) |
| P2.090 | 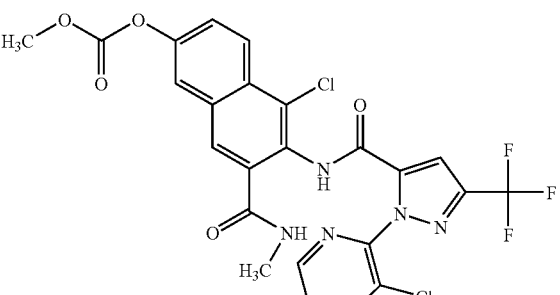 | 582 ((M + H)+) |

TABLE P2-continued

| Comp. Nr. | Structure | Phys. Data (MS., NMR, M. P in ° C.) |
|---|---|---|
| P2.091 | 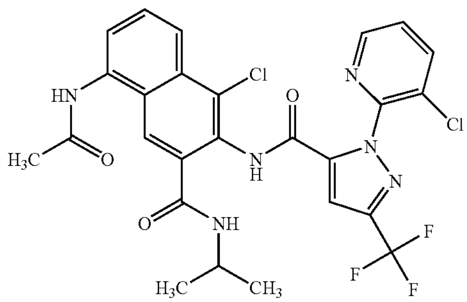 | 593 ((M + H)+) |
| P2.092 (T2.2) | 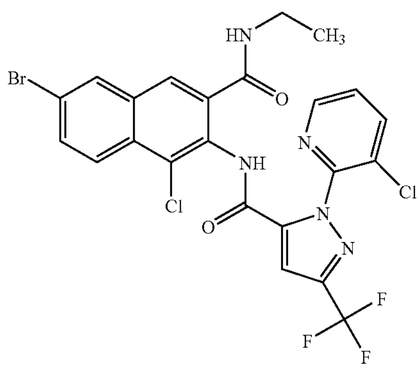 | 602 ((M + H)+) |
| P2.093 (T2.207) | 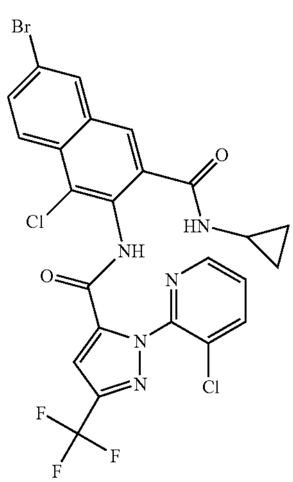 | 612 ((M − 1)−) |

TABLE P2-continued

| Comp. Nr. | Structure | Phys. Data (MS., NMR, M. P in ° C.) |
|---|---|---|
| P2.094 | 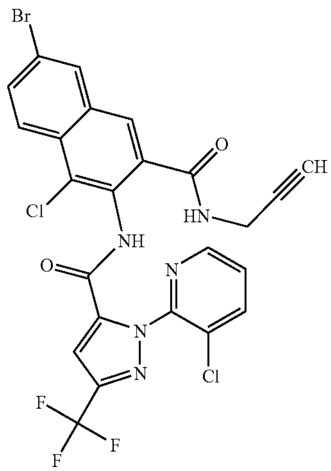 | 612 ((M + H)+) |
| P2.095 | 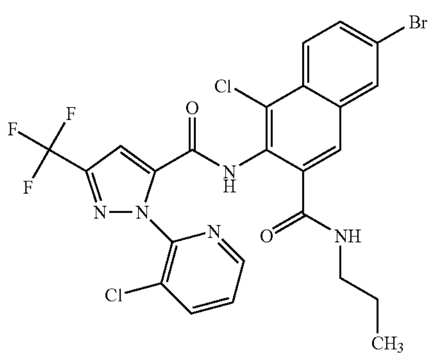 | 614 ((M − 1)−) |
| P2.096 | 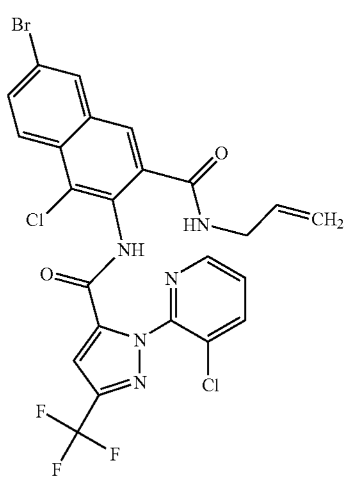 | 614 ((M + H)+) |

TABLE P2-continued

| Comp. Nr. | Structure | Phys. Data (MS., NMR, M. P in ° C.) |
|---|---|---|
| P2.097 | 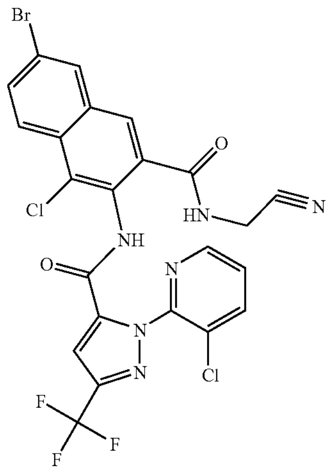 | 627 ((M + H)+) |
| P2.098 | 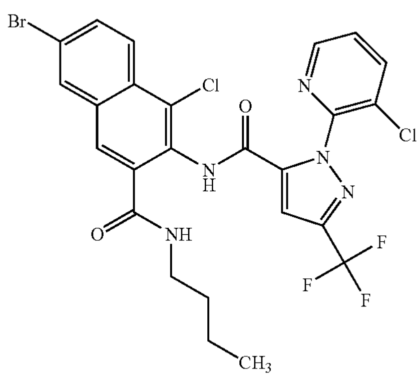 | 628 ((M + H)+) |
| P2.099 | 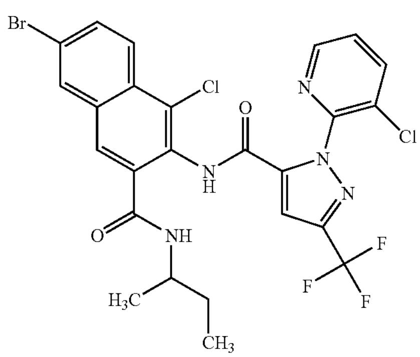 | 628 ((M − 1)−) |

TABLE P2-continued

| Comp. Nr. | Structure | Phys. Data (MS., NMR, M. P in ° C.) |
|---|---|---|
| P2.100 | 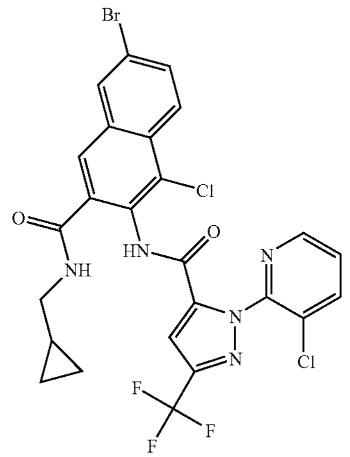 | 628 ((M + H)+) |
| P2.101 | 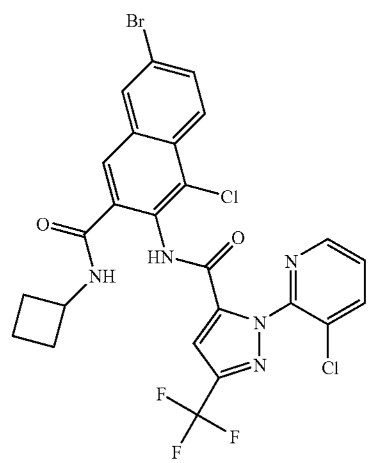 | 628 ((M + H)+) |
| P2.102 | 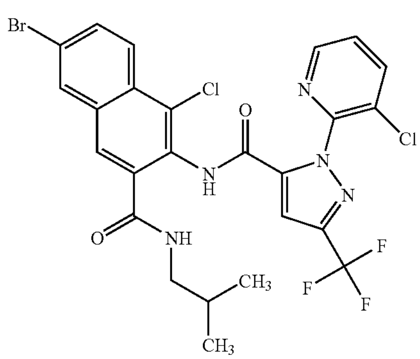 | 630 ((M + H)+) |

TABLE P2-continued

| Comp. Nr. | Structure | Phys. Data (MS., NMR, M. P in ° C.) |
|---|---|---|
| P2.103 | 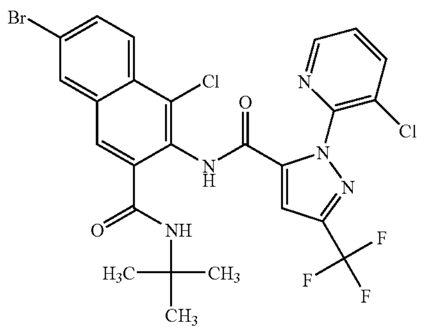 | 630 ((M + H)+) |
| P2.104 (T9.1) | 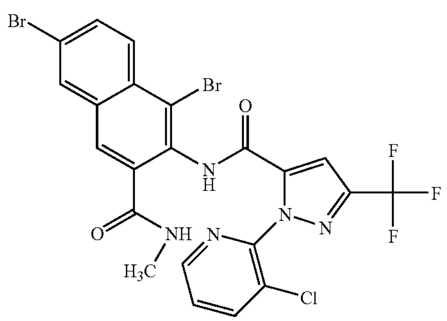 | 632 ((M + H)+) |
| P2.105 | 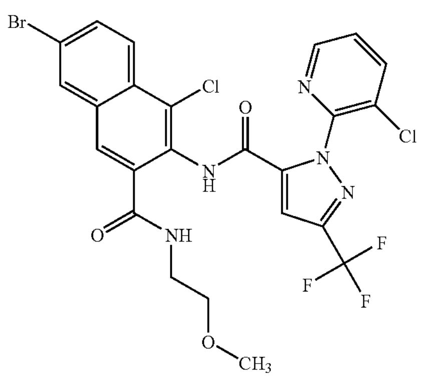 | 632 ((M + H)+) |
| P2.106 | 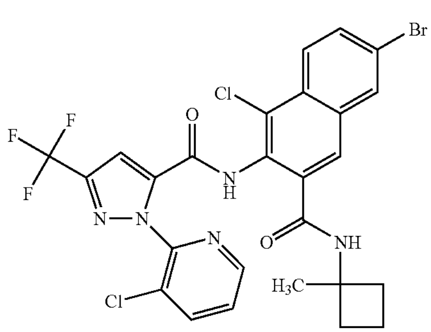 | 642 ((M + H)+) |

TABLE P2-continued

| Comp. Nr. | Structure | Phys. Data (MS., NMR, M. P in ° C.) |
|---|---|---|
| P2.107 | 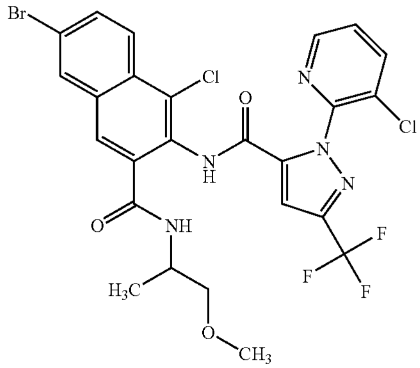 | 646 ((M + H)+) |
| P2.108 | 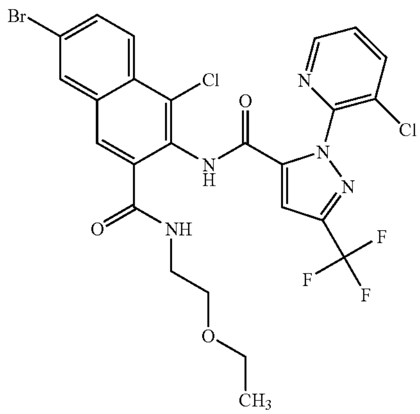 | 646 ((M + H)+) |
| P2.109 (T9.2) | 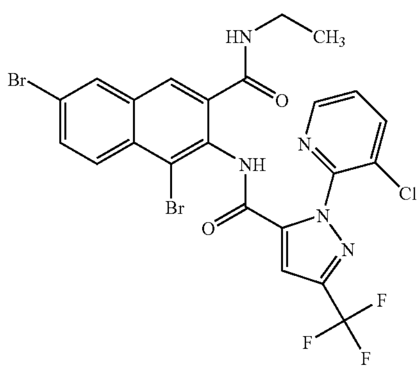 | 646 ((M + H)+) |
| P2.110 | 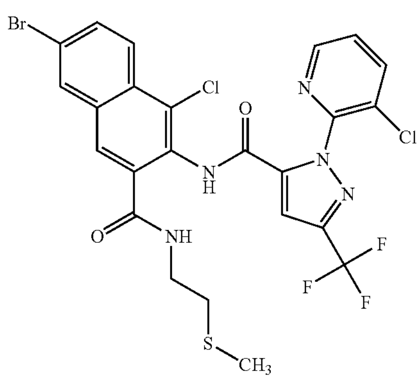 | 648 ((M + H)+) |

TABLE P2-continued

| Comp. Nr. | Structure | Phys. Data (MS., NMR, M. P in °C.) |
|---|---|---|
| P2.111 | (structure) | 656 ((M + H)+) |
| P2.112 (T9.207) | (structure) | 656 ((M + H)+) |
| P2.113 | (structure) | 656 ((M + H)+) |

TABLE P2-continued

| Comp. Nr. | Structure | Phys. Data (MS., NMR, M. P in °C.) |
|---|---|---|
| P2.114 (T9.3) | 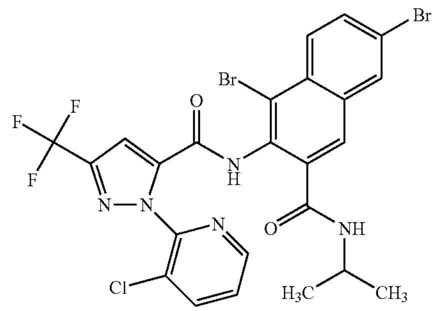 | 660 ((M + H)+) |
| P2.115 | 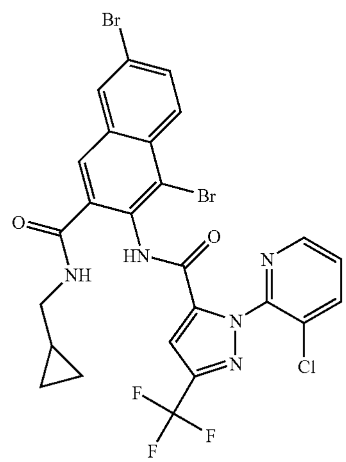 | 670 ((M + H)+) |
| P2.116 | 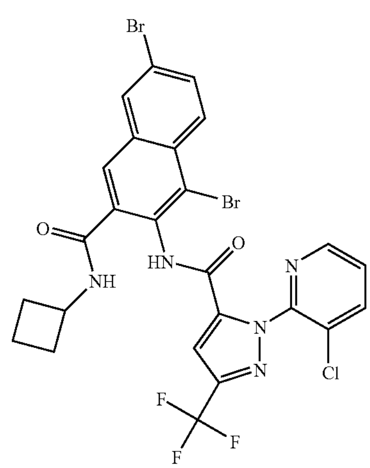 | 670 ((M + H)+) |

TABLE P2-continued

| Comp. Nr. | Structure | Phys. Data (MS., NMR, M. P in ° C.) |
|---|---|---|
| P2.117 | 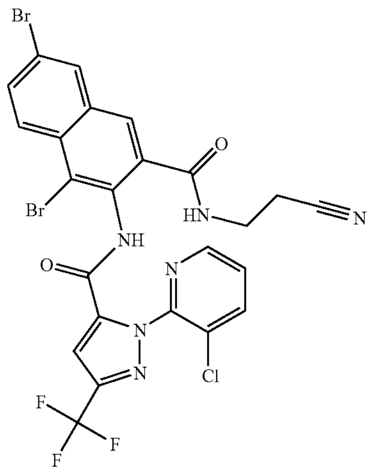 | 671 ((M + H)+) |
| P2.118 | 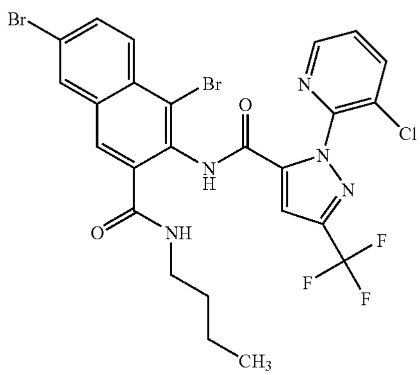 | 672 ((M + H)+) |
| P2.119 (T9.145) | 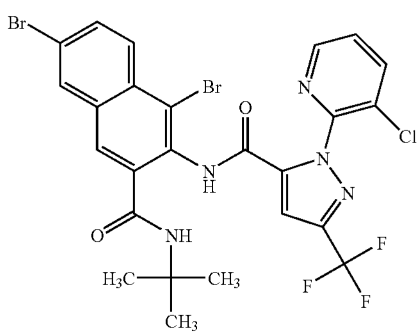 | 672 ((M − 1)−) |
| P2.120 | 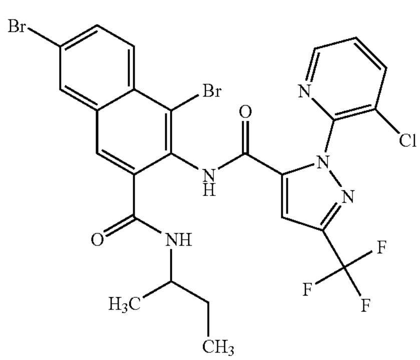 | 674 ((M + H)+) |

TABLE P2-continued

| Comp. Nr. | Structure | Phys. Data (MS., NMR, M. P in °C.) |
|---|---|---|
| P2.121 | 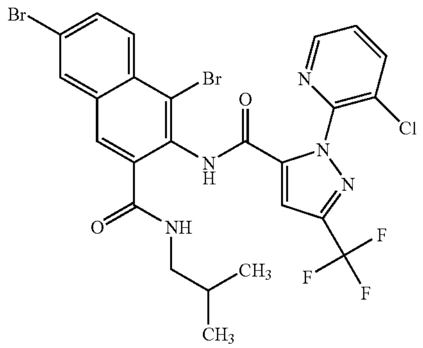 | 674 ((M + H)+) |
| P2.122 | 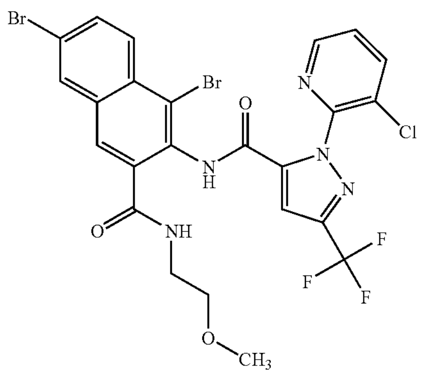 | 676 ((M + H)+) |
| P2.123 | 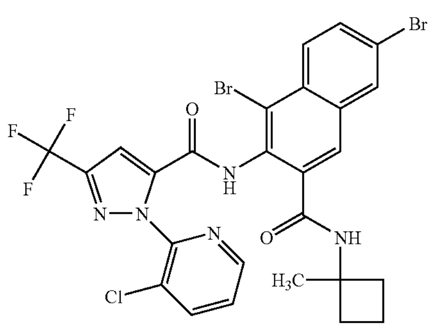 | 686 ((M + H)+) |
| P2.124 | 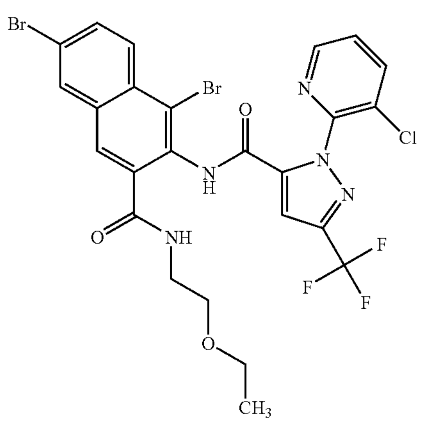 | 688 ((M + H)+) |

TABLE P2-continued
| Comp. Nr. | Structure | Phys. Data (MS., NMR, M. P in ° C.) |
|---|---|---|
| P2.125 | 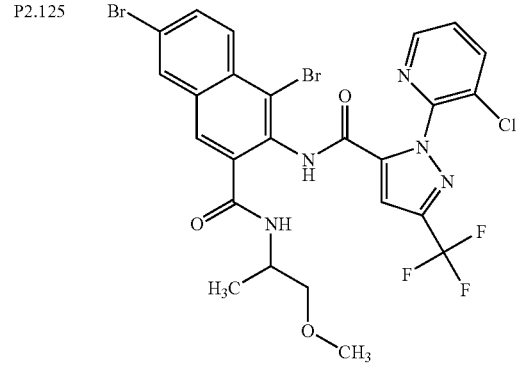 | 690 ((M + H)+) |
| P2.126 | 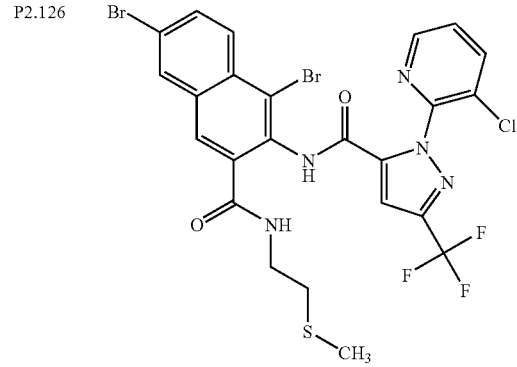 | 692 ((M + H)+) |
| P2.127 | 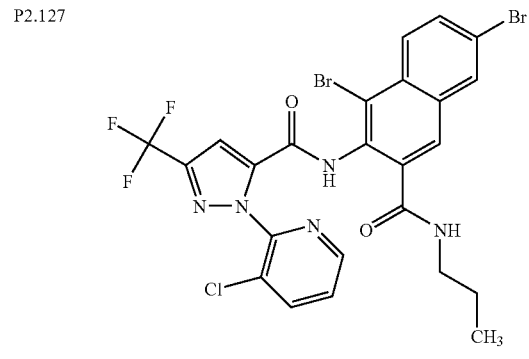 | 0.82-086 (t, 3H), 1.37-1.46 (m, 2H), 3.07-3.12 (m, 2H), 7.64-7.66 (m, 1H), 7.87-7.89 (dd, 1H), 7.88 (s, 1H), 8.07 (s, 1H), 8.13-8.15 (d, 1H), 8.19-8.21 (d, 1H), 8.41-8.42 (d, 1H), 8.48 (br, 1H), 8.51-8.52 (d, 1H) |
| P2.128 | 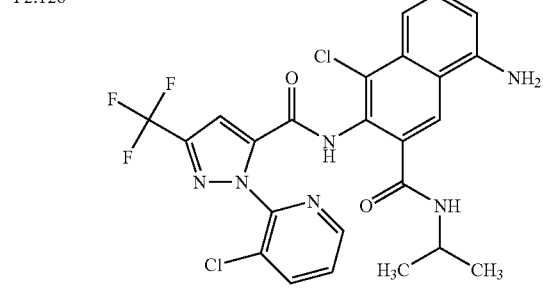 | 1.07-7.08 (d, 6H), 3.90-3.97 (m, 1H), 6.10 (br s, 2H), 6.79-6.80 (d, 1H) 7.33-7.35 (d, 1H), 7.39-7.43 (m, 1H), 7.63-7.66 (m, 1H), 7.88 (s, 1H), 8.00-8.02 (d, 1H), 8.19 (s, 1 H0, 8.19-8.21 (d, 1H), 8.51-8.52 (d, 1H), 10.67 (s, 1H) |

TABLE P2-continued

| Comp. Nr. | Structure | Phys. Data (MS., NMR, M. P in ° C.) |
|---|---|---|
| P2.129 (T85.3) | 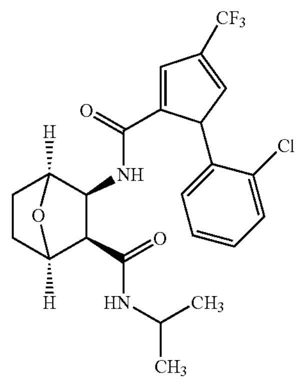 | 220-224° C. |
| P2.130 | 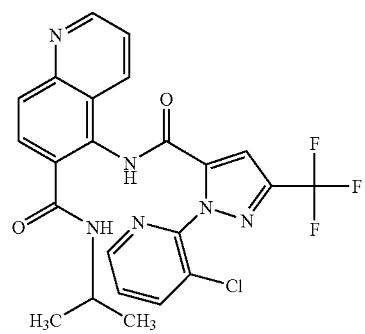 | 503 ((M + H)+) |
| P2.131 (T84.3) | 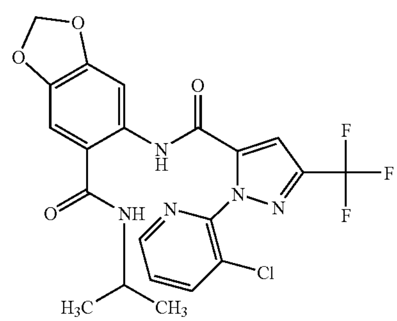 | 496 ((M + H)+) |
| P2.132 | 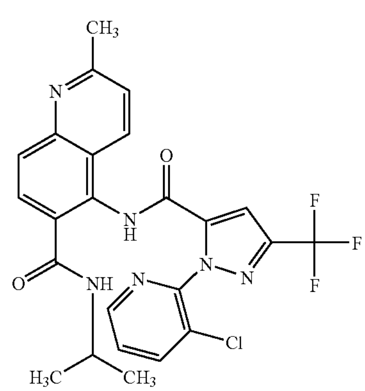 | 517 ((M + H)+) |

TABLE P2-continued

| Comp. Nr. | Structure | Phys. Data (MS., NMR, M. P in ° C.) |
|---|---|---|
| P2.133 | 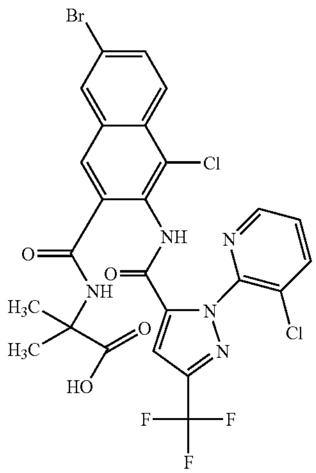 | 658 ((M + H)+) |
| P2.134 | 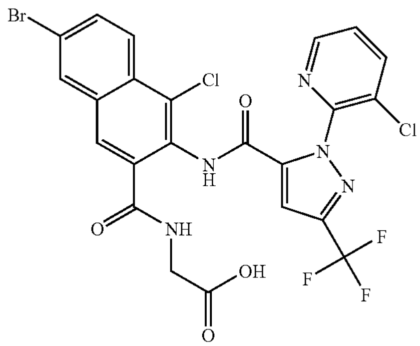 | 630 ((M + H)+) |
| P2.135 | 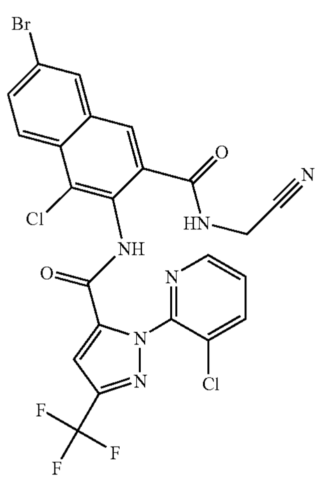 | 611 ((M + H)+) |

TABLE P2-continued

| Comp. Nr. | Structure | Phys. Data (MS., NMR, M. P in ° C.) |
|---|---|---|
| P2.136 (T50.1) | 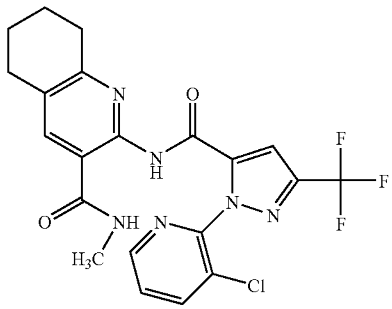 | 145-147° C. |
| P2.137 (T50.3) | 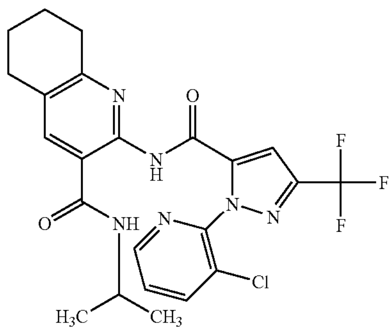 | 143-145° C. |
| P2.138 (T51.3) | 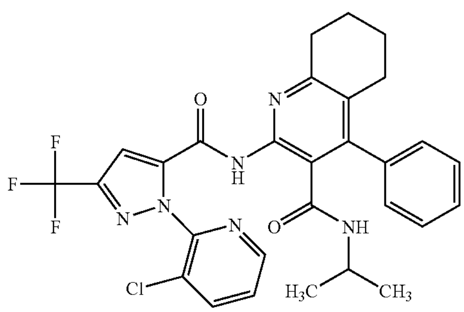 | 146-148° C. |
| P2.139 (T51.1) | 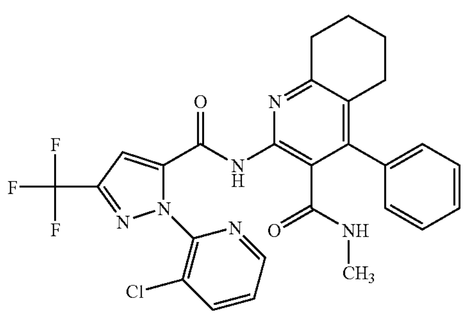 | 165-168° C. |
| P2.140 (T46.1) | 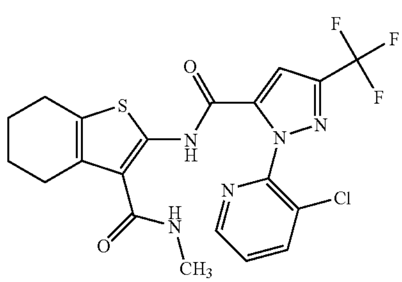 | 261-263° C. |

TABLE P2-continued

| Comp. Nr. | Structure | Phys. Data (MS., NMR, M. P in ° C.) |
|---|---|---|
| P2.141 (T46.1) | 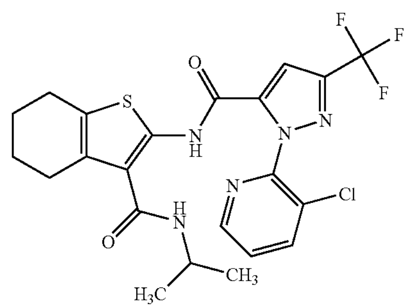 | 246-248° C. |
| P2.142 (T53.3) | 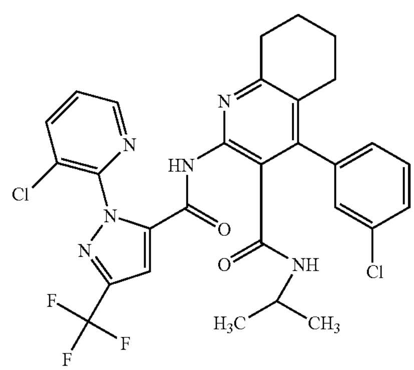 | 259-260° C. |
| P2.143 (T53.1) | 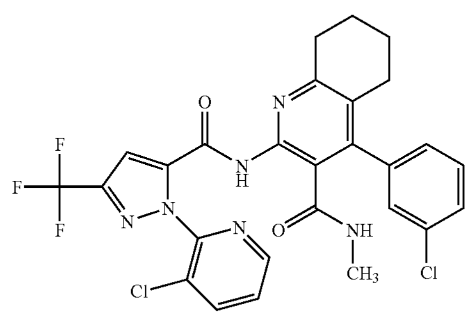 | 183-185° C. |
| P2.144 (T52.3) | 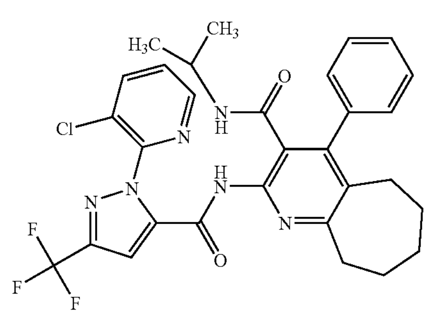 | 269-270° C. |

TABLE P2-continued

| Comp. Nr. | Structure | Phys. Data (MS., NMR, M. P in ° C.) |
|---|---|---|
| P2.145 (T52.1) | 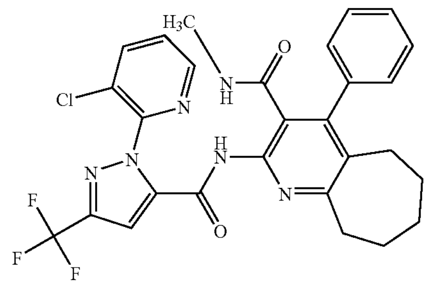 | 211-213° C. |
| P2.146 (T74.3) | 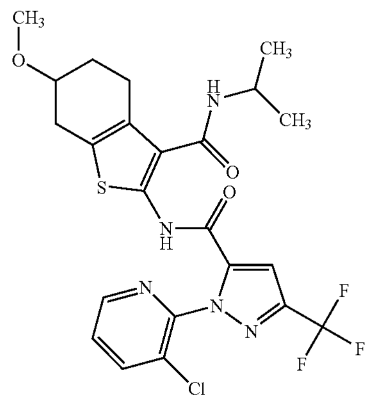 | 206-207° C. |
| P2.147 (T74.1) | 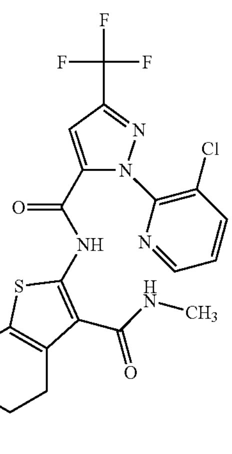 | 133-135° C. |
| P2.148 | 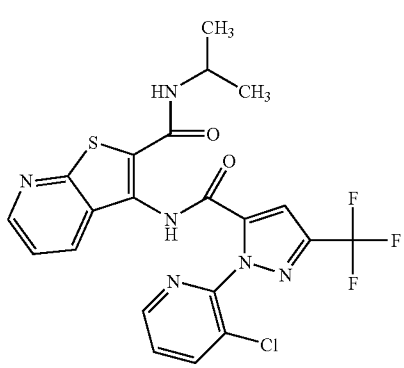 | 212-215° C. |

TABLE P2-continued

| Comp. Nr. | Structure | Phys. Data (MS., NMR, M. P in ° C.) |
|---|---|---|
| P2.149 | 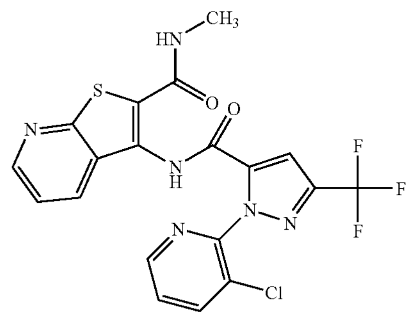 | 253-255° C. |
| P2.150 | 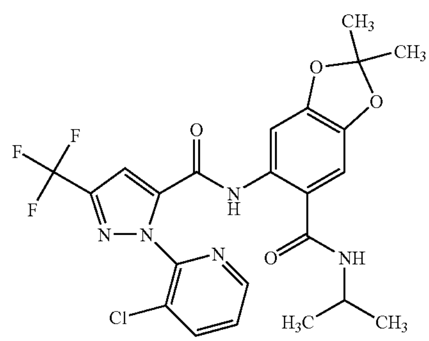 | 284-286° C. |
| P2.151 | 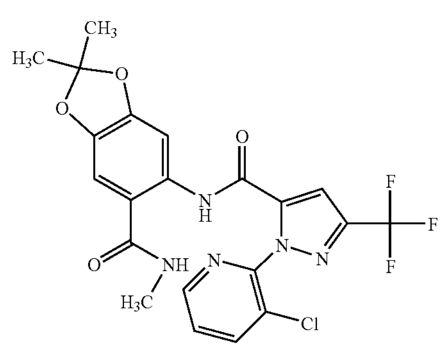 | 273-275° C. |
| P2.152 | 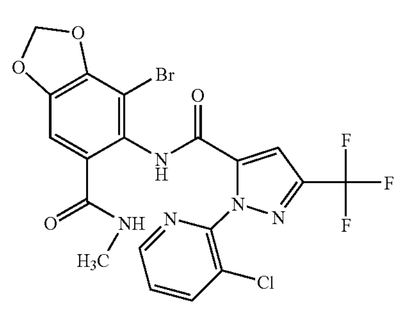 | 255-257° C. |

TABLE P2-continued

| Comp. Nr. | Structure | Phys. Data (MS., NMR, M. P in ° C.) |
|---|---|---|
| P2.153 | 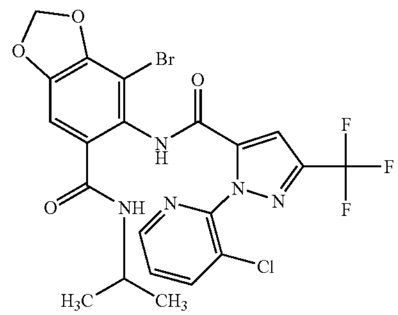 | 274-276° C. |
| P2.154 | 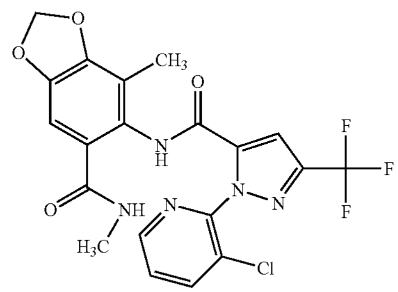 | 255-257° C. |
| P2.155 | 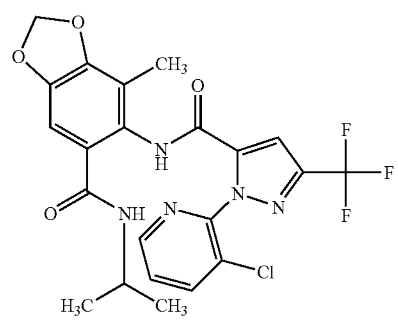 | 267-270° C. |
| P2.156 | 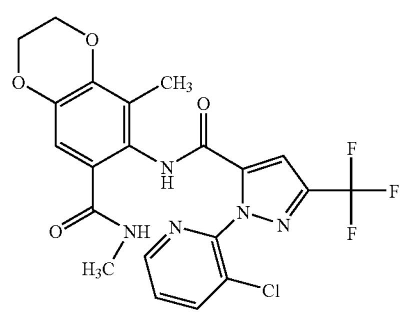 | 265-267° C. |
| P2.157 (T57.1) | 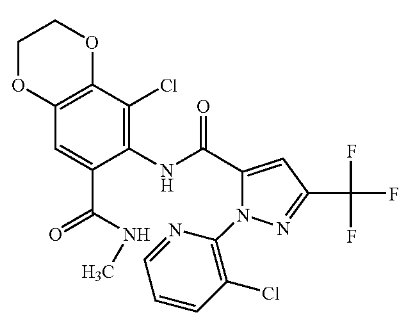 | 257-259° C. |

TABLE P2-continued

| Comp. Nr. | Structure | Phys. Data (MS., NMR, M. P in ° C.) |
|---|---|---|
| P2.158 | 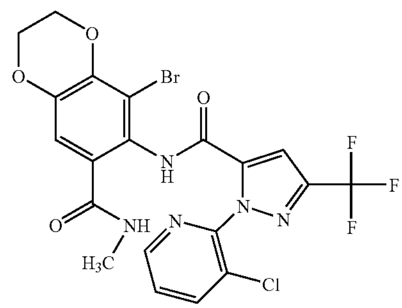 | 253-255° C. |
| P2.159 | 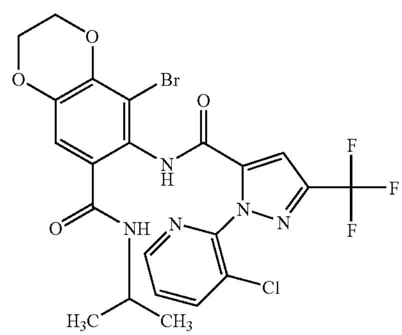 | 274-276° C. |
| P2.160 (T57.3) | 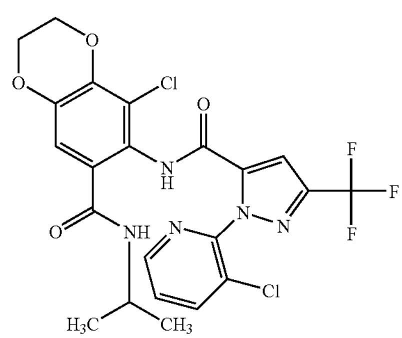 | 265-267° C. |
| P2.161 | 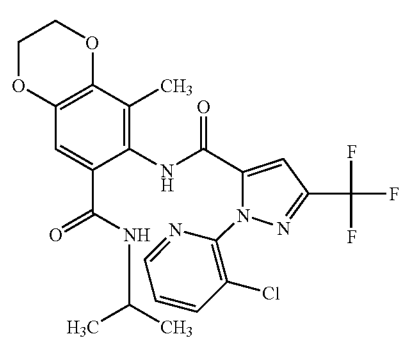 | 265-267° C. |

TABLE P2-continued

| Comp. Nr. | Structure | Phys. Data (MS., NMR, M. P in °C.) |
|---|---|---|
| P2.162 | 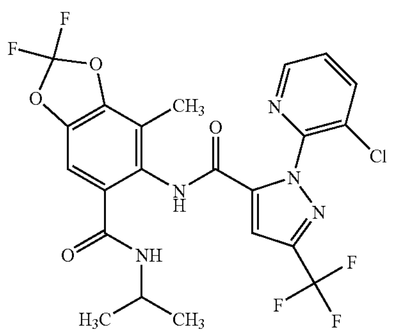 | 254-255° C. |
| P2.163 | 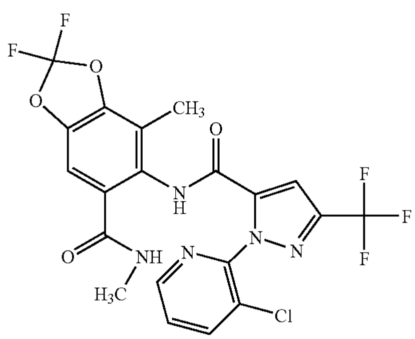 | 272-274° C. |
| P2.164 | 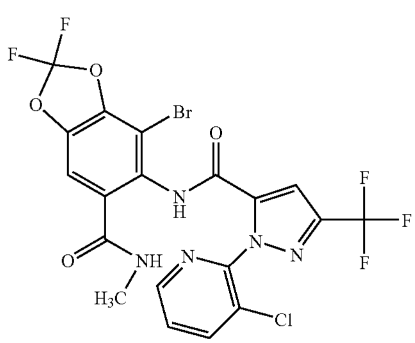 | 234-236° C. |
| P2.165 | 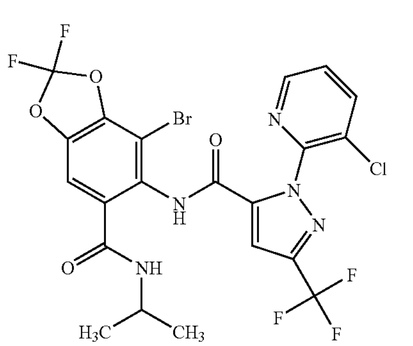 | 284-286° C. |

Example P11

The other compounds listed in the Tables 1 to 85 can also be prepared in a manner analogous to the procedures described in the Examples P1 to P10.

The Table A discloses 338 meanings of the variables $Z_1$, $Z_2$, $R_1$, $R_2$, $R_3$ and $R_4$ in a compound of the formula 1.

TABLE A

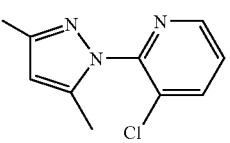
(I)

| Line | $Z_1$ | $Z_2$ | —$R_1$ | $R_2$ | $R_3$ | $R_4$ |
|---|---|---|---|---|---|---|
| A.1 | O | O | 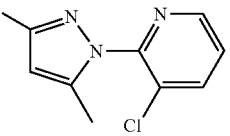 | H | H | $CH_3$ |
| A.2 | O | O | 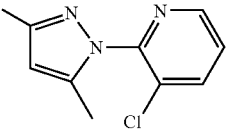 | H | H | $CH_2CH_3$ |
| A.3 | O | O | 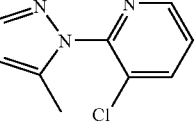 | H | H | $CH(CH_3)_2$ |
| A.4 | O | O | 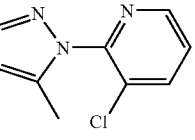 | H | H | $CH_3$ |
| A.5 | O | O | 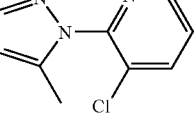 | H | H | $CH_2CH_3$ |
| A.6 | O | O | 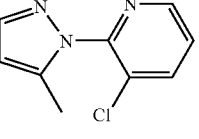 | H | H | $CH(CH_3)_2$ |
| A.7 | O | O |  | H | H | $CH_3$ |

TABLE A-continued
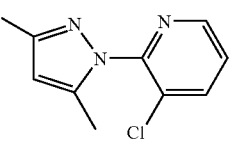
(I)
| Line | $Z_1$ | $Z_2$ | $-R_1$ | $R_2$ | $R_3$ | $R_4$ |
|------|-------|-------|--------|-------|-------|-------|
| A.8  | O | O | 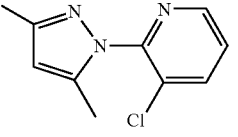 | H | H | $CH_2CH_3$ |
| A.9  | O | O | 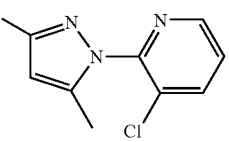 | H | H | $CH(CH_3)_2$ |
| A.10 | O | O | 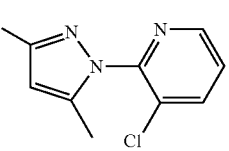 | H | H | $CH_3$ |
| A.11 | O | O | 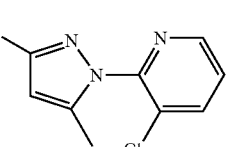 | H | H | $CH_2CH_3$ |
| A.12 | O | O | 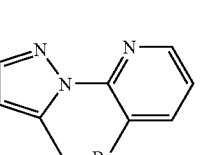 | H | H | $CH(CH_3)_2$ |
| A.13 | O | O | 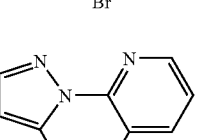 | H | H | $CH_3$ |
| A.14 | O | O | 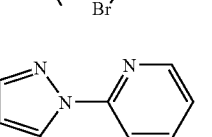 | H | H | $CH_2CH_3$ |
| A.15 | O | O |  | H | H | $CH(CH_3)_2$ |

TABLE A-continued (I)

[Structure of formula (I): central backbone with Z₁=C(R₁)-N(R₈)(R₂) on one side and C(R₇)(R₆)(R₅)-C(...)=Z₂-N(R₄)(R₃) arrangement]

| Line | Z₁ | Z₂ | —R₁ | R₂ | R₃ | R₄ |
|------|----|----|-----|----|----|----|
| A.16 | O | O | 3-Cl, 5-methyl-1-(3-bromopyridin-2-yl)-1H-pyrazol-... | H | H | CH₃ |
| A.17 | O | O | 3-Cl, 5-methyl-1-(3-bromopyridin-2-yl)-1H-pyrazol-... | H | H | CH₂CH₃ |
| A.18 | O | O | 3-Cl, 5-methyl-1-(3-bromopyridin-2-yl)-1H-pyrazol-... | H | H | CH(CH₃)₂ |
| A.19 | O | O | 3-Br, 5-methyl-1-(3-bromopyridin-2-yl)-1H-pyrazol-... | H | H | CH₃ |
| A.20 | O | O | 3-Br, 5-methyl-1-(3-bromopyridin-2-yl)-1H-pyrazol-... | H | H | CH₂CH₃ |
| A.21 | O | O | 3-Br, 5-methyl-1-(3-bromopyridin-2-yl)-1H-pyrazol-... | H | H | CH(CH₃)₂ |
| A.22 | O | O | 3-(F₃CH₂CO), 5-methyl-1-(3-bromopyridin-2-yl)-1H-pyrazol-... | H | H | CH₃ |
| A.23 | O | O | 3-(F₃CH₂CO), 5-methyl-1-(3-bromopyridin-2-yl)-1H-pyrazol-... | H | H | CH₂CH₃ |

TABLE A-continued (I)

[Structure showing compound with Z₁=R₁, R₈, R₇, R₆, R₅, N-R₂, N-R₃, R₄, Z₂ substituents]

| Line | Z₁ | Z₂ | —R₁ | R₂ | R₃ | R₄ |
|------|----|----|-----|----|----|-----|
| A.24 | O | O | F₃CH₂CO-[3-methyl-pyrazol-1-yl]-[3-bromo-pyridin-2-yl] | H | H | CH(CH₃)₂ |
| A.25 | S | S | F₃C-[3-methyl-pyrazol-1-yl]-[3-chloro-pyridin-2-yl] | H | H | CH₃ |
| A.26 | S | S | F₃C-[3-methyl-pyrazol-1-yl]-[3-chloro-pyridin-2-yl] | H | H | CH₂CH₃ |
| A.27 | S | S | F₃C-[3-methyl-pyrazol-1-yl]-[3-chloro-pyridin-2-yl] | H | H | CH(CH₃)₂ |
| A.28 | S | S | Cl-[3-methyl-pyrazol-1-yl]-[3-chloro-pyridin-2-yl] | H | H | CH₃ |
| A.29 | S | S | Cl-[3-methyl-pyrazol-1-yl]-[3-chloro-pyridin-2-yl] | H | H | CH₂CH₃ |
| A.30 | S | S | Cl-[3-methyl-pyrazol-1-yl]-[3-chloro-pyridin-2-yl] | H | H | CH(CH₃)₂ |
| A.31 | S | S | Br-[3-methyl-pyrazol-1-yl]-[3-chloro-pyridin-2-yl] | H | H | CH₃ |

TABLE A-continued (I)

| Line | Z₁ | Z₂ | —R₁ | R₂ | R₃ | R₄ |
|------|----|----|-----|----|----|-----|
| A.32 | S | S | 3-Br-1-(3-Cl-pyridin-2-yl)-5-methylpyrazole | H | H | CH₂CH₃ |
| A.33 | S | S | 3-Br-1-(3-Cl-pyridin-2-yl)-5-methylpyrazole | H | H | CH(CH₃)₂ |
| A.34 | S | S | 3-(F₃CH₂CO)-1-(3-Cl-pyridin-2-yl)-5-methylpyrazole | H | H | CH₃ |
| A.35 | S | S | 3-(F₃CH₂CO)-1-(3-Cl-pyridin-2-yl)-5-methylpyrazole | H | H | CH₂CH₃ |
| A.36 | S | S | 3-(F₃CH₂CO)-1-(3-Cl-pyridin-2-yl)-5-methylpyrazole | H | H | CH(CH₃)₂ |
| A.37 | S | S | 3-F₃C-1-(3-Br-pyridin-2-yl)-5-methylpyrazole | H | H | CH₃ |
| A.38 | S | S | 3-F₃C-1-(3-Br-pyridin-2-yl)-5-methylpyrazole | H | H | CH₂CH₃ |
| A.39 | S | S | 3-F₃C-1-(3-Br-pyridin-2-yl)-5-methylpyrazole | H | H | CH(CH₃)₂ |

TABLE A-continued $$\begin{array}{c} Z_1 = R_1 \\ R_8 \quad | \\ R_7 - \overset{|}{\underset{R_6}{C}} - N \overset{R_2}{\underset{}{\diagdown}} \\ R_6 - \overset{|}{\underset{R_5}{C}} = Z_2 \\ N \overset{}{\underset{R_4}{\diagdown}} R_3 \end{array} \quad (I)$$

| Line | $Z_1$ | $Z_2$ | —$R_1$ | $R_2$ | $R_3$ | $R_4$ |
|------|-------|-------|--------|-------|-------|-------|
| A.40 | S | S | 3-Cl-1-(3-Br-pyridin-2-yl)-5-methyl-pyrazol-4-yl | H | H | $CH_3$ |
| A.41 | S | S | 3-Cl-1-(3-Br-pyridin-2-yl)-5-methyl-pyrazol-4-yl | H | H | $CH_2CH_3$ |
| A.42 | S | S | 3-Cl-1-(3-Br-pyridin-2-yl)-5-methyl-pyrazol-4-yl | H | H | $CH(CH_3)_2$ |
| A.43 | S | S | 3-Br-1-(3-Br-pyridin-2-yl)-5-methyl-pyrazol-4-yl | H | H | $CH_3$ |
| A.44 | S | S | 3-Br-1-(3-Br-pyridin-2-yl)-5-methyl-pyrazol-4-yl | H | H | $CH_2CH_3$ |
| A.45 | S | S | 3-Br-1-(3-Br-pyridin-2-yl)-5-methyl-pyrazol-4-yl | H | H | $CH(CH_3)_2$ |
| A.46 | S | S | 3-($F_3CH_2CO$)-1-(3-Br-pyridin-2-yl)-5-methyl-pyrazol-4-yl | H | H | $CH_3$ |
| A.47 | S | S | 3-($F_3CH_2CO$)-1-(3-Br-pyridin-2-yl)-5-methyl-pyrazol-4-yl | H | H | $CH_2CH_3$ |

TABLE A-continued $$\text{(I)}$$

Structure (I): Core with substituents $Z_1=\text{C}-R_1$ (top), $R_8$, $R_7$ on one carbon attached to $N(R_2)$; $R_6$, $R_5$ on adjacent carbon attached to $C(=Z_2)-N(R_3)(R_4)$.

| Line | $Z_1$ | $Z_2$ | —$R_1$ | $R_2$ | $R_3$ | $R_4$ |
|---|---|---|---|---|---|---|
| A.48 | S | S | F$_3$CH$_2$CO-[3-(pyrazol-3-yloxy)], pyrazole N1-linked to 3-bromo-pyridin-2-yl, 5-methyl | H | H | CH(CH$_3$)$_2$ |
| A.49 | O | S | F$_3$C-[pyrazol-3-yl], N1-linked to 3-chloro-pyridin-2-yl, 5-methyl | H | H | CH$_3$ |
| A.50 | O | S | F$_3$C-[pyrazol-3-yl], N1-linked to 3-chloro-pyridin-2-yl, 5-methyl | H | H | CH$_2$CH$_3$ |
| A.51 | O | S | F$_3$C-[pyrazol-3-yl], N1-linked to 3-chloro-pyridin-2-yl, 5-methyl | H | H | CH(CH$_3$)$_2$ |
| A.52 | O | S | Cl-[pyrazol-3-yl], N1-linked to 3-chloro-pyridin-2-yl, 5-methyl | H | H | CH$_3$ |
| A.53 | O | S | Cl-[pyrazol-3-yl], N1-linked to 3-chloro-pyridin-2-yl, 5-methyl | H | H | CH$_2$CH$_3$ |
| A.54 | O | S | Cl-[pyrazol-3-yl], N1-linked to 3-chloro-pyridin-2-yl, 5-methyl | H | H | CH(CH$_3$)$_2$ |
| A.55 | O | S | Br-[pyrazol-3-yl], N1-linked to 3-chloro-pyridin-2-yl, 5-methyl | H | H | CH$_3$ |

TABLE A-continued

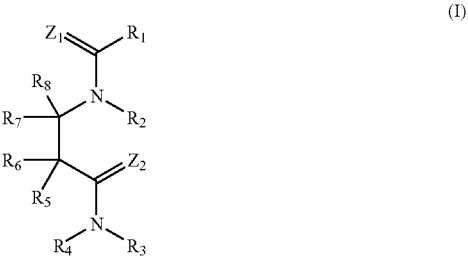

(I)

| Line | $Z_1$ | $Z_2$ | —$R_1$ | $R_2$ | $R_3$ | $R_4$ |
|------|-------|-------|--------|-------|-------|-------|
| A.56 | O | S | Br-pyrazole-pyridine-Cl (3-methyl) | H | H | $CH_2CH_3$ |
| A.57 | O | S | Br-pyrazole-pyridine-Cl (3-methyl) | H | H | $CH(CH_3)_2$ |
| A.58 | O | S | $F_3CH_2CO$-pyrazole-pyridine-Cl | H | H | $CH_3$ |
| A.59 | O | S | $F_3CH_2CO$-pyrazole-pyridine-Cl | H | H | $CH_2CH_3$ |
| A.60 | O | S | $F_3CH_2CO$-pyrazole-pyridine-Cl | H | H | $CH(CH_3)_2$ |
| A.61 | O | S | $F_3C$-pyrazole-pyridine-Br | H | H | $CH_3$ |
| A.62 | O | S | $F_3C$-pyrazole-pyridine-Br | H | H | $CH_2CH_3$ |
| A.63 | O | S | $F_3C$-pyrazole-pyridine-Br | H | H | $CH(CH_3)_2$ |

TABLE A-continued (I)

| Line | $Z_1$ | $Z_2$ | —$R_1$ | $R_2$ | $R_3$ | $R_4$ |
|---|---|---|---|---|---|---|
| A.64 | O | S | 3-Cl, 5-methyl-pyrazolyl-N-(3-Br-pyridin-2-yl) | H | H | $CH_3$ |
| A.65 | O | S | 3-Cl, 5-methyl-pyrazolyl-N-(3-Br-pyridin-2-yl) | H | H | $CH_2CH_3$ |
| A.66 | O | S | 3-Cl, 5-methyl-pyrazolyl-N-(3-Br-pyridin-2-yl) | H | H | $CH(CH_3)_2$ |
| A.67 | O | S | 3-Br, 5-methyl-pyrazolyl-N-(3-Br-pyridin-2-yl) | H | H | $CH_3$ |
| A.68 | O | S | 3-Br, 5-methyl-pyrazolyl-N-(3-Br-pyridin-2-yl) | H | H | $CH_2CH_3$ |
| A.69 | O | S | 3-Br, 5-methyl-pyrazolyl-N-(3-Br-pyridin-2-yl) | H | H | $CH(CH_3)_2$ |
| A.70 | O | S | 3-($F_3CH_2CO$), 5-methyl-pyrazolyl-N-(3-Br-pyridin-2-yl) | H | H | $CH_3$ |
| A.71 | O | S | 3-($F_3CH_2CO$), 5-methyl-pyrazolyl-N-(3-Br-pyridin-2-yl) | H | H | $CH_2CH_3$ |

TABLE A-continued $$\text{(I)}$$

Structure (I): A central backbone with $Z_1=R_1$ group attached via C to N($R_8$)($R_2$), connected to C($R_7$)—C($R_6$,$R_5$)—C($=Z_2$)—N($R_4$)($R_3$).

| Line | $Z_1$ | $Z_2$ | —$R_1$ | $R_2$ | $R_3$ | $R_4$ |
|---|---|---|---|---|---|---|
| A.72 | O | S | 3-(F$_3$CH$_2$CO)-5-methyl-1-(3-bromopyridin-2-yl)-pyrazol-1-yl | H | H | CH(CH$_3$)$_2$ |
| A.73 | S | O | 3-(F$_3$C)-5-methyl-1-(3-chloropyridin-2-yl)-pyrazol-1-yl | H | H | CH$_3$ |
| A.74 | S | O | 3-(F$_3$C)-5-methyl-1-(3-chloropyridin-2-yl)-pyrazol-1-yl | H | H | CH$_2$CH$_3$ |
| A.75 | S | O | 3-(F$_3$C)-5-methyl-1-(3-chloropyridin-2-yl)-pyrazol-1-yl | H | H | CH(CH$_3$)$_2$ |
| A.76 | S | O | 3-Cl-5-methyl-1-(3-chloropyridin-2-yl)-pyrazol-1-yl | H | H | CH$_3$ |
| A.77 | S | O | 3-Cl-5-methyl-1-(3-chloropyridin-2-yl)-pyrazol-1-yl | H | H | CH$_2$CH$_3$ |
| A.78 | S | O | 3-Cl-5-methyl-1-(3-chloropyridin-2-yl)-pyrazol-1-yl | H | H | CH(CH$_3$)$_2$ |
| A.79 | S | O | 3-Br-5-methyl-1-(3-chloropyridin-2-yl)-pyrazol-1-yl | H | H | CH$_3$ |

TABLE A-continued $$\text{(I)}$$

Structure (I): central backbone with $Z_1=\!\!=\!\!C(R_1)$–N($R_8$)($R_2$) on one side via C($R_7$)—C($R_6$)($R_5$) to C($=\!\!Z_2$)—N($R_4$)($R_3$).

| Line | $Z_1$ | $Z_2$ | —$R_1$ | $R_2$ | $R_3$ | $R_4$ |
|---|---|---|---|---|---|---|
| A.80 | S | O | 3-bromo-1-(3-chloropyridin-2-yl)-5-methyl-1H-pyrazol-4-yl | H | H | $CH_2CH_3$ |
| A.81 | S | O | 3-bromo-1-(3-chloropyridin-2-yl)-5-methyl-1H-pyrazol-4-yl | H | H | $CH(CH_3)_2$ |
| A.82 | S | O | 1-(3-chloropyridin-2-yl)-5-methyl-3-(2,2,2-trifluoroethoxy)-1H-pyrazol-4-yl | H | H | $CH_3$ |
| A.83 | S | O | 1-(3-chloropyridin-2-yl)-5-methyl-3-(2,2,2-trifluoroethoxy)-1H-pyrazol-4-yl | H | H | $CH_2CH_3$ |
| A.84 | S | O | 1-(3-chloropyridin-2-yl)-5-methyl-3-(2,2,2-trifluoroethoxy)-1H-pyrazol-4-yl | H | H | $CH(CH_3)_2$ |
| A.85 | S | O | 1-(3-bromopyridin-2-yl)-5-methyl-3-(trifluoromethyl)-1H-pyrazol-4-yl | H | H | $CH_3$ |
| A.86 | S | O | 1-(3-bromopyridin-2-yl)-5-methyl-3-(trifluoromethyl)-1H-pyrazol-4-yl | H | H | $CH_2CH_3$ |
| A.87 | S | O | 1-(3-bromopyridin-2-yl)-5-methyl-3-(trifluoromethyl)-1H-pyrazol-4-yl | H | H | $CH(CH_3)_2$ |

TABLE A-continued
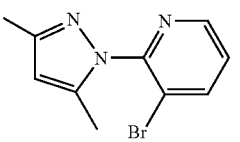
(I)
| Line | $Z_1$ | $Z_2$ | —$R_1$ | $R_2$ | $R_3$ | $R_4$ |
|------|-------|-------|--------|-------|-------|-------|
| A.88 | S | O | 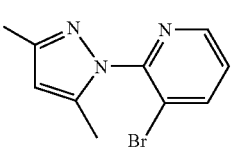 | H | H | $CH_3$ |
| A.89 | S | O | 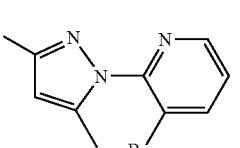 | H | H | $CH_2CH_3$ |
| A.90 | S | O | 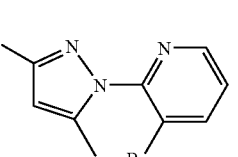 | H | H | $CH(CH_3)_2$ |
| A.91 | S | O | 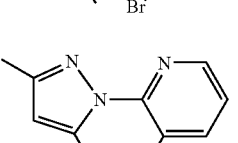 | H | H | $CH_3$ |
| A.92 | S | O | 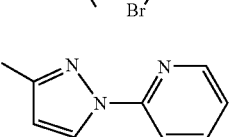 | H | H | $CH_2CH_3$ |
| A.93 | S | O | 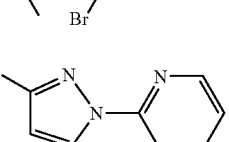 | H | H | $CH(CH_3)_2$ |
| A.94 | S | O | 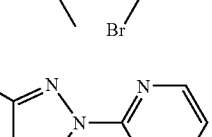 | H | H | $CH_3$ |
| A.95 | S | O |  | H | H | $CH_2CH_3$ |

TABLE A-continued (I)

| Line | $Z_1$ | $Z_2$ | —$R_1$ | $R_2$ | $R_3$ | $R_4$ |
|---|---|---|---|---|---|---|
| A.96 | S | O | F₃CH₂CO-[3-bromo-pyridin-2-yl-5-methylpyrazol-3-yl] | H | H | CH(CH₃)₂ |
| A.97 | O | O | F₃C-[3-chloro-pyridin-2-yl-5-methylpyrazol-3-yl] | CH₃ | H | CH₃ |
| A.98 | O | O | F₃C-[3-chloro-pyridin-2-yl-5-methylpyrazol-3-yl] | CH₃ | H | CH₂CH₃ |
| A.99 | O | O | F₃C-[3-chloro-pyridin-2-yl-5-methylpyrazol-3-yl] | CH₃ | H | CH(CH₃)₂ |
| A.100 | O | O | Cl-[3-chloro-pyridin-2-yl-5-methylpyrazol-3-yl] | CH₃ | H | CH₃ |
| A.101 | O | O | Cl-[3-chloro-pyridin-2-yl-5-methylpyrazol-3-yl] | CH₃ | H | CH₂CH₃ |
| A.102 | O | O | Cl-[3-chloro-pyridin-2-yl-5-methylpyrazol-3-yl] | CH₃ | H | CH(CH₃)₂ |
| A.103 | O | O | Br-[3-chloro-pyridin-2-yl-5-methylpyrazol-3-yl] | CH₃ | H | CH₃ |

TABLE A-continued
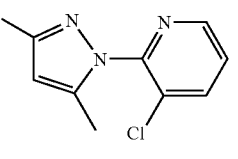
(I)
| Line | $Z_1$ | $Z_2$ | —$R_1$ | $R_2$ | $R_3$ | $R_4$ |
|---|---|---|---|---|---|---|
| A.104 | O | O | 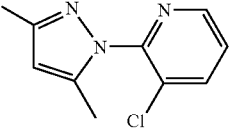 | $CH_3$ | H | $CH_2CH_3$ |
| A.105 | O | O | 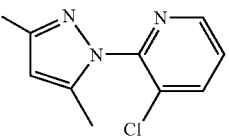 | $CH_3$ | H | $CH(CH_3)_2$ |
| A.106 | O | O | 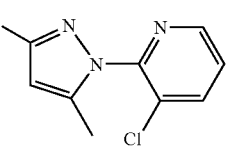 | $CH_3$ | H | $CH_3$ |
| A.107 | O | O | 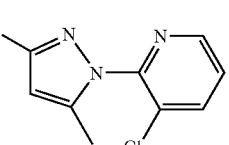 | $CH_3$ | H | $CH_2CH_3$ |
| A.108 | O | O | 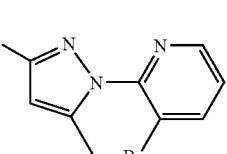 | $CH_3$ | H | $CH(CH_3)_2$ |
| A.109 | O | O | 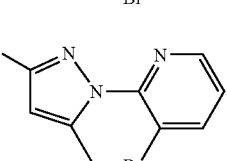 | $CH_3$ | H | $CH_3$ |
| A.110 | O | O | 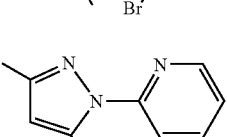 | $CH_3$ | H | $CH_2CH_3$ |
| A.111 | O | O |  | $CH_3$ | H | $CH(CH_3)_2$ |

TABLE A-continued

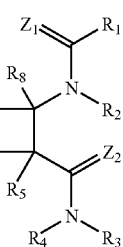

(I)

| Line | $Z_1$ | $Z_2$ | —$R_1$ | $R_2$ | $R_3$ | $R_4$ |
|---|---|---|---|---|---|---|
| A.112 | O | O | Cl-pyrazole-pyridine(Br,CH3) | CH$_3$ | H | CH$_3$ |
| A.113 | O | O | Cl-pyrazole-pyridine(Br,CH3) | CH$_3$ | H | CH$_2$CH$_3$ |
| A.114 | O | O | Cl-pyrazole-pyridine(Br,CH3) | CH$_3$ | H | CH(CH$_3$)$_2$ |
| A.115 | O | O | Br-pyrazole-pyridine(Br,CH3) | CH$_3$ | H | CH$_3$ |
| A.116 | O | O | Br-pyrazole-pyridine(Br,CH3) | CH$_3$ | H | CH$_2$CH$_3$ |
| A.117 | O | O | Br-pyrazole-pyridine(Br,CH3) | CH$_3$ | H | CH(CH$_3$)$_2$ |
| A.118 | O | O | F$_3$CH$_2$CO-pyrazole-pyridine(Br,CH3) | CH$_3$ | H | CH$_3$ |
| A.119 | O | O | F$_3$CH$_2$CO-pyrazole-pyridine(Br,CH3) | CH$_3$ | H | CH$_2$CH$_3$ |

TABLE A-continued $$\text{(I)}$$

Structure of formula (I): central chain with $Z_1=C-R_1$ attached to $N(R_8)(R_2)$ via a carbon bearing $R_7$; that carbon connects to another carbon bearing $R_6, R_5$ which bears $C(=Z_2)-N(R_4)(R_3)$.

| Line | $Z_1$ | $Z_2$ | —$R_1$ | $R_2$ | $R_3$ | $R_4$ |
|---|---|---|---|---|---|---|
| A.120 | O | O | F$_3$CH$_2$CO-(3-pyrazolyl, 5-methyl, 1-(3-bromo-2-pyridinyl)) | CH$_3$ | H | CH(CH$_3$)$_2$ |
| A.121 | O | O | F$_3$C-(3-pyrazolyl, 5-methyl, 1-(3-chloro-2-pyridinyl)) | H | CH$_3$ | CH$_3$ |
| A.122 | O | O | F$_3$C-(3-pyrazolyl, 5-methyl, 1-(3-chloro-2-pyridinyl)) | H | CH$_3$ | CH$_2$CH$_3$ |
| A.123 | O | O | F$_3$C-(3-pyrazolyl, 5-methyl, 1-(3-chloro-2-pyridinyl)) | H | CH$_3$ | CH(CH$_3$)$_2$ |
| A.124 | O | O | Cl-(3-pyrazolyl, 5-methyl, 1-(3-chloro-2-pyridinyl)) | H | CH$_3$ | CH$_3$ |
| A.125 | O | O | Cl-(3-pyrazolyl, 5-methyl, 1-(3-chloro-2-pyridinyl)) | H | CH$_3$ | CH$_2$CH$_3$ |
| A.126 | O | O | Cl-(3-pyrazolyl, 5-methyl, 1-(3-chloro-2-pyridinyl)) | H | CH$_3$ | CH(CH$_3$)$_2$ |
| A.127 | O | O | Br-(3-pyrazolyl, 5-methyl, 1-(3-chloro-2-pyridinyl)) | H | CH$_3$ | CH$_3$ |

TABLE A-continued (I)

| Line | $Z_1$ | $Z_2$ | —$R_1$ | $R_2$ | $R_3$ | $R_4$ |
|---|---|---|---|---|---|---|
| A.128 | O | O | Br-pyrazole-pyridine-Cl (5-methyl) | H | $CH_3$ | $CH_2CH_3$ |
| A.129 | O | O | Br-pyrazole-pyridine-Cl (5-methyl) | H | $CH_3$ | $CH(CH_3)_2$ |
| A.130 | O | O | $F_3CH_2CO$-pyrazole-pyridine-Cl (5-methyl) | H | $CH_3$ | $CH_3$ |
| A.131 | O | O | $F_3CH_2CO$-pyrazole-pyridine-Cl (5-methyl) | H | $CH_3$ | $CH_2CH_3$ |
| A.132 | O | O | $F_3CH_2CO$-pyrazole-pyridine-Cl (5-methyl) | H | $CH_3$ | $CH(CH_3)_2$ |
| A.133 | O | O | $F_3C$-pyrazole-pyridine-Br (5-methyl) | H | $CH_3$ | $CH_3$ |
| A.134 | O | O | $F_3C$-pyrazole-pyridine-Br (5-methyl) | H | $CH_3$ | $CH_2CH_3$ |
| A.135 | O | O | $F_3C$-pyrazole-pyridine-Br (5-methyl) | H | $CH_3$ | $CH(CH_3)_2$ |

TABLE A-continued

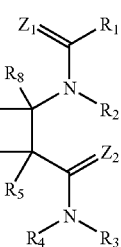

(I)

| Line | $Z_1$ | $Z_2$ | —$R_1$ | $R_2$ | $R_3$ | $R_4$ |
|---|---|---|---|---|---|---|
| A.136 | O | O | Cl-pyrazole-pyridine-Br (methyl) | H | CH$_3$ | CH$_3$ |
| A.137 | O | O | Cl-pyrazole-pyridine-Br (methyl) | H | CH$_3$ | CH$_2$CH$_3$ |
| A.138 | O | O | Cl-pyrazole-pyridine-Br (methyl) | H | CH$_3$ | CH(CH$_3$)$_2$ |
| A.139 | O | O | Br-pyrazole-pyridine-Br (methyl) | H | CH$_3$ | CH$_3$ |
| A.140 | O | O | Br-pyrazole-pyridine-Br (methyl) | H | CH$_3$ | CH$_2$CH$_3$ |
| A.141 | O | O | Br-pyrazole-pyridine-Br (methyl) | H | CH$_3$ | CH(CH$_3$)$_2$ |
| A.142 | O | O | F$_3$CH$_2$CO-pyrazole-pyridine-Br (methyl) | H | CH$_3$ | CH$_3$ |
| A.143 | O | O | F$_3$CH$_2$CO-pyrazole-pyridine-Br (methyl) | H | CH$_3$ | CH$_2$CH$_3$ |

TABLE A-continued (I)

[Structure of formula (I) showing Z₁=C(R₁)-N(R₈)(R₂) group attached via R₇/R₈ carbon to R₅/R₆ carbon bearing C(=Z₂)-N(R₄)(R₃)]

| Line | $Z_1$ | $Z_2$ | —$R_1$ | $R_2$ | $R_3$ | $R_4$ |
|---|---|---|---|---|---|---|
| A.144 | O | O | F₃CH₂CO-[3-(pyrazol-1-yl)-5-methyl, N-linked to 3-bromopyridin-2-yl] | H | CH₃ | CH(CH₃)₂ |
| A.145 | O | O | F₃C-[3-(pyrazol-1-yl)-5-methyl, N-linked to 3-chloropyridin-2-yl] | H | H | C(CH₃)₃ |
| A.146 | O | O | Cl-[3-(pyrazol-1-yl)-5-methyl, N-linked to 3-chloropyridin-2-yl] | H | H | C(CH₃)₃ |
| A.147 | O | O | Br-[3-(pyrazol-1-yl)-5-methyl, N-linked to 3-chloropyridin-2-yl] | H | H | C(CH₃)₃ |
| A.148 | O | O | F₃CH₂CO-[3-(pyrazol-1-yl)-5-methyl, N-linked to 3-chloropyridin-2-yl] | H | H | C(CH₃)₃ |
| A.149 | O | O | F₃C-[3-(pyrazol-1-yl)-5-methyl, N-linked to 3-bromopyridin-2-yl] | H | H | C(CH₃)₃ |
| A.150 | O | O | Cl-[3-(pyrazol-1-yl)-5-methyl, N-linked to 3-bromopyridin-2-yl] | H | H | C(CH₃)₃ |
| A.151 | O | O | Br-[3-(pyrazol-1-yl)-5-methyl, N-linked to 3-bromopyridin-2-yl] | H | H | C(CH₃)₃ |

TABLE A-continued (I)

[Structure: Compound of formula (I) with $Z_1$=$R_1$ attached via double bond to C-N, with substituents $R_8$, $R_7$, $R_6$, $R_5$ on carbon chain and $N(R_2)$, $N(R_3)(R_4)$ groups, with $Z_2$ double bond]

| Line | $Z_1$ | $Z_2$ | —$R_1$ | $R_2$ | $R_3$ | $R_4$ |
|---|---|---|---|---|---|---|
| A.152 | O | O | F$_3$CH$_2$CO-[3-(pyrazolyl)]-1-(3-bromopyridin-2-yl)-5-methyl | H | H | C(CH$_3$)$_3$ |
| A.153 | O | O | F$_3$C-[3-(pyrazolyl)]-1-(2-methylphenyl)-5-methyl | H | H | CH$_3$ |
| A.154 | O | O | F$_3$C-[3-(pyrazolyl)]-1-(2-methylphenyl)-5-methyl | H | H | CH$_2$CH$_3$ |
| A.155 | O | O | F$_3$C-[3-(pyrazolyl)]-1-(2-methylphenyl)-5-methyl | H | H | CH(CH$_3$)$_2$ |
| A.156 | O | O | Cl-[3-(pyrazolyl)]-1-(2-methylphenyl)-5-methyl | H | H | CH$_3$ |
| A.157 | O | O | Cl-[3-(pyrazolyl)]-1-(2-methylphenyl)-5-methyl | H | H | CH$_2$CH$_3$ |
| A.158 | O | O | Cl-[3-(pyrazolyl)]-1-(2-methylphenyl)-5-methyl | H | H | CH(CH$_3$)$_2$ |
| A.159 | O | O | Br-[3-(pyrazolyl)]-1-(2-methylphenyl)-5-methyl | H | H | CH$_3$ |

TABLE A-continued $$(I)$$

| Line | $Z_1$ | $Z_2$ | $-R_1$ | $R_2$ | $R_3$ | $R_4$ |
|---|---|---|---|---|---|---|
| A.160 | O | O | 3-Br, 5-methyl-1-(2-methylphenyl)pyrazol-1-yl | H | H | $CH_2CH_3$ |
| A.161 | O | O | 3-Br, 5-methyl-1-(2-methylphenyl)pyrazol-1-yl | H | H | $CH(CH_3)_2$ |
| A.162 | O | O | 3-$F_3CH_2CO$, 5-methyl-1-(2-methylphenyl)pyrazol-1-yl | H | H | $CH_3$ |
| A.163 | O | O | 3-$F_3CH_2CO$, 5-methyl-1-(2-methylphenyl)pyrazol-1-yl | H | H | $CH_2CH_3$ |
| A.164 | O | O | 3-$F_3CH_2CO$, 5-methyl-1-(2-methylphenyl)pyrazol-1-yl | H | H | $CH(CH_3)_2$ |
| A.165 | O | O | 3-$F_3C$, 5-methyl-1-(2-chlorophenyl)pyrazol-1-yl | H | H | $CH_3$ |
| A.166 | O | O | 3-$F_3C$, 5-methyl-1-(2-chlorophenyl)pyrazol-1-yl | H | H | $CH_2CH_3$ |
| A.167 | O | O | 3-$F_3C$, 5-methyl-1-(2-chlorophenyl)pyrazol-1-yl | H | H | $CH(CH_3)_2$ |

TABLE A-continued $$(I)$$

Structure (I): A central carbon bearing R5, R6 connected to another carbon bearing R7, R8; the R5/R6 carbon bears a C(=Z2)N(R3)R4 group and the R7/R8 carbon bears N(R2) attached to C(=Z1)R1.

| Line | Z₁ | Z₂ | —R₁ | R₂ | R₃ | R₄ |
|---|---|---|---|---|---|---|
| A.168 | O | O | Cl-pyrazole(5-methyl, N-(2-chlorophenyl)) | H | H | CH₃ |
| A.169 | O | O | Cl-pyrazole(5-methyl, N-(2-chlorophenyl)) | H | H | CH₂CH₃ |
| A.170 | O | O | Cl-pyrazole(5-methyl, N-(2-chlorophenyl)) | H | H | CH(CH₃)₂ |
| A.171 | O | O | Br-pyrazole(5-methyl, N-(2-chlorophenyl)) | H | H | CH₃ |
| A.172 | O | O | Br-pyrazole(5-methyl, N-(2-chlorophenyl)) | H | H | CH₂CH₃ |
| A.173 | O | O | Br-pyrazole(5-methyl, N-(2-chlorophenyl)) | H | H | CH(CH₃)₂ |
| A.174 | O | O | F₃CH₂CO-pyrazole(5-methyl, N-(2-chlorophenyl)) | H | H | CH₃ |
| A.175 | O | O | F₃CH₂CO-pyrazole(5-methyl, N-(2-chlorophenyl)) | H | H | CH₂CH₃ |

TABLE A-continued $$(I)$$

| Line | $Z_1$ | $Z_2$ | —$R_1$ | $R_2$ | $R_3$ | $R_4$ |
|---|---|---|---|---|---|---|
| A.176 | O | O | F₃CH₂CO-[3-(trifluoroethoxy)-5-methyl-1-(2-chlorophenyl)pyrazol-1-yl] | H | H | CH(CH₃)₂ |
| A.177 | O | O | F₃C-[3-(trifluoromethyl)-5-methyl-1-(2-fluorophenyl)pyrazol-1-yl] | H | H | CH₃ |
| A.178 | O | O | F₃C-[3-(trifluoromethyl)-5-methyl-1-(2-fluorophenyl)pyrazol-1-yl] | H | H | CH₂CH₃ |
| A.179 | O | O | F₃C-[3-(trifluoromethyl)-5-methyl-1-(2-fluorophenyl)pyrazol-1-yl] | H | H | CH(CH₃)₂ |
| A.180 | O | O | Cl-[3-chloro-5-methyl-1-(2-fluorophenyl)pyrazol-1-yl] | H | H | CH₃ |
| A.181 | O | O | Cl-[3-chloro-5-methyl-1-(2-fluorophenyl)pyrazol-1-yl] | H | H | CH₂CH₃ |
| A.182 | O | O | Cl-[3-chloro-5-methyl-1-(2-fluorophenyl)pyrazol-1-yl] | H | H | CH(CH₃)₂ |
| A.183 | O | O | Br-[3-bromo-5-methyl-1-(2-fluorophenyl)pyrazol-1-yl] | H | H | CH₃ |

TABLE A-continued
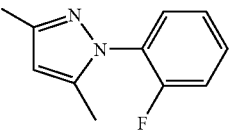
(I)
| Line | $Z_1$ | $Z_2$ | —$R_1$ | $R_2$ | $R_3$ | $R_4$ |
|---|---|---|---|---|---|---|
| A.184 | O | O | 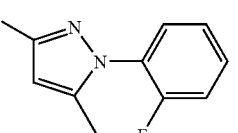 | H | H | $CH_2CH_3$ |
| A.185 | O | O | 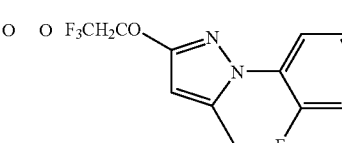 | H | H | $CH(CH_3)_2$ |
| A.186 | O | O | 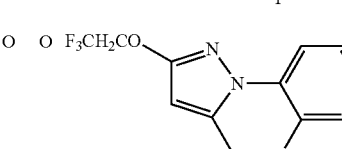 | H | H | $CH_3$ |
| A.187 | O | O | 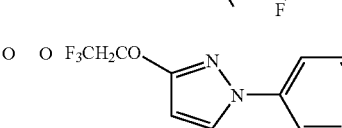 | H | H | $CH_2CH_3$ |
| A.188 | O | O | 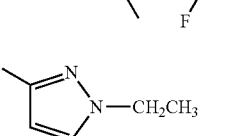 | H | H | $CH(CH_3)_2$ |
| A.189 | O | O | 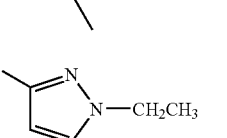 | H | H | $CH_3$ |
| A.190 | O | O | 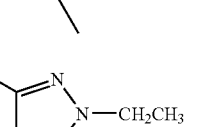 | H | H | $CH_2CH_3$ |
| A.191 | O | O | 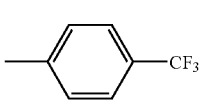 | H | H | $CH(CH_3)_2$ |
| A.192 | O | O |  | H | H | $CH_3$ |

TABLE A-continued (I)

| Line | $Z_1$ | $Z_2$ | —$R_1$ | $R_2$ | $R_3$ | $R_4$ |
|---|---|---|---|---|---|---|
| A.193 | O | O | 4-CF$_3$-C$_6$H$_4$— | H | H | CH$_2$CH$_3$ |
| A.194 | O | O | 4-CF$_3$-C$_6$H$_4$— | H | H | CH(CH$_3$)$_2$ |
| A.195 | O | O | 2-CH$_3$-4-CF$_3$-C$_6$H$_3$— | H | H | CH$_3$ |
| A.196 | O | O | 2-CH$_3$-4-CF$_3$-C$_6$H$_3$— | H | H | CH$_2$CH$_3$ |
| A.197 | O | O | 2-CH$_3$-4-CF$_3$-C$_6$H$_3$— | H | H | CH(CH$_3$)$_2$ |
| A.198 | O | O | 2-CH$_3$-6-CF$_3$-pyridin-3-yl | H | H | CH$_3$ |
| A.199 | O | O | 2-CH$_3$-6-CF$_3$-pyridin-3-yl | H | H | CH$_2$CH$_3$ |
| A.200 | O | O | 2-CH$_3$-6-CF$_3$-pyridin-3-yl | H | H | CH(CH$_3$)$_2$ |
| A.201 | O | O | 2-CH$_3$-C$_6$H$_4$— | H | H | CH$_3$ |
| A.202 | O | O | 2-CH$_3$-C$_6$H$_4$— | H | H | CH$_2$CH$_3$ |

TABLE A-continued (I) Structure: Z₁=R₁ attached via N(R₈)(R₂) to central C(R₇)(R₆)(R₅) bonded to C(=Z₂)N(R₄)(R₃)

| Line | Z₁ | Z₂ | —R₁ | R₂ | R₃ | R₄ |
|------|----|----|-----|----|----|-----|
| A.203 | O | O | 2-methylphenyl (o-tolyl, with H₃C at ortho position) | H | H | CH(CH₃)₂ |
| A.204 | O | O | 3-methyl-4-[CF(CF₃)₂]phenyl | H | H | CH₃ |
| A.205 | O | O | 3-methyl-4-[CF(CF₃)₂]phenyl | H | H | CH₂CH₃ |
| A.206 | O | O | 3-methyl-4-[CF(CF₃)₂]phenyl | H | H | CH(CH₃)₂ |
| A.207 | O | O | 3-(trifluoromethyl)-5-methyl-1-(3-chloropyridin-2-yl)-1H-pyrazol-4-yl | H | H | Cyclopropyl |
| A.208 | O | O | 3-chloro-5-methyl-1-(3-chloropyridin-2-yl)-1H-pyrazol-4-yl | H | H | Cyclopropyl |
| A.209 | O | O | 3-bromo-5-methyl-1-(3-chloropyridin-2-yl)-1H-pyrazol-4-yl | H | H | Cyclopropyl |
| A.210 | O | O | 3-(2,2,2-trifluoroethoxy)-5-methyl-1-(3-chloropyridin-2-yl)-1H-pyrazol-4-yl | H | H | Cyclopropyl |
| A.211 | O | O | 3-(trifluoromethyl)-5-methyl-1-(3-bromopyridin-2-yl)-1H-pyrazol-4-yl | H | H | Cyclopropyl |

TABLE A-continued (I)

| Line | $Z_1$ | $Z_2$ | —$R_1$ | $R_2$ | $R_3$ | $R_4$ |
|------|-------|-------|--------|-------|-------|-------|
| A.212 | O | O | 3-Cl, 5-Me pyrazole-1-yl linked to 3-Br pyridin-2-yl | H | H | Cyclopropyl |
| A.213 | O | O | 3-Br, 5-Me pyrazole-1-yl linked to 3-Br pyridin-2-yl | H | H | Cyclopropyl |
| A.214 | O | O | 3-(F$_3$CH$_2$CO), 5-Me pyrazole-1-yl linked to 3-Br pyridin-2-yl | H | H | Cyclopropyl |
| A.215 | S | S | 3-CF$_3$, 5-Me pyrazole-1-yl linked to 3-Cl pyridin-2-yl | H | H | Cyclopropyl |
| A.216 | S | S | 3-Cl, 5-Me pyrazole-1-yl linked to 3-Cl pyridin-2-yl | H | H | Cyclopropyl |
| A.217 | S | S | 3-Br, 5-Me pyrazole-1-yl linked to 3-Cl pyridin-2-yl | H | H | Cyclopropyl |
| A.218 | S | S | 3-(F$_3$CH$_2$CO), 5-Me pyrazole-1-yl linked to 3-Cl pyridin-2-yl | H | H | Cyclopropyl |
| A.219 | S | S | 3-CF$_3$, 5-Me pyrazole-1-yl linked to 3-Br pyridin-2-yl | H | H | Cyclopropyl |

TABLE A-continued (I)

| Line | $Z_1$ | $Z_2$ | —$R_1$ | $R_2$ | $R_3$ | $R_4$ |
|---|---|---|---|---|---|---|
| A.220 | S | S | 3-Cl, 5-Me-pyrazol-1-yl linked to 3-Br-pyridin-2-yl | H | H | Cyclopropyl |
| A.221 | S | S | 3-Br, 5-Me-pyrazol-1-yl linked to 3-Br-pyridin-2-yl | H | H | Cyclopropyl |
| A.222 | S | S | 3-(F$_3$CH$_2$CO), 5-Me-pyrazol-1-yl linked to 3-Br-pyridin-2-yl | H | H | Cyclopropyl |
| A.223 | O | S | 3-(F$_3$C), 5-Me-pyrazol-1-yl linked to 3-Cl-pyridin-2-yl | H | H | Cyclopropyl |
| A.224 | O | S | 3-Cl, 5-Me-pyrazol-1-yl linked to 3-Cl-pyridin-2-yl | H | H | Cyclopropyl |
| A.225 | O | S | 3-Br, 5-Me-pyrazol-1-yl linked to 3-Cl-pyridin-2-yl | H | H | Cyclopropyl |
| A.226 | O | S | 3-(F$_3$CH$_2$CO), 5-Me-pyrazol-1-yl linked to 3-Cl-pyridin-2-yl | H | H | Cyclopropyl |
| A.227 | O | S | 3-(F$_3$C), 5-Me-pyrazol-1-yl linked to 3-Br-pyridin-2-yl | H | H | Cyclopropyl |

TABLE A-continued (I)

| Line | Z₁ | Z₂ | —R₁ | R₂ | R₃ | R₄ |
|---|---|---|---|---|---|---|
| A.228 | O | S | Cl-pyrazole-pyridine (3-Cl pyrazole, 5-methyl; N-(3-Br-pyridin-2-yl)) | H | H | Cyclopropyl |
| A.229 | O | S | Br-pyrazole-pyridine (3-Br pyrazole, 5-methyl; N-(3-Br-pyridin-2-yl)) | H | H | Cyclopropyl |
| A.230 | O | S | F₃CH₂CO-pyrazole-pyridine (3-OCH₂CF₃ pyrazole, 5-methyl; N-(3-Br-pyridin-2-yl)) | H | H | Cyclopropyl |
| A.231 | S | O | F₃C-pyrazole-pyridine (3-CF₃ pyrazole, 5-methyl; N-(3-Cl-pyridin-2-yl)) | H | H | Cyclopropyl |
| A.232 | S | O | Cl-pyrazole-pyridine (3-Cl pyrazole, 5-methyl; N-(3-Cl-pyridin-2-yl)) | H | H | Cyclopropyl |
| A.233 | S | O | Br-pyrazole-pyridine (3-Br pyrazole, 5-methyl; N-(3-Cl-pyridin-2-yl)) | H | H | Cyclopropyl |
| A.234 | S | O | F₃CH₂CO-pyrazole-pyridine (3-OCH₂CF₃ pyrazole, 5-methyl; N-(3-Cl-pyridin-2-yl)) | H | H | Cyclopropyl |
| A.235 | S | O | F₃C-pyrazole-pyridine (3-CF₃ pyrazole, 5-methyl; N-(3-Br-pyridin-2-yl)) | H | H | Cyclopropyl |

TABLE A-continued

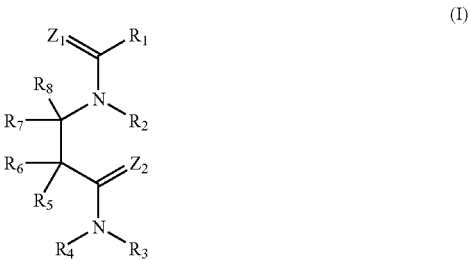

(I)

| Line | $Z_1$ | $Z_2$ | —$R_1$ | $R_2$ | $R_3$ | $R_4$ |
|---|---|---|---|---|---|---|
| A.236 | S | O | Cl-pyrazole-pyridine-Br, methyl | H | H | Cyclopropyl |
| A.237 | S | O | Br-pyrazole-pyridine-Br, methyl | H | H | Cyclopropyl |
| A.238 | S | O | F$_3$CH$_2$CO-pyrazole-pyridine-Br, methyl | H | H | Cyclopropyl |
| A.239 | O | O | F$_3$C-pyrazole-pyridine-Cl, methyl | CH$_3$ | H | Cyclopropyl |
| A.240 | O | O | Cl-pyrazole-pyridine-Cl, methyl | CH$_3$ | H | Cyclopropyl |
| A.241 | O | O | Br-pyrazole-pyridine-Cl, methyl | CH$_3$ | H | Cyclopropyl |
| A.242 | O | O | F$_3$CH$_2$CO-pyrazole-pyridine-Cl, methyl | CH$_3$ | H | Cyclopropyl |
| A.243 | O | O | F$_3$C-pyrazole-pyridine-Br, methyl | CH$_3$ | H | Cyclopropyl |

TABLE A-continued (I)

| Line | $Z_1$ | $Z_2$ | —$R_1$ | $R_2$ | $R_3$ | $R_4$ |
|---|---|---|---|---|---|---|
| A.244 | O | O | Cl-pyrazole(CH3)-N-pyridine-Br | CH$_3$ | H | Cyclopropyl |
| A.245 | O | O | Br-pyrazole(CH3)-N-pyridine-Br | CH$_3$ | H | Cyclopropyl |
| A.246 | O | O | F$_3$CH$_2$CO-pyrazole(CH3)-N-pyridine-Br | CH$_3$ | H | Cyclopropyl |
| A.247 | O | O | F$_3$C-pyrazole(CH3)-N-pyridine-Cl | H | CH$_3$ | Cyclopropyl |
| A.248 | O | O | Cl-pyrazole(CH3)-N-pyridine-Cl | H | CH$_3$ | Cyclopropyl |
| A.249 | O | O | Br-pyrazole(CH3)-N-pyridine-Cl | H | CH$_3$ | Cyclopropyl |
| A.250 | O | O | F$_3$CH$_2$CO-pyrazole(CH3)-N-pyridine-Cl | H | CH$_3$ | Cyclopropyl |
| A.251 | O | O | F$_3$C-pyrazole(CH3)-N-pyridine-Br | H | CH$_3$ | Cyclopropyl |

TABLE A-continued

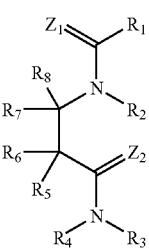

| Line | $Z_1$ | $Z_2$ | —$R_1$ | $R_2$ | $R_3$ | $R_4$ |
|---|---|---|---|---|---|---|
| A.252 | O | O | 3-Cl, 5-methyl-1-(3-bromopyridin-2-yl)pyrazol-4-yl | H | $CH_3$ | Cyclopropyl |
| A.253 | O | O | 3-Br, 5-methyl-1-(3-bromopyridin-2-yl)pyrazol-4-yl | H | $CH_3$ | Cyclopropyl |
| A.254 | O | O | 3-$F_3CH_2CO$, 5-methyl-1-(3-bromopyridin-2-yl)pyrazol-4-yl | H | $CH_3$ | Cyclopropyl |
| A.255 | O | O | 3-$F_3C$, 5-methyl-1-(2-methylphenyl)pyrazol-4-yl | H | H | Cyclopropyl |
| A.256 | O | O | 3-Cl, 5-methyl-1-(2-methylphenyl)pyrazol-4-yl | H | H | Cyclopropyl |
| A.257 | O | O | 3-Br, 5-methyl-1-(2-methylphenyl)pyrazol-4-yl | H | H | Cyclopropyl |
| A.258 | O | O | 3-$F_3CH_2CO$, 5-methyl-1-(2-methylphenyl)pyrazol-4-yl | H | H | Cyclopropyl |
| A.259 | O | O | 3-$F_3C$, 5-methyl-1-(2-chlorophenyl)pyrazol-4-yl | H | H | Cyclopropyl |

TABLE A-continued $$(I)$$

| Line | $Z_1$ | $Z_2$ | —$R_1$ | $R_2$ | $R_3$ | $R_4$ |
|---|---|---|---|---|---|---|
| A.260 | O | O | 3-Cl, 5-methyl-1-(2-chlorophenyl)pyrazol-4-yl | H | H | Cyclopropyl |
| A.261 | O | O | 3-Br, 5-methyl-1-(2-chlorophenyl)pyrazol-4-yl | H | H | Cyclopropyl |
| A.262 | O | O | 3-F$_3$CH$_2$CO, 5-methyl-1-(2-chlorophenyl)pyrazol-4-yl | H | H | Cyclopropyl |
| A.263 | O | O | 3-F$_3$C, 5-methyl-1-(2-fluorophenyl)pyrazol-4-yl | H | H | Cyclopropyl |
| A.264 | O | O | 3-Cl, 5-methyl-1-(2-fluorophenyl)pyrazol-4-yl | H | H | Cyclopropyl |
| A.265 | O | O | 3-Br, 5-methyl-1-(2-fluorophenyl)pyrazol-4-yl | H | H | Cyclopropyl |
| A.266 | O | O | 3-F$_3$CH$_2$CO, 5-methyl-1-(2-fluorophenyl)pyrazol-4-yl | H | H | Cyclopropyl |
| A.267 | O | O | 3-F$_3$C, 5-methyl-1-ethylpyrazol-4-yl | H | H | Cyclopropyl |
| A.268 | O | O | 4-(CF$_3$)phenyl | H | H | Cyclopropyl |

TABLE A-continued

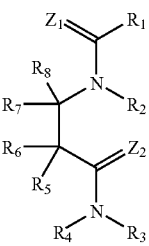

| Line | $Z_1$ | $Z_2$ | —$R_1$ | $R_2$ | $R_3$ | $R_4$ |
|---|---|---|---|---|---|---|
| A.269 | O | O | 2,5-(CH3,CF3)-phenyl | H | H | Cyclopropyl |
| A.270 | O | O | 2-CH3-6-CF3-pyridin-3-yl (3-Me) | H | H | Cyclopropyl |
| A.271 | O | O | 2-CH3-phenyl | H | H | Cyclopropyl |
| A.272 | O | O | 3-CH3-4-CF(CF3)2-phenyl | H | H | Cyclopropyl |
| A.273 | O | O | 3-CF3-1-(3-Cl-pyridin-2-yl)-5-methyl-pyrazole | H | H | C(CH3)2CH2SCH3 |
| A.274 | O | O | 3-Cl-1-(3-Cl-pyridin-2-yl)-5-methyl-pyrazole | H | H | C(CH3)2CH2SCH3 |
| A.275 | O | O | 3-Br-1-(3-Cl-pyridin-2-yl)-5-methyl-pyrazole | H | H | C(CH3)2CH2SCH3 |
| A.276 | O | O | 3-OCH2CF3-1-(3-Cl-pyridin-2-yl)-5-methyl-pyrazole | H | H | C(CH3)2CH2SCH3 |

TABLE A-continued (I)

| Line | $Z_1$ | $Z_2$ | —$R_1$ | $R_2$ | $R_3$ | $R_4$ |
|---|---|---|---|---|---|---|
| A.277 | O | O | F₃C-pyrazole-pyridine-Br (5-methyl) | H | H | C(CH₃)₂CH₂SCH₃ |
| A.278 | O | O | Cl-pyrazole-pyridine-Br (5-methyl) | H | H | C(CH₃)₂CH₂SCH₃ |
| A.279 | O | O | Br-pyrazole-pyridine-Br (5-methyl) | H | H | C(CH₃)₂CH₂SCH₃ |
| A.280 | O | O | F₃CH₂CO-pyrazole-pyridine-Br (5-methyl) | H | H | C(CH₃)₂CH₂SCH₃ |
| A.281 | S | S | F₃C-pyrazole-pyridine-Cl (5-methyl) | H | H | C(CH₃)₂CH₂SCH₃ |
| A.282 | S | S | Cl-pyrazole-pyridine-Cl (5-methyl) | H | H | C(CH₃)₂CH₂SCH₃ |
| A.283 | S | S | Br-pyrazole-pyridine-Cl (5-methyl) | H | H | C(CH₃)₂CH₂SCH₃ |
| A.284 | S | S | F₃CH₂CO-pyrazole-pyridine-Cl (5-methyl) | H | H | C(CH₃)₂CH₂SCH₃ |

TABLE A-continued (I)

[Structure of formula (I): central backbone with Z₁=C(R₁)–N(R₈)(R₂) on one side and Z₂=C– N(R₄)(R₃) on the other, with R₇, R₆, R₅ substituents]

| Line | Z₁ | Z₂ | —R₁ | R₂ | R₃ | R₄ |
|---|---|---|---|---|---|---|
| A.285 | S | S | 3-(CF₃)-5-methyl-1-(3-bromopyridin-2-yl)pyrazol-1-yl | H | H | C(CH₃)₂CH₂SCH₃ |
| A.286 | S | S | 3-Cl-5-methyl-1-(3-bromopyridin-2-yl)pyrazol-1-yl | H | H | C(CH₃)₂CH₂SCH₃ |
| A.287 | S | S | 3-Br-5-methyl-1-(3-bromopyridin-2-yl)pyrazol-1-yl | H | H | C(CH₃)₂CH₂SCH₃ |
| A.288 | S | S | 3-(F₃CH₂CO)-5-methyl-1-(3-bromopyridin-2-yl)pyrazol-1-yl | H | H | C(CH₃)₂CH₂SCH₃ |
| A.289 | O | S | 3-(CF₃)-5-methyl-1-(3-chloropyridin-2-yl)pyrazol-1-yl | H | H | C(CH₃)₂CH₂SCH₃ |
| A.290 | O | S | 3-Cl-5-methyl-1-(3-chloropyridin-2-yl)pyrazol-1-yl | H | H | C(CH₃)₂CH₂SCH₃ |
| A.291 | O | S | 3-Br-5-methyl-1-(3-chloropyridin-2-yl)pyrazol-1-yl | H | H | C(CH₃)₂CH₂SCH₃ |
| A.292 | O | S | 3-(F₃CH₂CO)-5-methyl-1-(3-chloropyridin-2-yl)pyrazol-1-yl | H | H | C(CH₃)₂CH₂SCH₃ |

TABLE A-continued (I)

| Line | $Z_1$ | $Z_2$ | —$R_1$ | $R_2$ | $R_3$ | $R_4$ |
|---|---|---|---|---|---|---|
| A.293 | O | S | 3-(CF$_3$)-5-methyl-1-(3-bromopyridin-2-yl)pyrazol-1-yl | H | H | C(CH$_3$)$_2$CH$_2$SCH$_3$ |
| A.294 | O | S | 3-Cl-5-methyl-1-(3-bromopyridin-2-yl)pyrazol-1-yl | H | H | C(CH$_3$)$_2$CH$_2$SCH$_3$ |
| A.295 | O | S | 3-Br-5-methyl-1-(3-bromopyridin-2-yl)pyrazol-1-yl | H | H | C(CH$_3$)$_2$CH$_2$SCH$_3$ |
| A.296 | O | S | 3-(F$_3$CH$_2$CO)-5-methyl-1-(3-bromopyridin-2-yl)pyrazol-1-yl | H | H | C(CH$_3$)$_2$CH$_2$SCH$_3$ |
| A.297 | S | O | 3-(CF$_3$)-5-methyl-1-(3-chloropyridin-2-yl)pyrazol-1-yl | H | H | C(CH$_3$)$_2$CH$_2$SCH$_3$ |
| A.298 | S | O | 3-Cl-5-methyl-1-(3-chloropyridin-2-yl)pyrazol-1-yl | H | H | C(CH$_3$)$_2$CH$_2$SCH$_3$ |
| A.299 | S | O | 3-Br-5-methyl-1-(3-chloropyridin-2-yl)pyrazol-1-yl | H | H | C(CH$_3$)$_2$CH$_2$SCH$_3$ |
| A.300 | S | O | 3-(F$_3$CH$_2$CO)-5-methyl-1-(3-chloropyridin-2-yl)pyrazol-1-yl | H | H | C(CH$_3$)$_2$CH$_2$SCH$_3$ |

TABLE A-continued

(I)

| Line | $Z_1$ | $Z_2$ | —$R_1$ | $R_2$ | $R_3$ | $R_4$ |
|---|---|---|---|---|---|---|
| A.301 | S | O | F$_3$C-[3-(trifluoromethyl)-5-methyl-pyrazol-1-yl]-(3-bromopyridin-2-yl) | H | H | C(CH$_3$)$_2$CH$_2$SCH$_3$ |
| A.302 | S | O | Cl-[3-chloro-5-methyl-pyrazol-1-yl]-(3-bromopyridin-2-yl) | H | H | C(CH$_3$)$_2$CH$_2$SCH$_3$ |
| A.303 | S | O | Br-[3-bromo-5-methyl-pyrazol-1-yl]-(3-bromopyridin-2-yl) | H | H | C(CH$_3$)$_2$CH$_2$SCH$_3$ |
| A.304 | S | O | F$_3$CH$_2$CO-[3-(2,2,2-trifluoroethoxy)-5-methyl-pyrazol-1-yl]-(3-bromopyridin-2-yl) | H | H | C(CH$_3$)$_2$CH$_2$SCH$_3$ |
| A.305 | O | O | F$_3$C-[3-(trifluoromethyl)-5-methyl-pyrazol-1-yl]-(3-chloropyridin-2-yl) | CH$_3$ | H | C(CH$_3$)$_2$CH$_2$SCH$_3$ |
| A.306 | O | O | Cl-[3-chloro-5-methyl-pyrazol-1-yl]-(3-chloropyridin-2-yl) | CH$_3$ | H | C(CH$_3$)$_2$CH$_2$SCH$_3$ |
| A.307 | O | O | Br-[3-bromo-5-methyl-pyrazol-1-yl]-(3-chloropyridin-2-yl) | CH$_3$ | H | C(CH$_3$)$_2$CH$_2$SCH$_3$ |
| A.308 | O | O | F$_3$CH$_2$CO-[3-(2,2,2-trifluoroethoxy)-5-methyl-pyrazol-1-yl]-(3-chloropyridin-2-yl) | CH$_3$ | H | C(CH$_3$)$_2$CH$_2$SCH$_3$ |

TABLE A-continued (I)

| Line | $Z_1$ | $Z_2$ | —$R_1$ | $R_2$ | $R_3$ | $R_4$ |
|---|---|---|---|---|---|---|
| A.309 | O | O | F₃C-pyrazole(5-Me)-N-pyridine(3-Br) | CH₃ | H | C(CH₃)₂CH₂SCH₃ |
| A.310 | O | O | Cl-pyrazole(5-Me)-N-pyridine(3-Br) | CH₃ | H | C(CH₃)₂CH₂SCH₃ |
| A.311 | O | O | Br-pyrazole(5-Me)-N-pyridine(3-Br) | CH₃ | H | C(CH₃)₂CH₂SCH₃ |
| A.312 | O | O | F₃CH₂CO-pyrazole(5-Me)-N-pyridine(3-Br) | CH₃ | H | C(CH₃)₂CH₂SCH₃ |
| A.313 | O | O | F₃C-pyrazole(5-Me)-N-pyridine(3-Cl) | H | CH₃ | C(CH₃)₂CH₂SCH₃ |
| A.314 | O | O | Cl-pyrazole(5-Me)-N-pyridine(3-Cl) | H | CH₃ | C(CH₃)₂CH₂SCH₃ |
| A.315 | O | O | Br-pyrazole(5-Me)-N-pyridine(3-Cl) | H | CH₃ | C(CH₃)₂CH₂SCH₃ |
| A.316 | O | O | F₃CH₂CO-pyrazole(5-Me)-N-pyridine(3-Cl) | H | CH₃ | C(CH₃)₂CH₂SCH₃ |

TABLE A-continued (I)

[Structure of formula (I): Z₁=C(R₁)-N(R₈)(R₂) backbone with R₇,R₆,R₅ substituents and C(=Z₂)-N(R₄)(R₃)]

| Line | Z₁ | Z₂ | —R₁ | R₂ | R₃ | R₄ |
|------|----|----|-----|----|----|----|
| A.317 | O | O | 3-(CF₃)-5-methyl-1-(3-bromopyridin-2-yl)pyrazol-1-yl | H | CH₃ | C(CH₃)₂CH₂SCH₃ |
| A.318 | O | O | 3-Cl-5-methyl-1-(3-bromopyridin-2-yl)pyrazol-1-yl | H | CH₃ | C(CH₃)₂CH₂SCH₃ |
| A.319 | O | O | 3-Br-5-methyl-1-(3-bromopyridin-2-yl)pyrazol-1-yl | H | CH₃ | C(CH₃)₂CH₂SCH₃ |
| A.320 | O | O | 3-(F₃CH₂CO)-5-methyl-1-(3-bromopyridin-2-yl)pyrazol-1-yl | H | CH₃ | C(CH₃)₂CH₂SCH₃ |
| A.321 | O | O | 3-(CF₃)-5-methyl-1-(2-methylphenyl)pyrazol-1-yl | H | H | C(CH₃)₂CH₂SCH₃ |
| A.322 | O | O | 3-Cl-5-methyl-1-(2-methylphenyl)pyrazol-1-yl | H | H | C(CH₃)₂CH₂SCH₃ |
| A.323 | O | O | 3-Br-5-methyl-1-(2-methylphenyl)pyrazol-1-yl | H | H | C(CH₃)₂CH₂SCH₃ |
| A.324 | O | O | 3-(F₃CH₂CO)-5-methyl-1-(2-methylphenyl)pyrazol-1-yl | H | H | C(CH₃)₂CH₂SCH₃ |

TABLE A-continued
(I)
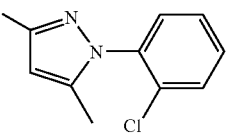
| Line | $Z_1$ | $Z_2$ | —$R_1$ | $R_2$ | $R_3$ | $R_4$ |
|------|-------|-------|--------|-------|-------|-------|
| A.325 | O | O | 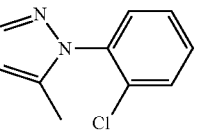 | H | H | $C(CH_3)_2CH_2SCH_3$ |
| A.326 | O | O | 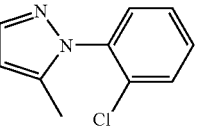 | H | H | $C(CH_3)_2CH_2SCH_3$ |
| A.327 | O | O | 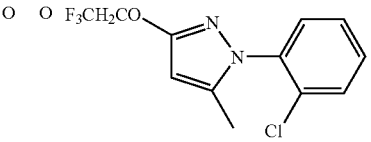 | H | H | $C(CH_3)_2CH_2SCH_3$ |
| A.328 | O | O | 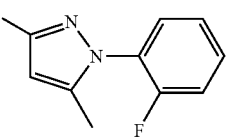 | H | H | $C(CH_3)_2CH_2SCH_3$ |
| A.329 | O | O | 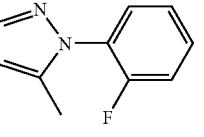 | H | H | $C(CH_3)_2CH_2SCH_3$ |
| A.330 | O | O | Cl | H | H | $C(CH_3)_2CH_2SCH_3$ |

TABLE A-continued

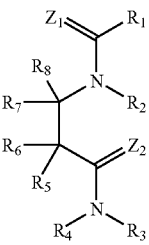
(I)

| Line | $Z_1$ | $Z_2$ | —$R_1$ | $R_2$ | $R_3$ | $R_4$ |
|---|---|---|---|---|---|---|
| A.331 | O | O | 3-Br-5-methyl-1-(2-fluorophenyl)pyrazol-yl | H | H | $C(CH_3)_2CH_2SCH_3$ |
| A.332 | O | O | 3-($F_3CH_2CO$)-5-methyl-1-(2-fluorophenyl)pyrazol-yl | H | H | $C(CH_3)_2CH_2SCH_3$ |
| A.333 | O | O | 3-$CF_3$-5-methyl-1-ethylpyrazol-yl | H | H | $C(CH_3)_2CH_2SCH_3$ |
| A.334 | O | O | 4-$CF_3$-phenyl | H | H | $C(CH_3)_2CH_2SCH_3$ |
| A.335 | O | O | 4-$CF_3$-2-$CH_3$-phenyl | H | H | $C(CH_3)_2CH_2SCH_3$ |
| A.336 | O | O | 6-$CF_3$-2,3-dimethylpyridin-yl | H | H | $C(CH_3)_2CH_2SCH_3$ |
| A.337 | O | O | 2-methylphenyl | H | H | $C(CH_3)_2CH_2SCH_3$ |
| A.338 | O | O | 4-$CF(CF_3)_2$-2-$CH_3$-phenyl | H | H | $C(CH_3)_2CH_2SCH_3$ |

TABLE 1

This table discloses the 338 compounds T1.1 to T1.338 of the formula

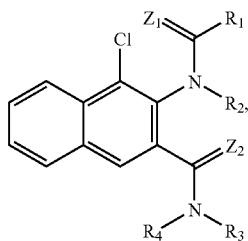

(T1)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

For example, the specific compound T1.23 is the compound of the formula T1, in which each of the variables $Z_1$, $Z_2$, $R_1$, $R_2$, $R_3$ and $R_4$ has the specific meaning given in the line A.23 of the Table A. According to the same system, also all of the other 337 specific compounds disclosed in the Table 1 as well as all of the specific compounds disclosed in the Tables 2 to 85 are specified analogously.

TABLE 2

This table discloses the 338 compounds T2.1 to T2.338 of the formula

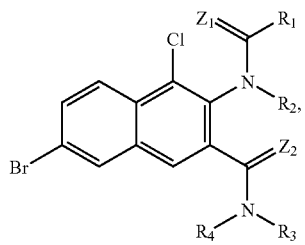

(T2)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 3

This table discloses the 338 compounds T3.1 to T3.338 of the formula

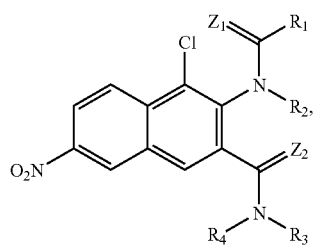

(T3)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 4

This table discloses the 338 compounds T4.1 to T4.338 of the formula

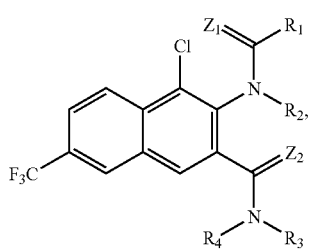

(T4)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 5

This table discloses the 338 compounds T5.1 to T5.338 of the formula

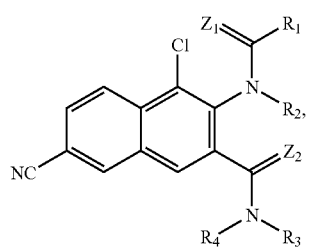

(T5)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 6

This table discloses the 338 compounds T6.1 to T6.338 of the formula

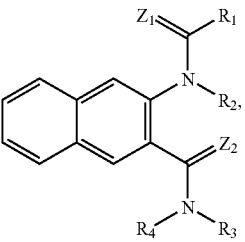

(T6)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 7

This table discloses the 338 compounds T7.1 to T7.338 of the formula (T7)

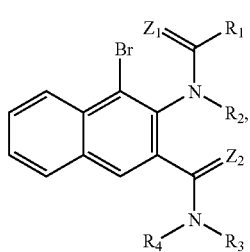

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 8

This table discloses the 338 compounds T8.1 to T8.338 of the formula (T8)

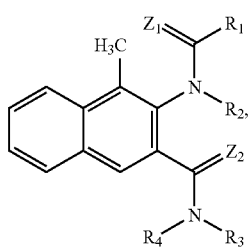

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 9

This table discloses the 338 compounds T9.1 to T9.338 of the formula (T9)

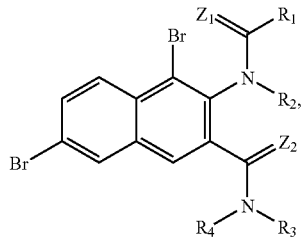

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 10

This table discloses the 338 compounds T10.1 to T10.338 of the formula (T10)

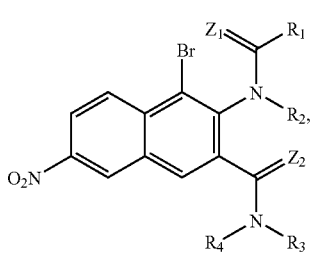

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 11

This table discloses the 338 compounds T11.1 to T11.338 of the formula (T11)

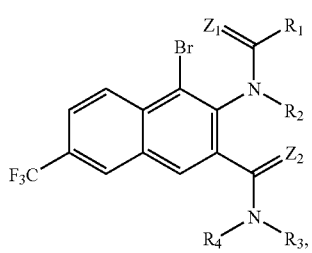

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 12

This table discloses the 338 compounds T12.1 to T12.338 of the formula (T12)

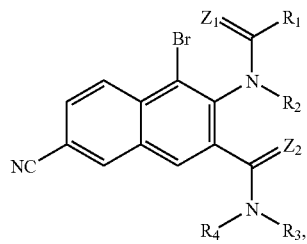

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 13

This table discloses the 338 compounds T13.1 to T13.338 of the formula

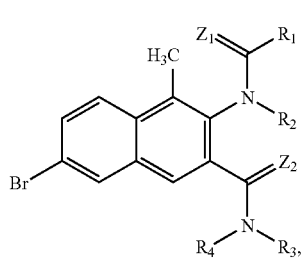
(T13)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 14

This table discloses the 338 compounds T14.1 to T14.338 of the formula

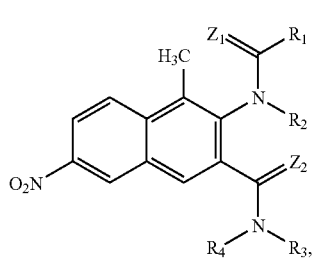
(T14)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 15

This table discloses the 338 compounds T15.1 to T15.338 of the formula

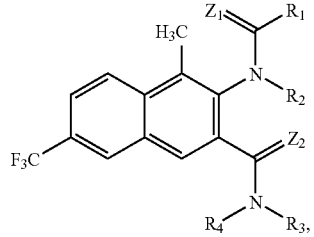
(T15)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 16

This table discloses the 338 compounds T16.1 to T16.338 of the formula

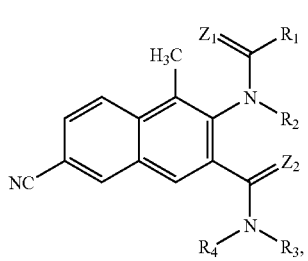
(T16)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 17

This table discloses the 338 compounds T17.1 to T17.338 of the formula

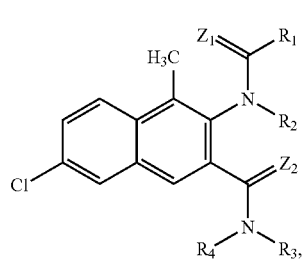
(T17)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 18

This table discloses the 338 compounds T18.1 to T18.338 of the formula

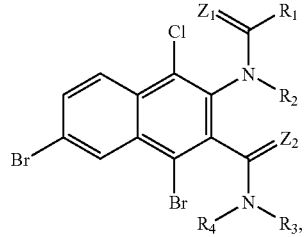
(T18)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 19

This table discloses the 338 compounds T19.1 to T19.338 of the formula

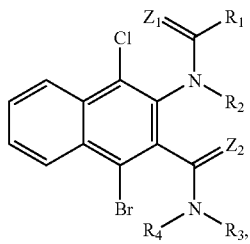

(T19)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 20

This table discloses the 338 compounds T20.1 to T20.338 of the formula

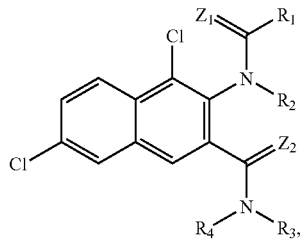

(T20)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 21

This table discloses the 338 compounds T21.1 to T21.338 of the formula

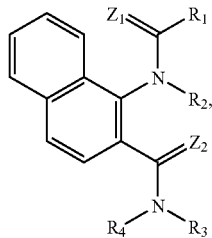

(T21)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 22

This table discloses the 338 compounds T22.1 to T22.338 of the formula

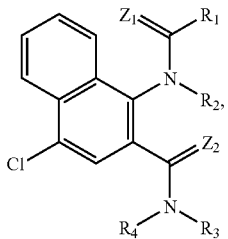

(T22)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 23

This table discloses the 338 compounds T23.1 to T23.338 of the formula (T23)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 24

This table discloses the 338 compounds T24.1 to T24.338 of the formula

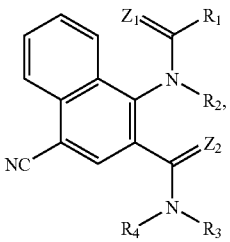

(T24)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 25

This table discloses the 338 compounds T25.1 to T25.338 of the formula

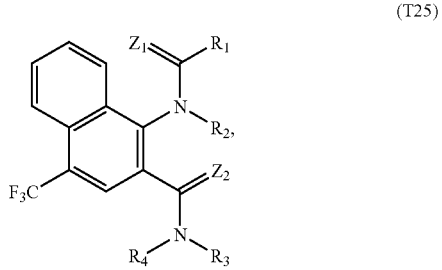

(T25)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 26

This table discloses the 338 compounds T26.1 to T26.338 of the formula

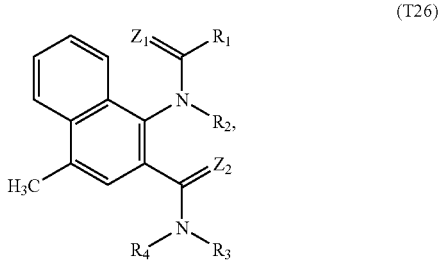

(T26)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 27

This table discloses the 338 compounds T27.1 to T27.338 of the formula

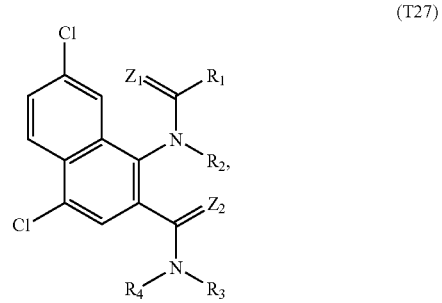

(T27)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 28

This table discloses the 338 compounds T28.1 to T28.338 of the formula

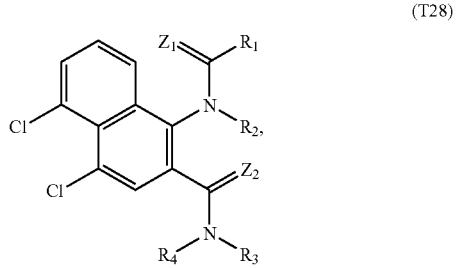

(T28)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 29

This table discloses the 338 compounds T29.1 to T29.338 of the formula

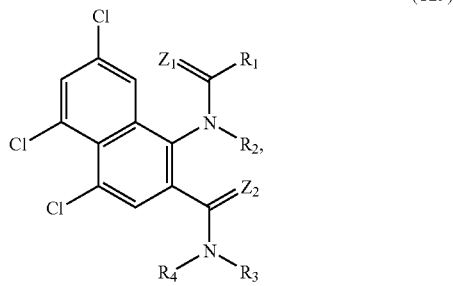

(T29)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 30

This table discloses the 338 compounds T30.1 to T30.338 of the formula

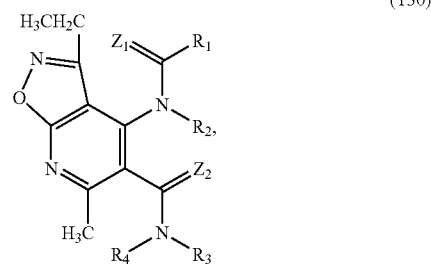

(T30)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 31

This table discloses the 338 compounds T31.1 to T31.338 of the formula

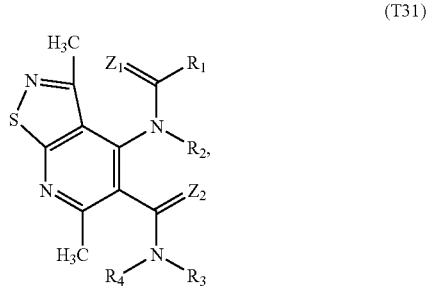
(T31)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 32

This table discloses the 338 compounds T32.1 to T32.338 of the formula

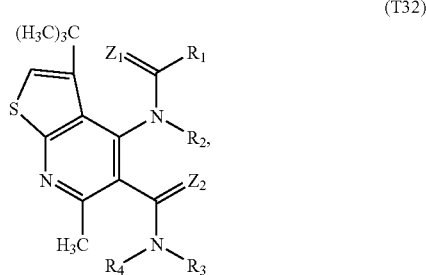
(T32)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 33

This table discloses the 338 compounds T33.1 to T33.338 of the formula

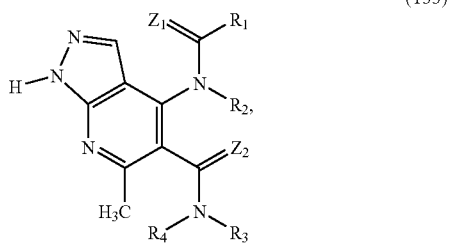
(T33)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 34

This table discloses the 338 compounds T34.1 to T34.338 of the formula

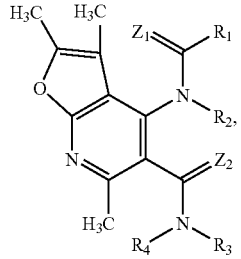
(T34)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 35

This table discloses the 338 compounds T35.1 to T35.338 of the formula

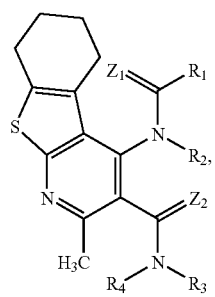
(T35)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 36

This table discloses the 338 compounds T36.1 to T36.338 of the formula

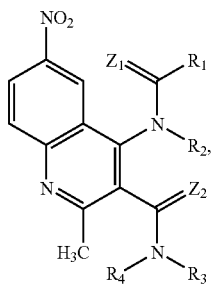
(T36)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 37

This table discloses the 338 compounds T37.1 to T37.338 of the formula

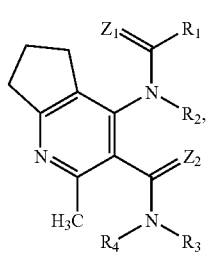
(T37)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 38

This table discloses the 338 compounds T38.1 to T38.338 of the formula

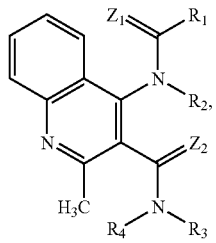
(T38)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 39

This table discloses the 338 compounds T39.1 to T39.338 of the formula

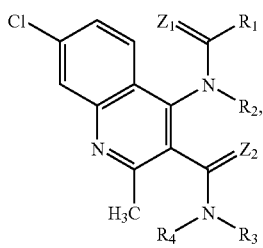
(T39)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 40

This table discloses the 338 compounds T40.1 to T40.338 of the formula

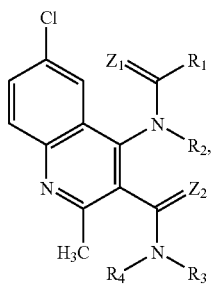
(T40)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 41

This table discloses the 338 compounds T41.1 to T41.338 of the formula

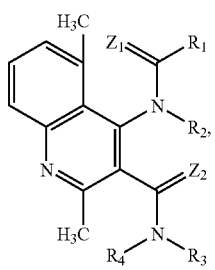
(T41)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 42

This table discloses the 338 compounds T42.1 to T42.338 of the formula

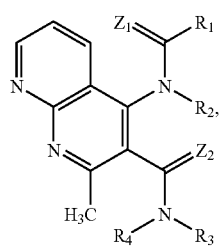
(T42)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 43

This table discloses the 338 compounds T43.1 to T43.338 of the formula

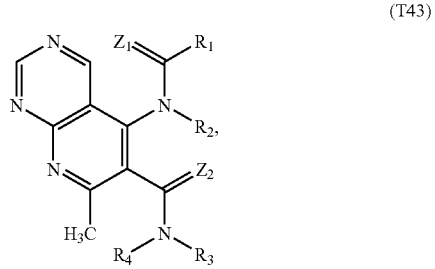

(T43)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 44

This table discloses the 338 compounds T44.1 to T44.338 of the formula

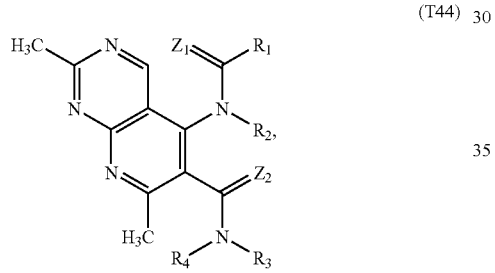

(T44)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 45

This table discloses the 338 compounds T45.1 to T45.338 of the formula

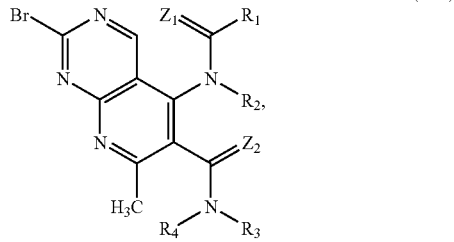

(T45)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 46

This table discloses the 338 compounds T46.1 to T46.338 of the formula

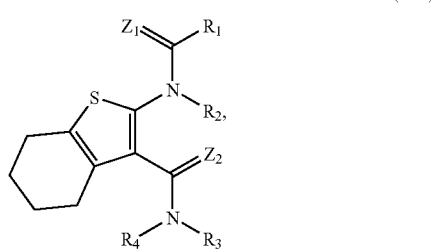

(T46)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 47

This table discloses the 338 compounds T47.1 to T47.338 of the formula

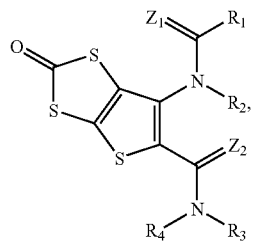

(T47)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 48

This table discloses the 338 compounds T48.1 to T48.338 of the formula

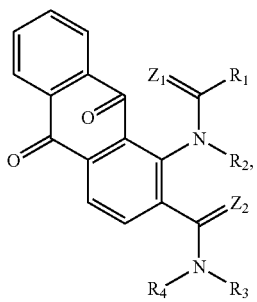

(T48)

in which, for each of these 338 specific compounds, each of the variables $Z_1, Z_2, R_1, R_2, R_3$ and $R_4$ has the specific meaning given in the corresponding line, appropriately selected from the 338 lines A.1 to A.338, of the Table A.

TABLE 49

This table discloses the 338 compounds T49.1 to T49.338 of the formula

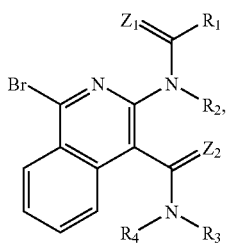

(T49)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 50

This table discloses the 338 compounds T50.1 to T50.338 of the formula

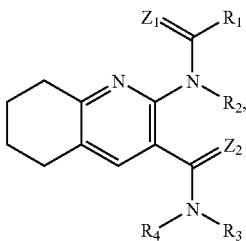

(T50)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 51

This table discloses the 338 compounds T51.1 to T51.338 of the formula

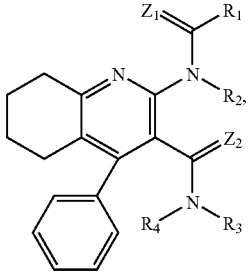

(T51)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 52

This table discloses the 338 compounds T52.1 to T52.338 of the formula

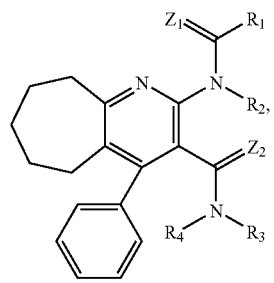

(T52)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 53

This table discloses the 338 compounds T53.1 to T53.338 of the formula

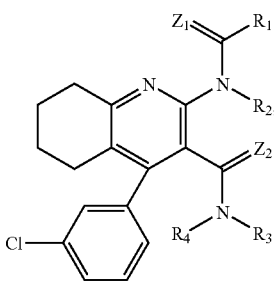

(T53)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 54

This table discloses the 338 compounds T54.1 to T54.338 of the formula

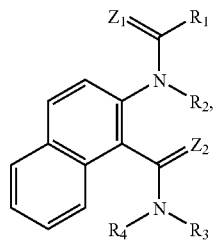

(T54)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 55

This table discloses the 338 compounds T55.1 to T55.338 of the formula

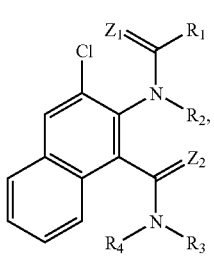
(T55)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 56

This table discloses the 338 compounds T56.1 to T56.338 of the formula

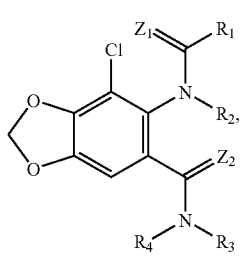
(T56)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 57

This table discloses the 338 compounds T57.1 to T57.338 of the formula

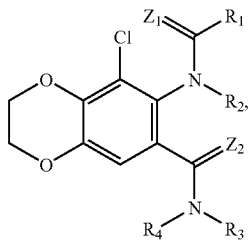
(T57)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 58

This table discloses the 338 compounds T58.1 to T58.338 of the formula

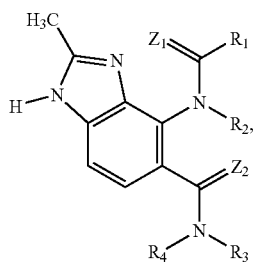
(T58)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 59

This table discloses the 338 compounds T59.1 to T59.338 of the formula

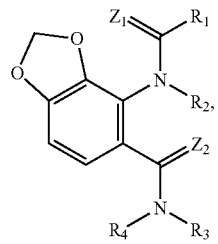
(T59)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 60

This table discloses the 338 compounds T60.1 to T60.338 of the formula

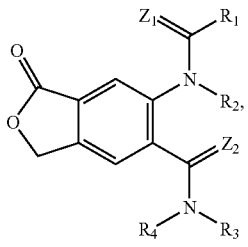
(T60)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 61

This table discloses the 338 compounds T61.1 to T61.338 of the formula

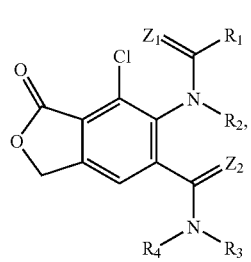

(T61)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 62

This table discloses the 338 compounds T62.1 to T62.338 of the formula

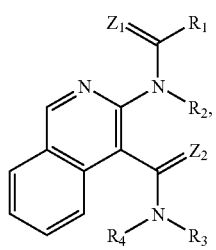

(T62)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 63

This table discloses the 338 compounds T63.1 to T63.338 of the formula

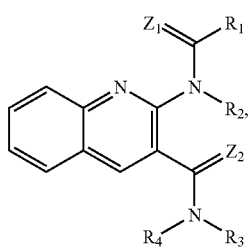

(T63)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 64

This table discloses the 338 compounds T64.1 to T64.338 of the formula

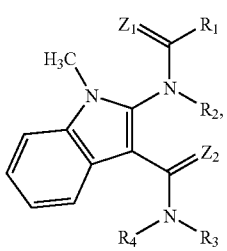

(T64)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 65

This table discloses the 338 compounds T65.1 to T65.338 of the formula

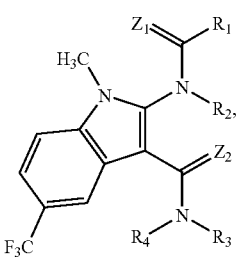

(T65)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 66

This table discloses the 338 compounds T66.1 to T66.338 of the formula

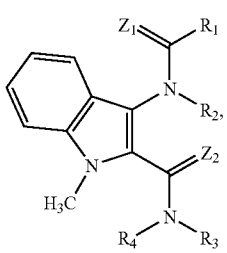

(T66)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 67

This table discloses the 338 compounds T67.1 to T67.338 of the formula

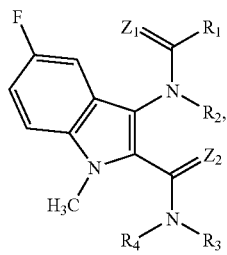
(T67)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 68

This table discloses the 338 compounds T68.1 to T68.338 of the formula

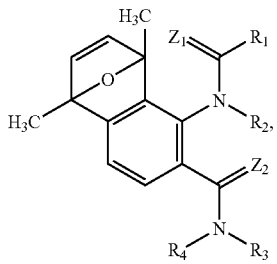
(T68)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 69

This table discloses the 338 compounds T69.1 to T69.338 of the formula

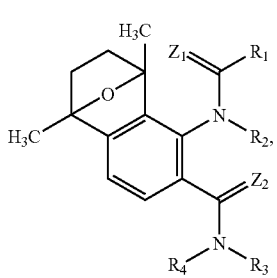
(T69)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 70

This table discloses the 338 compounds T70.1 to T70.338 of the formula

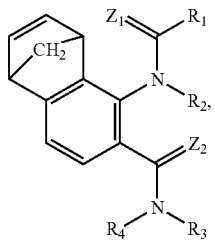
(T70)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 71

This table discloses the 338 compounds T71.1 to T71.338 of the formula

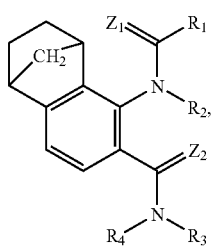
(T71)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 72

This table discloses the 338 compounds T72.1 to T72.338 of the formula

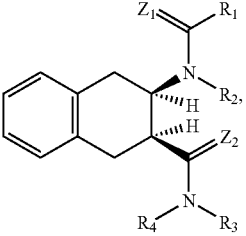
(T72)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 73

This table discloses the 338 compounds T73.1 to T73.338 of the formula

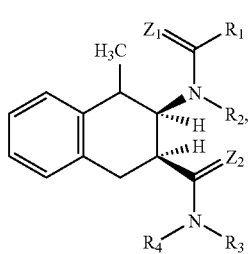

(T73)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 74

This table discloses the 338 compounds T74.1 to T74.338 of the formula

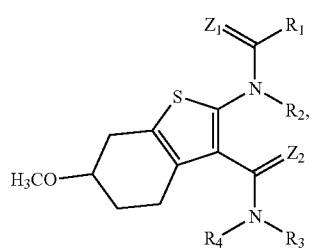

(T74)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 75

This table discloses the 338 compounds T75.1 to T75.338 of the formula

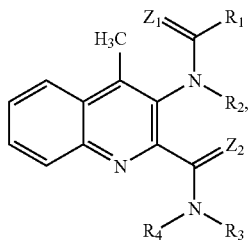

(T75)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 76

This table discloses the 338 compounds T76.1 to T76.338 of the formula

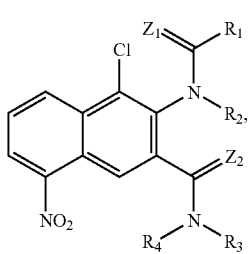

(T76)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 77

This table discloses the 338 compounds T77.1 to T77.338 of the formula

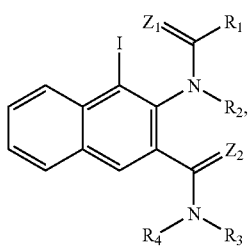

(T77)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 78

This table discloses the 338 compounds T78.1 to T78.338 of the formula

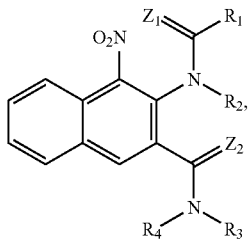

(T78)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 79

This table discloses the 338 compounds T79.1 to T79.338 of the formula

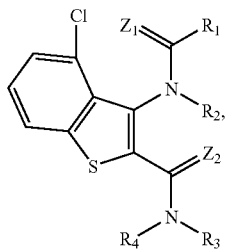
(T79)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 80

This table discloses the 338 compounds T80.1 to T80.338 of the formula

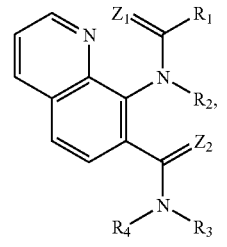
(T80)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 81

This table discloses the 338 compounds T81.1 to T81.338 of the formula

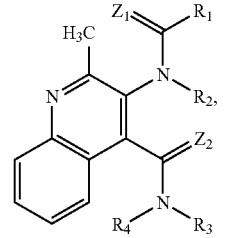
(T81)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 82

This table discloses the 338 compounds T82.1 to T82.338 of the formula

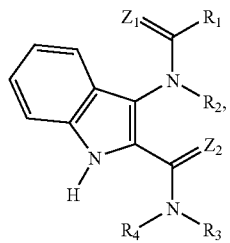
(T82)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 83

This table discloses the 338 compounds T83.1 to T83.338 of the formula

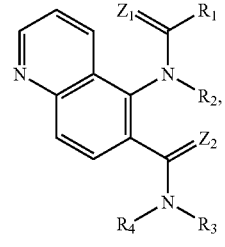
(T83)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 84

This table discloses the 338 compounds T84.1 to T84.338 of the formula

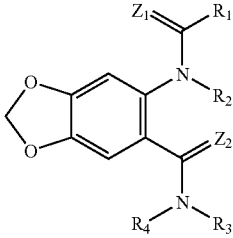
(T84)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 85

This table discloses the 338 compounds T85.1 to T85.338 of the formula

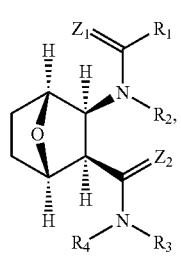
(T85)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 86

This table discloses the 338 compounds T86.1 to T86.338 of the formula

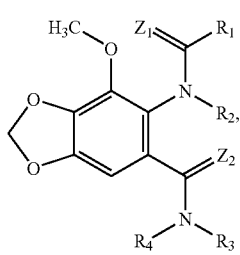
(T86)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 87

This table discloses the 338 compounds T87.1 to T87.338 of the formula

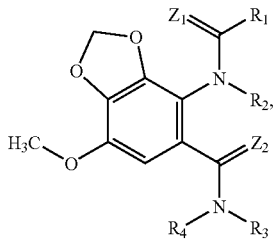
(T87)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 88

This table discloses the 338 compounds T88.1 to T88.338 of the formula

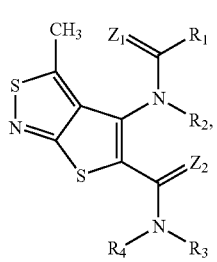
(T88)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 89

This table discloses the 338 compounds T89.1 to T89.338 of the formula

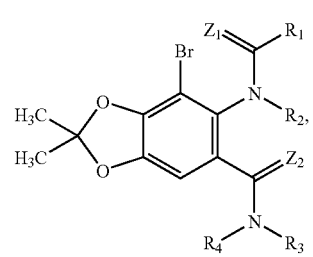
(T89)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 90

This table discloses the 338 compounds T90.1 to T90.338 of the formula

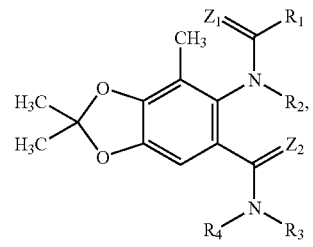
(T90)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

TABLE 91

This table discloses the 338 compounds T91.1 to T91.338 of the formula

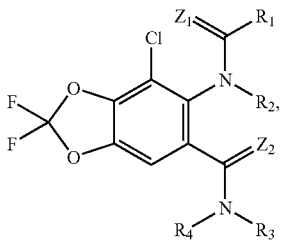

(T91)

in which, for each of these 338 specific compounds, each of the variables $Z_1$, $Z_2$, $R_1$, $R_2$, $R_3$ and $R_4$ has the specific meaning given in the corresponding line, appropriately selected from the 338 lines A.1 to A.338, of the Table A.

Formulation Examples

%=Per Cent by Weight

Example F1: Emulsion concentrates

|  | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2: Solutions

|  | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3: Granules

|  | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4: Dusts

|  | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5: Wettable powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6: Extruder granules

|  |  |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7: Coated granules

|  |  |
|---|---|
| Active ingredient | 3% |
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8: Suspension concentrate

|  |  |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |

-continued

| Example F8: Suspension concentrate | |
|---|---|
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

Biological Examples

%=Per Cent by Weight, Unless Otherwise Specified

Example B1

Activity Against *Aphis craccivora*

Pea seedlings are infected with Aphis craccivora, subsequently sprayed with a spray mixture comprising 400 ppm of active ingredient and then incubated at 20°. 3 and 6 days later, the percentage reduction in the population (% activity) is determined by comparing the number of dead aphids between the treated and untreated plants.

In this test, compounds listed in the Tables 1 to 85 show good activity.

Example B2

Activity Against *Diabrotica balteata*

Maize seedlings are sprayed with an aqueous emulsion spray mixture comprising 400 ppm of active ingredient and, after the spray coating has dried on, populated with 10 larvae (2nd instar) of *Diabrotica balteata* and introduced into a plastic container. 6 days later, the percentage reduction in the population (% activity) is determined by comparing the number of dead larvae between the treated and untreated plants.

In this test, compounds listed in the Tables 1 to 85 show good activity. In particular, the compounds T1.1, T1.3, T7.1 and T7.3 have an activity of over 80%.

Example B3

Activity Against *Heliothis virescens* (Foliar Application)

Young soya plants are sprayed with an aqueous emulsion spray mixture comprising 400 ppm of active ingredient and, after the spray coating has dried on, populated with 10 caterpillars (1st instar) of Heliothis virescens and introduced into a plastic container. 6 days later, the percentage reduction in the population and in the feeding damage (% activity) are determined by comparing the number of dead caterpillars and the feeding damage between the treated and untreated plants.

In this test, compounds listed in the Tables 1 to 85 show good activity. In particular, the compounds T1.1, T1.3, T2.1, T7.1, T7.3, T75.1, T75.3, T76.1, T76.3, T79.1, T81.1, T2.2, T8.1, T5.1, T5.3, T20.1, T20.3, T9.1, T9.3 and T9.2 have an activity of over 80%.

Example B4

Activity Against *Heliothis virescens* (Application to Eggs)

Heliothis virescens eggs, which have been deposited on cotton, are sprayed with an aqueous emulsion spray mixture comprising 400 ppm of active ingredient. After 8 days, the percentage hatching rate of the eggs and the survival rate of the caterpillars (% activity) are evaluated in comparison with untreated control batches.

In this test, compounds listed in the Tables 1 to 85 show good activity. In particular, the compounds T1.1, T1.3, T2.1, T7.1, T7.3, T75.1, T75.3, T76.1, T76.3, T79.1, T81.1, T2.2, T8.1, T5.1, T5.3, T20.1, T20.3, T9.1, T9.3 and T9.2 have an activity of over 80%.

Example B5

Activity Against *Myzus persicae* (Foliar Application)

Pea seedlings are infected with *Myzus persicae*, subsequently sprayed with a spray mixture comprising 400 ppm of active ingredient and then incubated at 20°. 3 and 6 days later, the percentage reduction in the population (% activity) is determined by comparing the number of dead aphids between the treated and untreated plants.

In this test, compounds listed in the Tables 1 to 85 show good activity. In particular, the compounds T1.1 and T7.1 have an activity of over 80%.

Example B6

Activity Against *Myzus persicae* (Systemic Application)

Pea seedlings are infected with *Myzus persicae*, and their roots are subsequently placed into a spray mixture comprising 400 ppm of active ingredient. The seedlings are then incubated at 20°. 3 and 6 days later, the percentage reduction in the population (% activity) is determined by comparing the number of dead aphids between the treated and untreated plants.

In this test, compounds listed in the Tables 1 to 85 show good activity.

Example B7

Activity Against *Plutella xylostella*

Young cabbage plants are sprayed with an aqueous emulsion spray mixture comprising 400 ppm of active ingredient and, after the spray coating has dried on, populated with 10 caterpillars (3rd instar) of Plutella xylostella and introduced into a plastic container. 3 days later, the percentage reduction in the population and in the feeding damage (% activity) are determined by comparing the number of dead caterpillars and the feeding damage between the treated and untreated plants.

In this test, compounds listed in the Tables 1 to 85 show good activity. In particular, the compounds T1.1, T1.3, T2.1, T7.1, T7.3, T22.3, T75.1, T75.3, T76.1, T76.3, T78.1, T79.1, T81.1, T2.2, T8.1, T5.1, T5.3, T20.1, T20.3, T9.1, T9.3 and T9.2 have an activity of over 80%.

Example B8

Activity Against *Spodoptera littoralis*

Young soya plants are sprayed with an aqueous emulsion spray mixture comprising 400 ppm of active ingredient and, after the spray coating has dried on, populated with 10 caterpillars (1st instar) of Spodoptera littoralis and introduced into a plastic container. 3 days later, the percentage reduction in the population and in the feeding damage (% activity) are determined by comparing the number of dead caterpillars and the feeding damage between the treated and untreated plants.

In this test, compounds listed in the Tables 1 to 85 show good activity. In particular, the compounds T1.1, T1.3, T2.1, T7.1, T7.3, T75.1, T75.3, T76.1, T76.3, T2.2, T8.1, T5.1, T5.3, T20.1, T20.3, T9.1, T9.3 and T9.2 have an activity of over 80%.

What is claimed is:
1. A compound of either formulae VIIa and VIIb

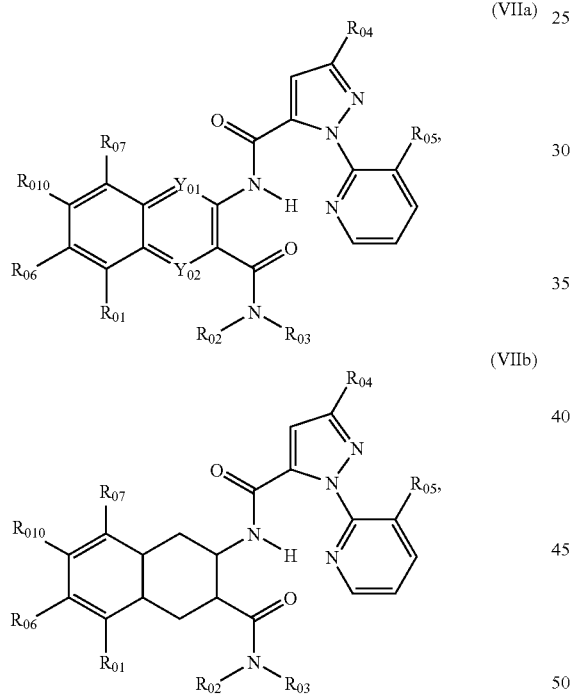

wherein
$R_{01}$ is hydrogen, amino, or nitro;
$R_{02}$ is hydrogen or $C_1$-$C_4$alkyl;
$R_{03}$ is $C_1$-$C_4$alkyl, $C_1$-$C_4$alkyl mono- or disubstituted by cyano, COOH, nitro, $C_1$-$C_4$alkoxy or cyclopropyl; $C_2$-$C_8$alkenyl; $C_2$-$C_8$alkenyl substituted by halogen; $C_1$-$C_4$alkoxy; $C_3$-$C_6$-alkynyl; cyclopropyl; cyclobutyl; cyclopentyl; cyclohexyl; cyclopropyl substituted by $C_1$-$C_4$alkyl, pyridyl, phenyl-$C_2$-$C_6$alkenyl or cyclopropyl; cyclobutyl substituted by $C_1$-$C_4$alkyl; cyclopentylthio-$C_1$-$C_4$alkyl; benzyloxy; benzyloxy substituted by halogen; benzylthio-$C_1$-$C_4$alkyl, wherein the benzyl group may itself be substituted by $C_1$-$C_4$alkyl; thiophenyl substituted by halophenyl; phenoxy-$C_1$-$C_4$alkyl, wherein the phenyl group may be mono- or disubstituted by halogen; phenyl-$C_1$-$C_4$alkyl, wherein the phenyl group may itself be mono- or disubstituted by substituents selected from halogen, nitro, benzothiazol-2-yloxy, $C_1$-$C_4$haloalkyl, $C_1$-$C_4$alkoxy and $C_1$-$C_4$alkyl; 3,4-dihydro-2H-benzo[b][1,4]dioxepinyl; 1,2,3,4-tetrahydronaphthalenyl substituted by $C_1$-$C_4$alkoxy; $C_2$-$C_6$alkenyloxy; isoxazolyl substituted by $C_1$-$C_4$alkyl; thiazolyl, $C_1$-$C_4$alkoxycarbonyl-$C_1$-$C_4$alkyl; phenyl substituted by hydroxy, halophenyloxy, $C_1$-$C_4$alkyl-silyl($C_1$-$C_4$-alkyl)$_3$ or $C_2$-$C_6$alkynyl; pyridyl substituted by $C_1$-$C_4$alkoxy; $C_1$-$C_6$alkylthio-$C_1$-$C_4$alkyl; $C_2$-$C_6$alkenylthio-$C_1$-$C_4$alkyl; $C_3$-$C_6$alkinylthio-$C_1$-$C_4$alkyl; dioxolan-2-yl-$C_1$-$C_4$alkyl; ($C_1$-$C_4$alkyl-dioxolan-2-yl)-$C_1$-$C_4$alkyl; triazolyl-$C_1$-$C_4$alkyl; thienyl-$C_1$-$C_4$alkyl; morpholinyl-$C_1$-$C_4$alkyl; $C_1$-$C_4$alkylthio-$C_1$-$C_4$alkyl; 2,3-dihydro-1H-isoindolyl; halo-substituted-thiazolyl-$C_1$-$C_4$alkyl; $C_1$-$C_4$alkylsulfonyl-$C_1$-$C_4$alkyl; or quinolylthio-$C_1$-$C_4$alkyl, wherein the quinoline group may be substituted by $C_1$-$C_4$haloalkyl;
$R_{04}$ is $C_1$-$C_4$haloalkyl;
$R_{05}$ is halogen;
each of $R_{06}$ and $R_{010}$, which may be the same or different, represents hydrogen, $C_1$-$C_6$alkyl, $C_1$-$C_6$alkoxycarbonyloxy, $C_1$-$C_6$alkylcarbonylamino, hydroxy, cyano, halogen or $C_1$-$C_6$alkoxy;
$R_{07}$ is hydrogen, nitro or halogen;
$Y_{01}$ is $C(R_{08})$, sulfur, nitrogen or a chemical bond;
$R_{08}$ is hydrogen, halogen, $C_1$-$C_4$alkyl or nitro;
$Y_{02}$ is $C(R_{09})$, a chemical bond, or is nitrogen or sulfur; and $R_{09}$ is hydrogen, phenyl, phenyl substituted by halogen, or halogen.

* * * * *